US008557844B2

(12) United States Patent
Platt et al.

(10) Patent No.: US 8,557,844 B2
(45) Date of Patent: Oct. 15, 2013

(54) SUBSTRATE REDUCTION THERAPY

(75) Inventors: Frances Mary Platt, Oxford (GB); Emyr Lloyd-Evans, Oxford (GB); Forbes Dennison Porter, Bethesda, MD (US)

(73) Assignees: The Chancellor, Masters and Scholars of the University of Oxford, Oxford (GB); The United States of America, as represented by the Secretary, Department of Health and Human Services, Washington, DC (US)

( * ) Notice: Subject to any disclaimer, the term of this patent is extended or adjusted under 35 U.S.C. 154(b) by 620 days.

(21) Appl. No.: 12/666,279

(22) PCT Filed: Jun. 26, 2008

(86) PCT No.: PCT/GB2008/002207
§ 371 (c)(1),
(2), (4) Date: Jan. 19, 2010

(87) PCT Pub. No.: WO2009/001097
PCT Pub. Date: Dec. 31, 2008

(65) Prior Publication Data
US 2010/0204162 A1 Aug. 12, 2010

(30) Foreign Application Priority Data
Jun. 27, 2007 (GB) .................................. 0712494.4

(51) Int. Cl.
*A61K 31/445* (2006.01)
*A61K 31/706* (2006.01)
(52) U.S. Cl.
USPC .......................................... 514/315; 514/27
(58) Field of Classification Search
USPC .................................. 514/27, 315
See application file for complete search history.

(56) References Cited

U.S. PATENT DOCUMENTS

| 6,720,184 B1 | 4/2004 | Merrill et al. |
| 2004/0034019 A1 | 2/2004 | Tomlinson et al. |
| 2005/0182020 A1 | 8/2005 | Worgall et al. |

FOREIGN PATENT DOCUMENTS

| EP | 1 528 056 A | 5/2005 |
| WO | WO 93/02673 A | 2/1993 |
| WO | WO 00/62780 A | 10/2000 |
| WO | WO 03/037338 A | 5/2003 |
| WO | WO 2004/007454 A | 1/2004 |
| WO | WO 2004/111002 A | 12/2004 |
| WO | WO 2005/009349 A | 2/2005 |
| WO | WO 2005/123055 A | 12/2005 |
| WO | WO 2006/037069 A | 4/2006 |
| WO | WO 2007/015175 A | 2/2007 |
| WO | WO 2007/123403 A | 11/2007 |
| WO | WO 2008/006007 A | 1/2008 |
| WO | WO 2008/012555 A | 1/2008 |

OTHER PUBLICATIONS

Saudubray et al., J. Inherit. Metab. Dis., 2006, 29, p. 261-274.*
Kornhuber et al., J. Med. Chem., 2008, 51, p. 219-237.*
Keller et al., J. Lipid Res., 2004, 45, p. 347-355.*
Kelley et al., J. Med. Genet., 2000, 37, p. 321-335.*
Porter, F.D., J. Clin. Invest., 2002, 110(6), p. 715-724.*
Steiner et al. "Sterol balance in the Smith-Lemli-Opitz syndrome: Reduction in whole body cholesterol synthesis and normal bile acid production," *Journal of Lipid Research*, vol. 41(9):1437-1447 (Sep. 2000).
Abe et al. "Agents for the treatment of glycosphingolipid storage disorders," *Current Drug Metabolism*, vol. 2(3):331-338 (2001).
Zervas et al. "Critical role for glycosphingolipids in Niemann-Pick disease type C," *Current Biology*, vol. 11(16):1283-1287 (Aug. 2001).
Mukherjee et al. "Lipid and cholesterol trafficking in NPC," *Biochimica and Biophysica Acta*, vol. 1685(1-3):28-37 (Oct. 2004).
Sturley et al. "The pathophysiology and mechanisms of NP-C disease," *Biochimica and Biophysica Acta*, vol. 1685(1-3):83-87 (Oct. 2004).
Fox et al. "The clinical potential of sphingolipid-based therapeutics," *Cellular and Molecular Life Sciences*, vol. 63(9):1017-1023 (Mar. 2006).
Norez et al. "Rescue of functional delF508-CFTR channels in cystic fibrosis epithelial cells by the alpha-glucosidase inhibitor miglustat," *Febs Letters*, vol. 580(8):2081-2086 (Apr. 2006).
Lloyd-Evans et al. "61. Smith-Lemli-Opitz syndrome: A closet lysosomal storage disease hiding within an inheritable metabolic disorder of cholesterol biosynthesis," *Molecular Genetics and Metabolism*, vol. 93(2):S29 (Jan. 2008).
Cox, "Eliglustat tartrate, an orally active glucocerebroside synthase inhibitor for the potential treatment of Gaucher disease and other lysosomal storage diseases," *Curr Opin Investig Drugs* 11(10):1169-81, Oct. 2010.
Jeyakumar et al., "Storage Solutions: Treating Lysosomal Disorders of the Brain," *Nature Reviews* 6:4-12, Sep. 2006.
Platt et al., "N-Butyldeoxygalactonojirimycin Inhibits Glycolipid Biosynthesis but Does Not Affect N-Linked Oligosaccharide Processing," *The Journal of Biological Chemistry* 269(43):27108-27114, 1994.
Platt et al., "N-Butyldeoxynojirimycin Is a Novel Inhibitor of Glycolipid Biosynthesis," *The Journal of Biological Chemistry* 269(11):8362-8365, 1994.
Platt et al., "Inhibition of substrate synthesis as a strategy for glycolipid lysosomal storage disease therapy," *J. Inherit. Metab.* 24:275-290, 2001.
Te Vruchte et al., "Accumulation of Glycocphingolipids in Niemann-Pick C Disease Disrupts Endosomal Transport," *The Journal of Biological Chemistry* 279(25):26167-26175, Jun. 18, 2004.

* cited by examiner

*Primary Examiner* — Shaojia Anna Jiang
*Assistant Examiner* — Jonathan S Lau
(74) *Attorney, Agent, or Firm* — Klarquist Sparkman, LLP

(57) ABSTRACT

The present invention provides a compound which is an inhibitor of sphingolipid biosynthesis for use in the treatment of a disease which has a secondary Niemann-Pick type C disease like cellular phenotype.

13 Claims, 9 Drawing Sheets

SUBSTRATE REDUCTION THERAPY

CROSS REFERENCE TO RELATED APPLICATIONS

This is the U.S. National Stage of International Application No. PCT/GB2008/002207, filed Jun. 26, 2008, which was published in English under PCT Article 21(2), which in turn claims the benefit of GB Application No. 0712494.4, filed Jun. 27, 2007.

FIELD OF THE INVENTION

The present invention relates to the treatment of diseases which have a secondary Niemann-Pick type C disease like cellular phenotype.

BACKGROUND TO THE INVENTION

Smith-Lemli-Opitz Syndrome (SLOS) is an autosomal recessive disorder caused by an inborn error of cholesterol biosynthesis. SLOS is estimated to have an incidence of 1:1,590 to 1:60,000 live births, making it the fifth commonest recessive disorder in Caucasians (Am. J. Med. Genetics, 2006; 140; p 2057-62). Clinical manifestations of SLOS are extremely variable. At the severe end of the spectrum SLOS is a lethal disorder, typical features of which include microcephaly, postaxial polydactyly, second and third toe syndactaly, cleft palate, genital anomalies, growth failure, and mental retardation. Mild SLOS cases combine minor physical stigmata with behavioural and learning disabilities. Intrauterine growth retardation is common and postnatal growth failure affects the majority of SLOS infants. At least 95% of SLOS patients present with some degree of mental retardation and learning disabilities. (Mol Genet Metab 2000; 71(1-2):163-74; Ann Hum Genet 2003; 67(Pt 3):269-80)

Biochemically, SLOS is caused by a deficiency in 3β-hydroxysterol $\Delta^7$-reductase. This is an NADPH-dependent ER enzyme that catalyses the reduction of the C7(8) double bond of the class II amphiphile 7-dehydrocholesterol (7-DHC) to yield cholesterol in the final step of cholesterol biosynthesis, via the Kandutsch-Russel pathway (FIG. 1) (Am J Hum Genet 1998; 63(1):55-62). This results in decreased cholesterol levels in all cells and tissues and an increase in sterol precursors. In particular, this results in an increase in the cholesterol precursor 7-DHC (Mol Genet Metab 2000; 71(1-2):163-74).

One potential therapy for SLOS patients is to increase dietary cholesterol to compensate for the endogenous block in cholesterol biosynthesis. However, in patients this therapy produces only limited clinical benefit. Increasing dietary cholesterol does not significantly alter the level of cholesterol or 7-DHC in the cerebrospinal fluid, which may explain why mental improvement in response to this therapy is very limited (Mol Genet Metab 2000; 71(1-2):154-62). For a more effective therapy it may be necessary to reduce 7-DHC storage in addition to increasing cholesterol levels (Mol Genet Metab 2000; 71(1-2):163-74). Current therapies combine increasing exogenously delivered cholesterol whilst attempting to lower 7-DHC levels by inhibiting de novo sterol synthesis using simvastatin (Mol Genet Metab 2005; 85(2):96-107). There is however a need for greater understanding of the effects of 7-DHC elevation within the cell, which may lead to the identification of additional targets for therapeutic intervention.

Cells obtain cholesterol either by de novo synthesis (FIG. 1) or exogenously by binding of LDL particles to LDL-receptors at the plasma membrane (PM) and subsequent endocytic uptake in clathrin coated pits (FIG. 1) (Mol Genet Metab 2002; 75(4):325-34). Free cholesterol is released from the LDL particle via the action of acid lipase in the late endosome. From here it is transported to the ER where it can be recycled to the PM or esterified. As current SLOS therapies focus on increasing the delivery of exogenous cholesterol, one recent study (Mol Genet Metab 2002; 75(4):325-34) has focussed on the effect of increasing intracellular concentrations of 7-DHC on LDL-derived cholesterol internalization, transport, and metabolism. Growth of SLOS patient fibroblasts in lipoprotein deficient serum (LPDS, which contains no LDL) lowers exogenously derived cholesterol. This results in up-regulation of the endogenous cholesterol synthesis pathway, leading to intracellular accumulation of 7-DHC in SLOS cells (owing to the failure to convert 7-DHC to cholesterol). The effect of 7-DHC storage on free cholesterol transport was assessed by re-addition of LDL to the culture medium for 24 h following an initial 5-day incubation in medium supplemented with LPDS. Under conditions of 7-DHC accumulation in SLOS cells LDL derived free cholesterol was found to accumulate in the late endosomes/lysosomes (LE/Lys) system (confirmed by electron microscopy, Mol Genet Metab 2002; 75(4):325-34). These results indicate that dietary cholesterol supplementation may not be fully utilised by SLOS patients.

There is therefore a need to develop improved treatments for SLOS and related disorders.

SUMMARY OF THE INVENTION

The present invention relates to the findings presented herein that the accumulation in SLOS cells of the class II amphiphile 7-DHC causes abnormal sphingolipid storage and transport in the LE/Lys system (a Niemann-Pick type C disease like cellular phenotype), and that the treatment of such cells with an inhibitor of sphingolipid biosynthesis corrects these abnormalities. These findings support that inhibitors of sphingolipid biosynthesis can ameliorate the intracellular cholesterol transport defect associated with SLOS. Such inhibitors are therefore of potential therapeutic benefit to SLOS patients and to patients of other diseases which have a secondary Niemann-Pick type C disease like cellular phenotype.

Accordingly, the present invention provides a compound which is an inhibitor of sphingolipid biosynthesis for use in the treatment of a disease which has a secondary Niemann-Pick type C disease like cellular phenotype.

The invention also provides a method of treating a disease which has a secondary Niemann-Pick type C disease like cellular phenotype, which method comprises administering to a patient in need of such treatment an effective amount of a compound which is an inhibitor of sphingolipid biosynthesis.

The invention also provides a pharmaceutical composition for use in treating a disease which has a secondary Niemann-Pick type C disease like cellular phenotype, comprising a pharmaceutically acceptable carrier or diluent and a compound which is an inhibitor of sphingolipid biosynthesis.

The invention also provides the use of a compound which is an inhibitor of sphingolipid biosynthesis in the manufacture of a medicament for the treatment of a disease which has a secondary Niemann-Pick type C disease like cellular phenotype.

The invention also provides an agent for the treatment of a disease which has a secondary Niemann-Pick type C disease like cellular phenotype, comprising a compound which is an inhibitor of sphingolipid biosynthesis.

Typically, the compound is an inhibitor of sphingolipid biosynthesis of the following formula (I), formula (II), formula (III), formula (IV), formula (V), formula (IX) or formula (XII) or a pharmaceutically acceptable salt thereof.

Accordingly, the invention further provides a compound for use in the treatment of a disease which has a secondary Niemann-Pick type C disease like cellular phenotype, which compound is an inhibitor of sphingolipid biosynthesis of formula (I), formula (II), formula (III), formula (IV), formula (V), formula (IX) or formula (XII):

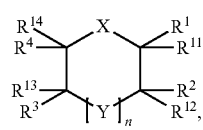
(I)

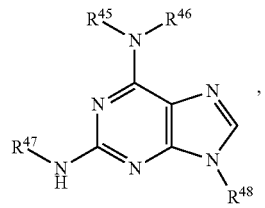
(III)

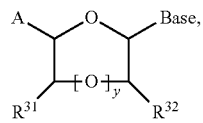
(V)

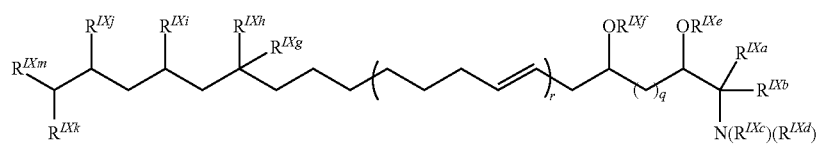
(IX)

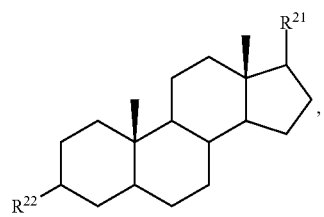
(II)

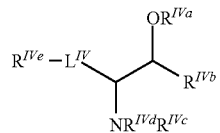
(IV)

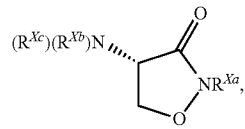
(XII)

wherein:

X is O, S or $NR^5$;

$R^5$ is hydrogen, substituted or unsubstituted $C_{1-20}$ alkyl, substituted or unsubstituted $C_{1-20}$ alkylene-aryl, substituted or unsubstituted $C_{1-20}$ alkylene-$C_{3-20}$ heteroaryl, substituted or unsubstituted $C_{1-20}$ alkylene-$C_{3-25}$ cycloalkyl, substituted or unsubstituted $C_{1-20}$ alkylene-$C_{3-20}$ heterocyclyl, substituted or unsubstituted $C_{1-20}$ alkylene-O—$C_{3-20}$ heterocyclyl, substituted or unsubstituted aryl, substituted or unsubstituted $C_{3-20}$ heteroaryl, substituted or unsubstituted $C_{3-25}$ cycloalkyl or substituted or unsubstituted $C_{3-20}$ heterocyclyl, or $R^5$ forms, together with $R^1$, $R^{11}$, $R^4$ or $R^{14}$, a substituted or unsubstituted $C_{1-6}$ alkylene group, wherein said $C_{1-20}$ alkyl and $C_{1-20}$ alkylene are optionally interrupted by N(R'), O, S or arylene wherein R' is H, $C_{1-6}$ alkyl or aryl;

n is 0 or 1;

Y is O, S or $CR^6R^{16}$;

$R^1$, $R^{11}$, $R^4$ and $R^{14}$, which may be the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido, —O—$C_{3-25}$ cycloalkyl and —O—$C_{3-20}$ heterocyclyl, provided that one of $R^1$, $R^{11}$, $R^4$ and $R^{14}$ may form, together with $R^5$, a substituted or unsubstituted $C_{1-6}$ alkylene group, wherein said $C_{1-20}$ alkyl is optionally interrupted by N(R'), O, S or arylene;

$R^2$, $R^{12}$, $R^3$, $R^{13}$, $R^6$ and $R^{16}$, which may be the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido —O—$C_{3-25}$ cycloalkyl and —O—$C_{3-20}$ heterocyclyl, wherein said $C_{1-20}$ alkyl is optionally interrupted by N(R'), O, S or arylene;

$R^{21}$ is selected from oxo, -$L^{30}$-$R^{23}$, -$L^{30}$-C(O)N(H)—$R^{24}$ and a group of the following formula (VI):

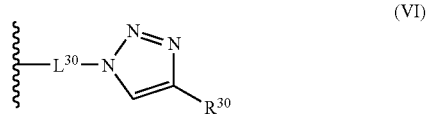
(VI)

$L^{30}$ is substituted or unsubstituted $C_{1-20}$ alkylene which is optionally interrupted by N(R'), O, S or arylene;

$R^{23}$ is carboxyl, hydroxyl, ester, phosphonate ester, phosphate ester, phosphoric acid and phosphonic acid;

$R^{24}$ is $C_{1-20}$ alkyl which is unsubstituted or substituted with one or more groups selected from carboxyl, hydroxyl, ester, phosphonate ester, phosphate ester, phosphoric acid and phosphonic acid, wherein said $C_{1-20}$ alkyl is optionally interrupted by N(R'), O, S or arylene;

$R^{30}$ is $C_{1-20}$ alkyl which is unsubstituted or substituted with one or more groups selected from carboxyl, hydroxyl, ester, amino, phosphonate ester, phosphate ester, phosphoric acid and phosphonic acid, wherein said $C_{1-20}$ alkyl is optionally interrupted by N(R'), O, S or arylene;

$R^{22}$ is hydroxyl, oxo, acyloxy, phosphoric acid or —OC(O)-alk-C(O)OH, wherein alk is substituted or unsubstituted $C_{1-20}$ alkylene which is optionally interrupted by N(R'), O, S or arylene;

Base is selected from a group of any one of the following formulae (a), (b), (c), (d), (e), (f) and (g):

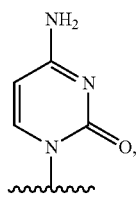
(a)

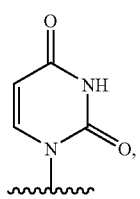
(b)

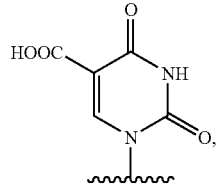
(c)

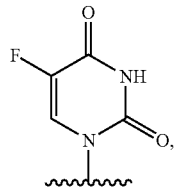
(d)

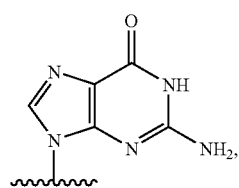
(e)

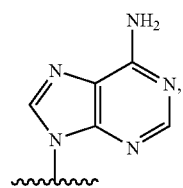
(f)

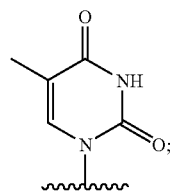
(g)

y is 0 or 1;

$R^{31}$ is OH; $R^{32}$ is H or OH; or, provided that y is 0, $R^{31}$ and $R^{32}$ together form —O—C($R^{33}$)($R^{34}$)—O—, wherein $R^{33}$ and $R^{34}$ are independently selected from H and methyl;

A is substituted or unsubstituted $C_{1-20}$ alkyl, substituted or unsubstituted $C_{1-20}$ alkylene-aryl, substituted or unsubstituted $C_{1-20}$ alkylene-$C_{3-20}$ heteroaryl, substituted or unsubstituted $C_{1-20}$ alkylene-$C_{3-25}$ cycloalkyl or substituted or unsubstituted $C_{1-20}$ alkylene-$C_{3-20}$ heterocyclyl, wherein said $C_{1-20}$ alkyl and $C_{1-20}$ alkylene are optionally interrupted by N(R'), O, S or arylene, wherein R' is H, $C_{1-6}$ alkyl or aryl, or A is a group of any one of the following formulae (g) to (k):

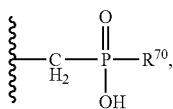
(g)

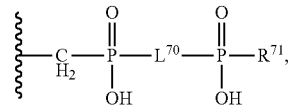
(h)

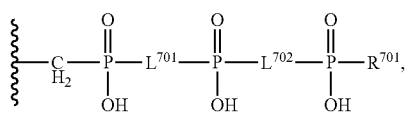
(i)

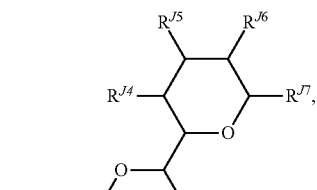
(j)

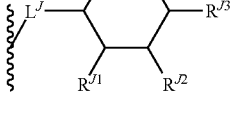
(k)

$L^{70}$, $L^{701}$ and $L^{702}$ are independently selected from —O—, —C($R^{35}$)($R^{36}$)— and —NH—, wherein $R^{35}$ and $R^{36}$ are independently selected from H, OH and $CH_3$;

$R^{70}$, $R^{71}$ and $R^{701}$ are selected from OH, substituted or unsubstituted $C_{1-20}$ alkyl, substituted or unsubstituted $C_{1-20}$ alkoxy, substituted or unsubstituted $C_{1-10}$ alkylamino and -$L^{71}$-($X^2$)$_m$-$L^{72}$-$R^{72}$; wherein m is 0 or 1; $X^2$ is O, S, —C($R^{45}$)($R^{46}$)— or —O—C($R^{45}$)($R^{46}$)—, wherein $R^{45}$ and $R^{46}$ are independently selected from H, OH, phosphonic acid or a phosphonic acid salt; $L^{71}$ and $L^{72}$ are independently selected from a single bond and substituted or unsubstituted $C_{1-20}$ alkylene, which $C_{1-20}$ alkylene is optionally interrupted by N(R'), O, S or arylene, wherein R' is H, $C_{1-6}$ alkyl or aryl; and $R^{72}$ is $C_{3-25}$ cycloalkyl or $C_{3-20}$ heterocyclyl;

$L^J$ is substituted or unsubstituted $C_{1-20}$ alkylene;

$R^{J1}$, $R^{J2}$, $R^{J3}$, $R^{J4}$, $R^{J5}$, $R^{J6}$ and $R^{J7}$, which are the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido, —N(H)C(O)CH=CH—$R^{J8}$, —O—$C_{3-25}$ cycloalkyl and —O—$C_{3-20}$ heterocyclyl, wherein said $C_{1-20}$ alkyl is optionally interrupted by N(R'), O, S or arylene, and wherein $R^{J8}$ is substituted or unsubstituted $C_{1-20}$ alkyl;

$L^{K1}$ and $L^{K2}$, which are the same or different, are independently selected from a single bond and substituted or unsubstituted $C_{1-20}$ alkylene;

$X^K$ is N or C($R^{K6}$), wherein $R^{K6}$ is H, COOH or ester;

$Z^K$ is O or CH($R^{K5}$);

p is 0 or 1;

$R^{K1}$, $R^{K2}$, $R^{K3}$, $R^{K4}$ and $R^{K5}$, which are the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido, —O—$C_{3-25}$ cycloalkyl and —O—$C_{3-20}$ heterocyclyl, wherein said $C_{1-20}$ alkyl is optionally interrupted by N(R'), O, S or arylene;

$R^{IVa}$ and $R^{IVd}$, which are the same or different, are independently selected from H, substituted or unsubstituted $C_{1-6}$ alkyl or substituted or unsubstituted phenyl;

$R^{IVb}$ is H, substituted or unsubstituted aryl, —CH=CHR$^{IVf}$, or substituted or unsubstituted $C_{1-20}$ alkyl, which $C_{1-20}$ alkyl is optionally interrupted by N(R'), O, S or arylene wherein R' is H, $C_{1-6}$ alkyl or aryl;

$R^{IVc}$ is H, substituted or unsubstituted $C_{1-6}$ alkyl, substituted or unsubstituted phenyl or —C(O)R$^{IVg}$;

$R^{IVf}$ is H or substituted or unsubstituted $C_{1-20}$ alkyl, which $C_{1-20}$ alkyl is optionally interrupted by N(R'), O, S or arylene;

$R^{IVg}$ is H or substituted or unsubstituted $C_{1-20}$ alkyl, which $C_{1-20}$ alkyl is optionally interrupted by N(R'), O, S or arylene;

$R^{IVe}$ is H, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido, —O—$C_{3-25}$ cycloalkyl, —O—$C_{3-20}$ heterocyclyl, substituted or unsubstituted aryl, substituted or unsubstituted $C_{3-20}$ heteroaryl, substituted or unsubstituted $C_{3-25}$ cycloalkyl or substituted or unsubstituted $C_{3-20}$ heterocyclyl, which $C_{1-20}$ alkyl is optionally interrupted by N(R'), O, S or arylene;

$L^{IV}$ is substituted or unsubstituted $C_{1-20}$ alkylene which $C_{1-20}$ alkylene is optionally interrupted by N(R'), O, S or arylene;

$R^{91}$ and $R^{92}$, which are the same or different, are independently selected from H, substituted or unsubstituted $C_{1-20}$ alkyl, substituted or unsubstituted aryl and -$L^{91}$-$R^{95}$, wherein $L^{91}$ is substituted or unsubstituted $C_{1-20}$ alkylene, wherein said $C_{1-20}$ alkyl and said $C_{1-20}$ alkylene are optionally interrupted by N(R'), O, S or arylene wherein R' is H, $C_{1-6}$ alkyl or aryl, and wherein $R^{95}$ is substituted or unsubstituted aryl, amino, $C_{1-10}$ alkylamino or di($C_{1-10}$)alkylamino;

$R^{93}$ is -$L^{92}$-$R^{96}$, wherein $L^{92}$ is a single bond or substituted or unsubstituted $C_{1-20}$ alkylene, which $C_{1-20}$ alkylene is optionally interrupted by N(R'), O, S or arylene, and wherein $R^{96}$ is amido or substituted or unsubstituted aryl;

$R^{94}$ is H or substituted or unsubstituted $C_{1-20}$ alkyl, which $C_{1-20}$ alkyl is optionally interrupted by N(R'), O, S or arylene;

q is 0 or 1;

r is 0 or 1;

$R^{IXa}$ is H, COOH or an unsubstituted or substituted ester;

$R^{IXb}$ is an unsubstituted or substituted $C_{1-6}$ alkyl;

$R^{IXc}$ and $R^{IXd}$, which are the same or different, are each independently selected from H, unsubstituted or substituted $C_{1-6}$ alkyl and unsubstituted or substituted phenyl;

$R^{IXe}$ and $R^{IXf}$, which are the same or different, are each independently selected from H, unsubstituted or substituted $C_{1-6}$ alkyl, unsubstituted or substituted phenyl and unsubstituted or substituted acyl;

either (a) one of $R^{IXg}$ and $R^{IXh}$ is H and the other is OR$^{IXr}$, wherein $R^{IXr}$ is selected from H, unsubstituted or substituted $C_{1-6}$ alkyl, unsubstituted or substituted phenyl and unsubstituted or substituted acyl, or (b) $R^{IXg}$ and $R^{IXh}$ together form an oxo group;

$R^{IXi}$ is H, unsubstituted or substituted $C_{1-6}$ alkyl, unsubstituted or substituted $C_{1-6}$ alkoxy and unsubstituted or substituted phenyl;

$R^{IXj}$ is H, unsubstituted or substituted $C_{1-6}$ alkyl or a group of the following formula (X):

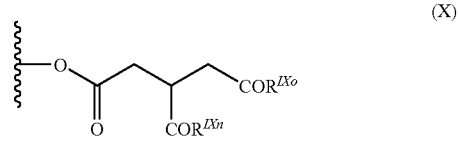

(X)

in which $R^{IXn}$ and $R^{IXo}$, which are the same or different, are each independently selected from OH, unsubstituted or substituted $C_{1-6}$ alkoxy, unsubstituted or substituted phenoxy, amino, unsubstituted or substituted $C_{1-6}$ alkylamino and unsubstituted or substituted di($C_{1-6}$)alkylamino;

$R^{IXk}$ is H, unsubstituted or substituted $C_{1-6}$ alkyl or a group of the following formula (XI):

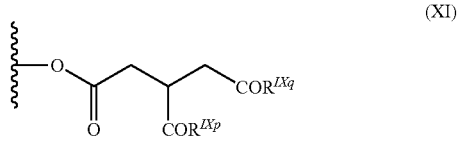

(XI)

in which $R^{IXp}$ and $R^{IXq}$, which are the same or different, are each independently selected from OH, unsubstituted or substituted $C_{1-6}$ alkoxy, unsubstituted or substituted phenoxy, amino, unsubstituted or substituted $C_{1-6}$ alkylamino and unsubstituted or substituted di($C_{1-6}$)alkylamino;

$R^{IXm}$ is selected from H and unsubstituted or substituted $C_{1-20}$ alkyl, which $C_{1-20}$ alkyl is optionally interrupted by N(R'), O, S or phenylene, wherein R' is H, $C_{1-6}$ alkyl or phenyl;

$R^{Xa}$ is H, substituted or unsubstituted $C_{1-20}$ alkyl, substituted or unsubstituted $C_{1-20}$ alkylene-aryl, substituted or unsubstituted $C_{1-20}$ alkylene-$C_{3-20}$ heteroaryl, substituted or unsubstituted $C_{1-20}$ alkylene-$C_{3-25}$ cycloalkyl, substituted or unsubstituted $C_{1-20}$ alkylene-$C_{3-20}$ heterocyclyl, substituted or unsubstituted $C_{1-20}$ alkylene-O—$C_{3-20}$ heterocyclyl, substituted or unsubstituted aryl, substituted or unsubstituted $C_{3-20}$ heteroaryl or substituted or unsubstituted $C_{3-25}$ cycloalkyl or substituted or unsubstituted $C_{3-20}$ heterocyclyl wherein said $C_{1-20}$ alkyl and $C_{1-20}$ alkylene are optionally interrupted by N(R'), O, S or arylene wherein R' is H, $C_{1-6}$ alkyl or aryl; and $R^{Xb}$ and $R^{Xc}$, which are the same or different, are independently selected from H, unsubstituted or substituted $C_{1-10}$ alkyl and unsubstituted or substituted aryl;

or a pharmaceutically acceptable salt thereof.

Alternatively, the inhibitor of sphingolipid biosynthesis is RNA.

Accordingly, the invention further provides a compound which is an inhibitor of sphingolipid biosynthesis for use in the treatment of a disease which has a secondary Niemann-Pick type C disease like cellular phenotype, wherein the inhibitor of sphingolipid biosynthesis is RNA.

Typically, the disease which has a secondary Niemann-Pick type C disease like cellular phenotype is other than mucopolysaccharidosis and other than mucolipidosis IV. The term "mucopolysaccharidosis", as used herein includes all the mucopolysaccharidoses, including mucopolysaccharidosis types I, II, III, IV, V, VI and VII.

Accordingly, in another aspect the present invention provides a compound which is an inhibitor of sphingolipid biosynthesis for use in the treatment of a disease which has a secondary Niemann-Pick type C disease like cellular phenotype, provided that the disease is other than mucopolysaccharidosis and other than mucolipidosis IV.

The invention also provides a method of treating a disease which has a secondary Niemann-Pick type C disease like cellular phenotype, which method comprises administering to a patient in need of such treatment an effective amount of a compound which is an inhibitor of sphingolipid biosynthesis, provided that the disease is other than mucopolysaccharidosis and other than mucolipidosis IV.

The invention also provides a pharmaceutical composition for use in treating a disease which has a secondary Niemann-Pick type C disease like cellular phenotype, comprising a pharmaceutically acceptable carrier or diluent and a compound which is an inhibitor of sphingolipid biosynthesis, provided that the disease is other than mucopolysaccharidosis and other than mucolipidosis IV.

The invention also provides the use of a compound which is an inhibitor of sphingolipid biosynthesis in the manufacture of a medicament for the treatment of a disease which has a secondary Niemann-Pick type C disease like cellular phenotype, provided that the disease is other than mucopolysaccharidosis and other than mucolipidosis IV.

The invention also provides an agent for the treatment of a disease which has a secondary Niemann-Pick type C disease like cellular phenotype, comprising a compound which is an inhibitor of sphingolipid biosynthesis, provided that the disease is other than mucopolysaccharidosis and other than mucolipidosis IV.

Typically, the compound is an inhibitor of sphingolipid biosynthesis of the following formula (I), formula (II), formula (III), formula (IV), formula (V), formula (IX) or formula (XII) or a pharmaceutically acceptable salt thereof.

Accordingly, the invention further provides a compound for use in the treatment of a disease which has a secondary Niemann-Pick type C disease like cellular phenotype, provided that the disease is other than mucopolysaccharidosis and other than mucolipidosis IV, which compound is an inhibitor of sphingolipid biosynthesis of formula (I), formula (II), formula (III), formula (IV), formula (V), formula (IX) or formula (XII):

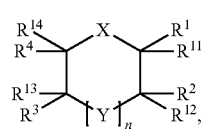
(I)

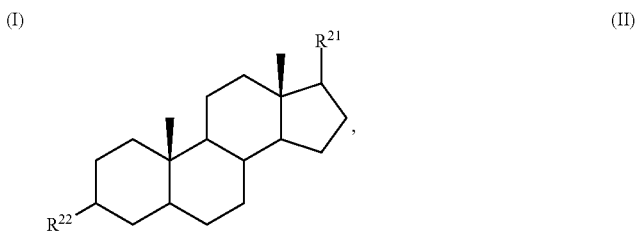
(II)

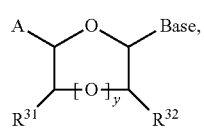
(III)

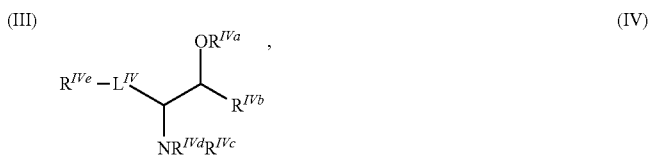
(IV)

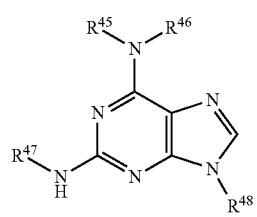
(V)

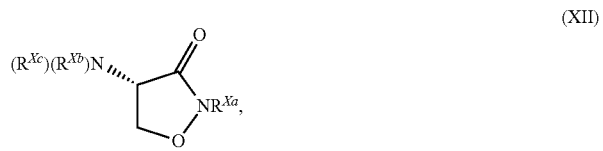
(XII)

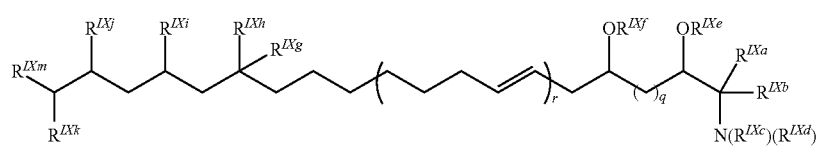
(IX)

wherein:

X is O, S or NR$^5$;

R$^5$ is hydrogen, substituted or unsubstituted C$_{1-20}$ alkyl, substituted or unsubstituted C$_{1-20}$ alkylene-aryl, substituted or unsubstituted C$_{1-20}$ alkylene-C$_{3-20}$ heteroaryl, substituted or unsubstituted C$_{1-20}$ alkylene-C$_{3-25}$ cycloalkyl, substituted or unsubstituted C$_{1-20}$ alkylene-C$_{3-20}$ heterocyclyl, substituted or unsubstituted C$_{1-20}$ alkylene-O—C$_{3-20}$ heterocyclyl, substituted or unsubstituted aryl, substituted or unsubstituted C$_{3-20}$ heteroaryl, substituted or unsubstituted C$_{3-25}$ cycloalkyl or substituted or unsubstituted C$_{3-20}$ heterocyclyl, or R$^5$ forms, together with R$^1$, R$^{11}$, R$^4$ or R$^{14}$, a substituted or unsubstituted C$_{1-6}$ alkylene group, wherein said C$_{1-20}$ alkyl and C$_{1-20}$ alkylene are optionally interrupted by N(R'), O, S or arylene wherein R' is H, C$_{1-6}$ alkyl or aryl;

n is 0 or 1;

Y is O, S or CR$^6$R$^{16}$;

R$^1$, R$^{11}$, R$^4$ and R$^{14}$, which may be the same or different, are independently selected from hydrogen, hydroxyl, carboxyl, amino, thiol, substituted or unsubstituted C$_{1-20}$ alkyl, substituted or unsubstituted C$_{1-20}$ alkoxy, substituted or unsubstituted aryloxy, acyl, ester, acyloxy, C$_{1-10}$ alkylamino, di(C$_{1-10}$)alkylamino, amido, acylamido, —O—C$_{3-25}$ cycloalkyl and —O—C$_{3-20}$ heterocyclyl, provided that one of R$^1$, R$^{11}$, R$^4$ and R$^{14}$ may form, together with R$^5$, a substituted or unsubstituted C$_{1-6}$ alkylene group, wherein said C$_{1-20}$ alkyl is optionally interrupted by N(R'), O, S or arylene;

R$^2$, R$^{12}$, R$^3$, R$^{13}$, R$^6$ and R$^{16}$, which may be the same or different, are independently selected from hydrogen, hydroxyl, carboxyl, amino, thiol, substituted or unsubstituted C$_{1-20}$ alkyl, substituted or unsubstituted C$_{1-20}$ alkoxy, substituted or unsubstituted aryloxy, acyl, ester, acyloxy, C$_{1-10}$ alkylamino, di(C$_{1-10}$)alkylamino, amido, acylamido —O—C$_{3-25}$ cycloalkyl and —O—C$_{3-20}$ heterocyclyl, wherein said C$_{1-20}$ alkyl is optionally interrupted by N(R'), O, S or arylene;

R$^{21}$ is selected from oxo, -L$^{30}$-R$^{23}$, -L$^{30}$-C(O)N(H)—R$^{24}$ and a group of the following formula (VI):

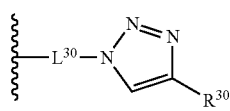

(VI)

L$^{30}$ is substituted or unsubstituted C$_{1-20}$ alkylene which is optionally interrupted by N(R'), O, S or arylene;

R$^{23}$ is carboxyl, hydroxyl, ester, phosphonate ester, phosphate ester, phosphoric acid and phosphonic acid;

R$^{24}$ is C$_{1-20}$ alkyl which is unsubstituted or substituted with one or more groups selected from carboxyl, hydroxyl, ester, phosphonate ester, phosphate ester, phosphoric acid and phosphonic acid, wherein said C$_{1-20}$ alkyl is optionally interrupted by N(R'), O, S or arylene;

R$^{30}$ is C$_{1-20}$ alkyl which is unsubstituted or substituted with one or more groups selected from carboxyl, hydroxyl, ester, amino, phosphonate ester, phosphate ester, phosphoric acid and phosphonic acid, wherein said C$_{1-20}$ alkyl is optionally interrupted by N(R'), O, S or arylene;

R$^{22}$ is hydroxyl, oxo, acyloxy, phosphoric acid or —OC(O)-alk-C(O)OH, wherein alk is substituted or unsubstituted C$_{1-20}$ alkylene which is optionally interrupted by N(R'), O, S or arylene;

Base is selected from a group of any one of the following formulae (a), (b), (c), (d), (e), (f) and (g):

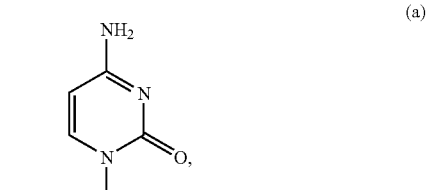
(a)

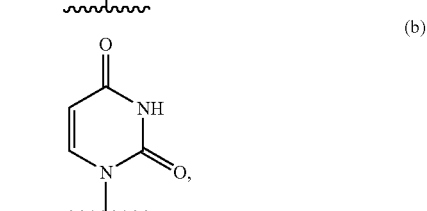
(b)

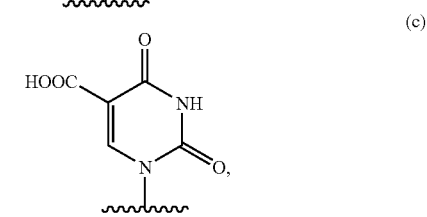
(c)

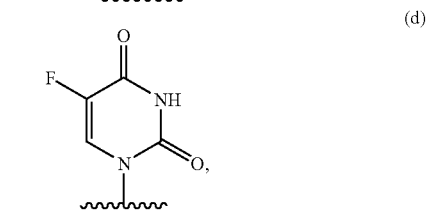
(d)

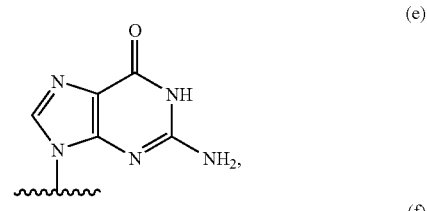
(e)

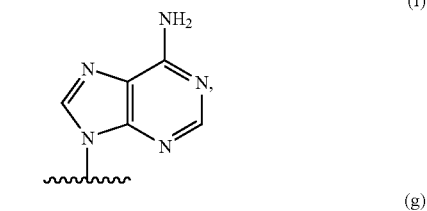
(f)

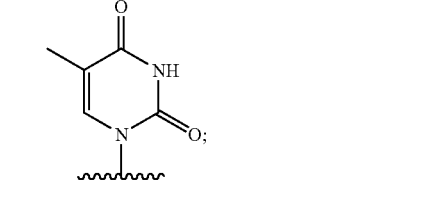
(g)

y is 0 or 1;

R$^{31}$ is OH; R$^{32}$ is H or OH; or, provided that y is 0, R$^{31}$ and R$^{32}$ together form —O—C(R$^{33}$)(R$^{34}$)—O—, wherein R$^{33}$ and R$^{34}$ are independently selected from H and methyl;

A is substituted or unsubstituted C$_{1-20}$ alkyl, substituted or unsubstituted C$_{1-20}$ alkylene-aryl, substituted or unsubstituted C$_{1-20}$ alkylene-C$_{3-20}$ heteroaryl, substituted or unsubstituted C$_{1-20}$ alkylene-C$_{3-25}$ cycloalkyl or substituted or unsubstituted C$_{1-20}$ alkylene-C$_{3-20}$ heterocyclyl, wherein said C$_{1-20}$ alkyl and C$_{1-20}$ alkylene are optionally interrupted by N(R'), O, S or arylene, wherein R' is H, C$_{1-6}$ alkyl or aryl, or A is a group of any one of the following formulae (g) to (k):

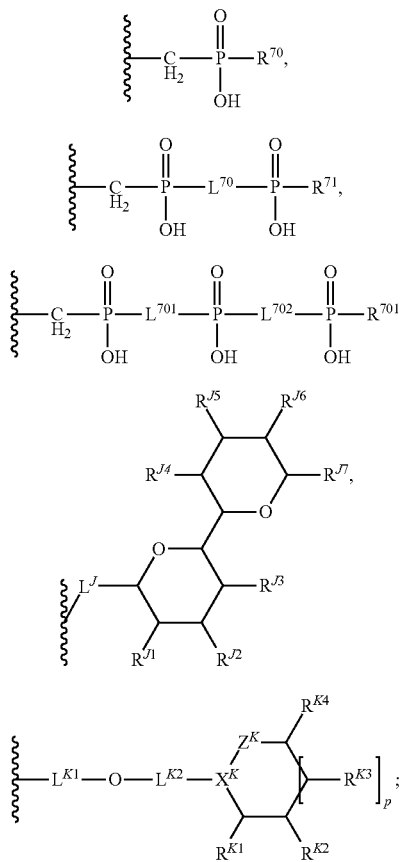

L$^{70}$, L$^{701}$ and L$^{702}$ are independently selected from —O—, —C(R$^{35}$)(R$^{36}$)— and —NH—, wherein R$^{35}$ and R$^{36}$ are independently selected from H, OH and CH$_3$;

R$^{70}$, R$^{71}$ and R$^{701}$ are selected from OH, substituted or unsubstituted C$_{1-20}$ alkyl, substituted or unsubstituted C$_{1-20}$ alkoxy, substituted or unsubstituted C$_{1-10}$ alkylamino and -L$^{71}$-(X$^2$)$_m$-L$^{72}$-R$^{72}$; wherein m is 0 or 1; X$^2$ is O, S, —C(R$^{45}$)(R$^{46}$)— or —O—C(R$^{45}$)(R$^{46}$)—, wherein R$^{45}$ and R$^{46}$ are independently selected from H, OH, phosphonic acid or a phosphonic acid salt; L$^{71}$ and L$^{72}$ are independently selected from a single bond and substituted or unsubstituted C$_{1-20}$ alkylene, which C$_{1-20}$ alkylene is optionally interrupted by N(R'), O, S or arylene, wherein R' is H, C$_{1-6}$ alkyl or aryl; and R$^{72}$ is C$_{3-25}$ cycloalkyl or C$_{3-20}$ heterocyclyl;

L$^J$ is substituted or unsubstituted C$_{1-20}$ alkylene;

R$^{J1}$, R$^{J2}$, R$^{J3}$, R$^{J4}$, R$^{J5}$, R$^{J6}$ and R$^{J7}$, which are the same or different, are independently selected from hydrogen, hydroxyl, carboxyl, amino, thiol, substituted or unsubstituted C$_{1-20}$ alkyl, substituted or unsubstituted C$_{1-20}$ alkoxy, substituted or unsubstituted aryloxy, acyl, ester, acyloxy, C$_{1-10}$ alkylamino, di(C$_{1-10}$)alkylamino, amido, acylamido, —N(H)C(O)CH═CH—R$^{J8}$, —O—C$_{3-25}$ cycloalkyl and —O—C$_{3-20}$ heterocyclyl, wherein said C$_{1-20}$ alkyl is optionally interrupted by N(R'), O, S or arylene, and wherein R$^{J8}$ is substituted or unsubstituted C$_{1-20}$ alkyl;

L$^{K1}$ and L$^{K2}$, which are the same or different, are independently selected from a single bond and substituted or unsubstituted C$_{1-20}$ alkylene;

X$^K$ is N or C(R$^{K6}$), wherein R$^{K6}$ is H, COOH or ester;

Z$^K$ is O or CH(R$^{K5}$);

p is 0 or 1;

R$^{K1}$, R$^{K2}$, R$^{K3}$, R$^{K4}$ and R$^{K5}$, which are the same or different, are independently selected from hydrogen, hydroxyl, carboxyl, amino, thiol, substituted or unsubstituted C$_{1-20}$ alkyl, substituted or unsubstituted C$_{1-20}$ alkoxy, substituted or unsubstituted aryloxy, acyl, ester, acyloxy, C$_{1-10}$ alkylamino, di(C$_{1-10}$)alkylamino, amido, acylamido, —O—C$_{3-25}$ cycloalkyl and —O—C$_{3-20}$ heterocyclyl, wherein said C$_{1-20}$ alkyl is optionally interrupted by N(R'), O, S or arylene;

R$^{IVa}$ and R$^{IVd}$, which are the same or different, are independently selected from H, substituted or unsubstituted C$_{1-6}$ alkyl or substituted or unsubstituted phenyl;

R$^{IVb}$ is H, substituted or unsubstituted aryl, —CH═CHR$^{IVf}$, or substituted or unsubstituted C$_{1-20}$ alkyl, which C$_{1-20}$ alkyl is optionally interrupted by N(R'), O, S or arylene wherein R' is H, C$_{1-6}$ alkyl or aryl;

R$^{IVc}$ is H, substituted or unsubstituted C$_{1-6}$ alkyl, substituted or unsubstituted phenyl or —C(O)R$^{IVg}$;

R$^{IVf}$ is H or substituted or unsubstituted C$_{1-20}$ alkyl, which C$_{1-20}$ alkyl is optionally interrupted by N(R'), O, S or arylene;

R$^{IVg}$ is H or substituted or unsubstituted C$_{1-20}$ alkyl, which C$_{1-20}$ alkyl is optionally interrupted by N(R'), O, S or arylene;

R$^{IVe}$ is H, hydroxyl, carboxyl, amino, thiol, substituted or unsubstituted C$_{1-20}$ alkyl, substituted or unsubstituted C$_{1-20}$ alkoxy, substituted or unsubstituted aryloxy, acyl, ester, acyloxy, C$_{1-10}$ alkylamino, di(C$_{1-10}$)alkylamino, amido, acylamido, —O—C$_{3-25}$ cycloalkyl, —O—C$_{3-20}$ heterocyclyl, substituted or unsubstituted aryl, substituted or unsubstituted C$_{3-20}$ heteroaryl, substituted or unsubstituted C$_{3-25}$ cycloalkyl or substituted or unsubstituted C$_{3-20}$ heterocyclyl, which C$_{1-20}$ alkyl is optionally interrupted by N(R'), O, S or arylene;

L$^{IV}$ is substituted or unsubstituted C$_{1-20}$ alkylene which C$_{1-20}$ alkylene is optionally interrupted by N(R'), O, S or arylene;

R$^{91}$ and R$^{92}$, which are the same or different, are independently selected from H, substituted or unsubstituted C$_{1-20}$ alkyl, substituted or unsubstituted aryl and -L$^{91}$-R$^{95}$, wherein L$^{91}$ is substituted or unsubstituted C$_{1-20}$ alkylene, wherein said C$_{1-20}$ alkyl and said C$_{1-20}$ alkylene are optionally interrupted by N(R'), O, S or arylene wherein R' is H, C$_{1-6}$ alkyl or aryl, and wherein R$^{95}$ is substituted or unsubstituted aryl, amino, C$_{1-10}$ alkylamino or di(C$_{1-10}$)alkylamino;

R$^{93}$ is -L$^{92}$-R$^{96}$, wherein L$^{92}$ is a single bond or substituted or unsubstituted C$_{1-20}$ alkylene, which C$_{1-20}$ alkylene is optionally interrupted by N(R'), O, S or arylene, and wherein R$^{96}$ is amido or substituted or unsubstituted aryl;

R$^{94}$ is H or substituted or unsubstituted C$_{1-20}$ alkyl, which C$_{1-20}$ alkyl is optionally interrupted by N(R'), O, S or arylene;

q is 0 or 1;

r is 0 or 1;

R$^{IXa}$ is H, COOH or an unsubstituted or substituted ester;

R$^{IXb}$ is an unsubstituted or substituted C$_{1-6}$ alkyl;

R$^{IXc}$ and R$^{IXd}$, which are the same or different, are each independently selected from H, unsubstituted or substituted C$_{1-6}$ alkyl and unsubstituted or substituted phenyl;

R$^{IXe}$ and R$^{IXf}$, which are the same or different, are each independently selected from H, unsubstituted or substituted C$_{1-6}$ alkyl, unsubstituted or substituted phenyl and unsubstituted or substituted acyl;

either (a) one of R$^{IXg}$ and R$^{IXh}$ is H and the other is OR$^{IXr}$, wherein R$^{IXr}$ is selected from H, unsubstituted or substituted C$_{1-6}$ alkyl, unsubstituted or substituted phenyl and unsubstituted or substituted acyl, or (b) R$^{IXg}$ and R$^{IXh}$ together form an oxo group;

$R^{IXi}$ is H, unsubstituted or substituted $C_{1-6}$ alkyl, unsubstituted or substituted $C_{1-6}$ alkoxy and unsubstituted or substituted phenyl;

$R^{IXj}$ is H, unsubstituted or substituted $C_{1-6}$ alkyl or a group of the following formula (X):

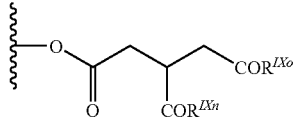

(X)

in which $R^{IXn}$ and $R^{IXo}$, which are the same or different, are each independently selected from OH, unsubstituted or substituted $C_{1-6}$ alkoxy, unsubstituted or substituted phenoxy, amino, unsubstituted or substituted $C_{1-6}$ alkylamino and unsubstituted or substituted di($C_{1-6}$)alkylamino;

$R^{IXk}$ is H, unsubstituted or substituted $C_{1-6}$ alkyl or a group of the following formula (XI):

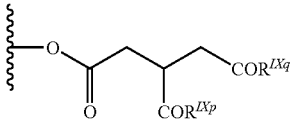

(XI)

in which $R^{IXp}$ and $R^{IXq}$, which are the same or different, are each independently selected from OH, unsubstituted or substituted $C_{1-6}$ alkoxy, unsubstituted or substituted phenoxy, amino, unsubstituted or substituted $C_{1-6}$ alkylamino and unsubstituted or substituted di($C_{1-6}$)alkylamino;

$R^{IXm}$ is selected from H and unsubstituted or substituted $C_{1-20}$ alkyl, which $C_{1-20}$ alkyl is optionally interrupted by N(R'), O, S or phenylene, wherein R' is H, $C_{1-6}$ alkyl or phenyl;

$R^{Xa}$ is H, substituted or unsubstituted $C_{1-20}$ alkyl, substituted or unsubstituted $C_{1-20}$ alkylene-aryl, substituted or unsubstituted $C_{1-20}$ alkylene-$C_{3-20}$ heteroaryl, substituted or unsubstituted $C_{1-20}$ alkylene-$C_{3-25}$ cycloalkyl, substituted or unsubstituted $C_{1-20}$ alkylene-$C_{3-20}$ heterocyclyl, substituted or unsubstituted $C_{1-20}$ alkylene-O—$C_{3-20}$ heterocyclyl, substituted or unsubstituted aryl, substituted or unsubstituted $C_{3-20}$ heteroaryl, substituted or unsubstituted $C_{3-25}$ cycloalkyl or substituted or unsubstituted $C_{3-20}$ heterocyclyl wherein said $C_{1-20}$ alkyl and $C_{1-20}$ alkylene are optionally interrupted by N(R'), O, S or arylene wherein R' is H, $C_{1-6}$ alkyl or aryl; and $R^{Xb}$ and $R^{Xc}$, which are the same or different, are independently selected from H, unsubstituted or substituted $C_{1-10}$ alkyl and unsubstituted or substituted aryl;

or a pharmaceutically acceptable salt thereof.

Alternatively, the inhibitor of sphingolipid biosynthesis is RNA.

Accordingly, the invention further provides a compound which is an inhibitor of sphingolipid biosynthesis for use in the treatment of a disease which has a secondary Niemann-Pick type C disease like cellular phenotype, wherein the inhibitor of sphingolipid biosynthesis is RNA, provided that the disease is other than mucopolysaccharidosis and other than mucolipidosis IV.

BRIEF DESCRIPTION OF THE FIGURES

FIG. 3A shows the total GSL level (HPLC quantified) in wild-type (RA25) and NPC1 null (CT43) CHO cells treated with or without 50 μM NB-DGJ for 5 days prior to harvesting for GSL analysis by HPLC. FIG. 3B shows micrographs of wild-type (i, iii) and NPC1 null (ii, iv) CHO cells which were treated with (iii, iv) or without (i, ii) 50 μM NB-DGJ for 5 days prior to pulse/chase analysis of BODIPY-LacCer transport (45 min pulse, 1 h chase); reduction in GSL storage with NB-DGJ led to a correction in abnormal BODIPY-LacCer endocytic transport from the punctate late endosomal/lysosomal system (ii) back to the perinuclear Golgi (iv). n=4.

FIG. 5A consists of micrographs showing control, lathosterolosis (Sc5d$^{-/-}$), desmosterolosis (DHCR24$^{-/-}$), and SLOS (DHCR7$^{-/-}$) MEFs, which were grown in medium with 10% FCS for 7 days (top panels) or 10% LPDS (to deplete extracellular derived cholesterol) for 7 days (lower panels). FIG. 5B is a graph of the total uptake of the fluid phase marker HRP (y-axis) for control, DHCR7$^{-/-}$ and DHCR24$^{-/-}$ MEFs (x axis), which were incubated with 3 mg/ml HRP for 2 h at 37° C.

FIG. 6A consists of representative HPLC traces of GSLs from SLOS cells grown in FCS (red trace) or LPDS (green trace); and FIG. 6B gives the total GSL levels for control, SLOS (DHCR7$^{-/-}$) and desmosterolosis (DHCR24$^{-/-}$) cells grown in FCS or LPDS.

DETAILED DESCRIPTION OF THE INVENTION

Figure 1:
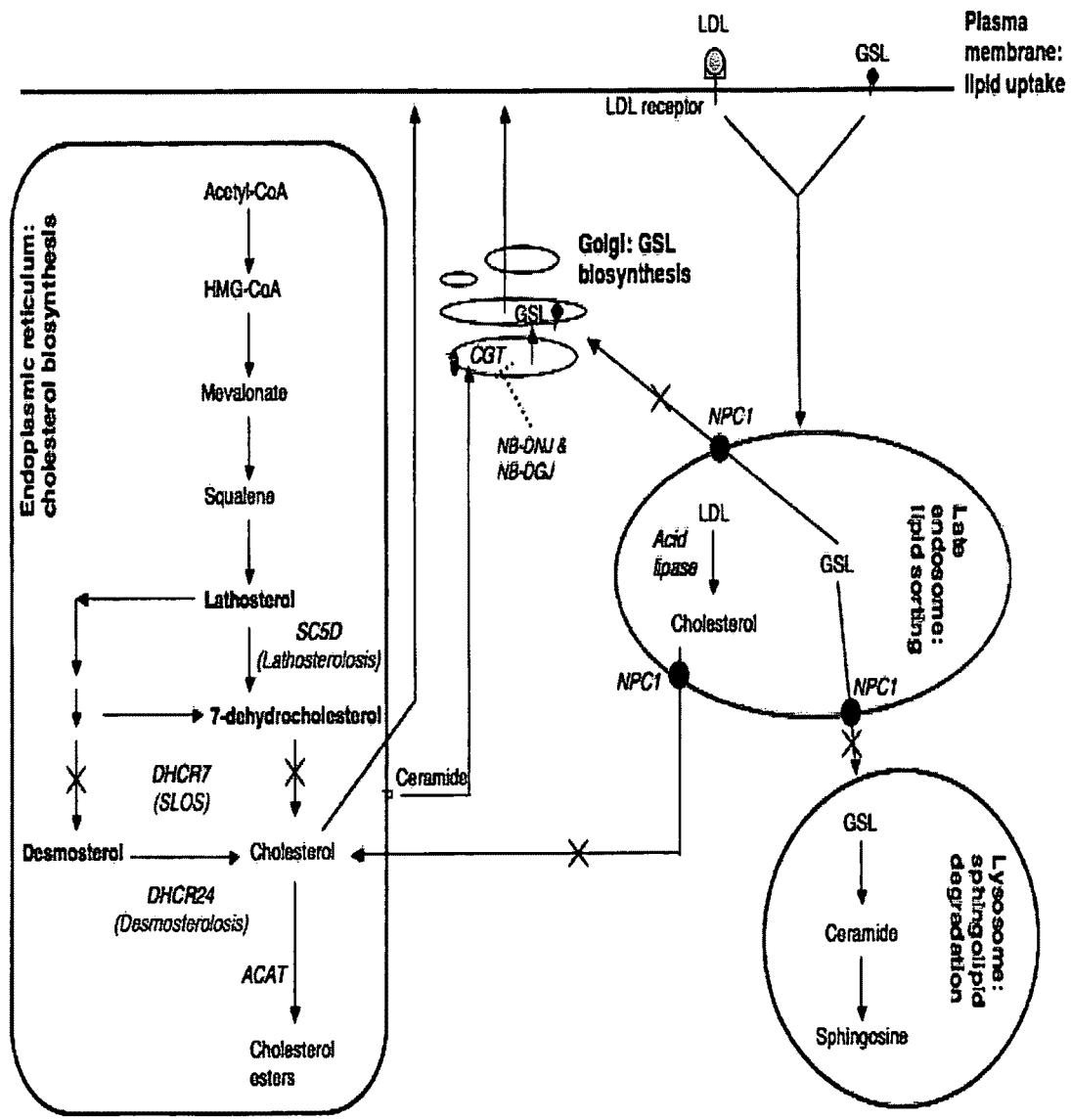
FIG. 1 is a schematic diagram of the sites and mechanisms of cellular lipid synthesis, degradation, and transport. Cholesterol can be de novo synthesized at the ER or alternatively liberated via the action of acid lipase at the late endosome from LDL particles that are internalized via endocytosis of LDL-receptors at the plasma membrane. Genetic mutations in cholesterol biosynthetic enzymes in the ER (italics) will lead to accumulation of the precursor molecule (bold) and a failure to synthesize de novo cholesterol leading to disease. In SLOS the accumulation of 7-DHC leads to inhibition of lipid transport from the late endosome (crosses) potentially via inhibition of NPC1 function (circles) leading to a failure in cholesterol transport to the ER. NPC1 is involved in the transport of glycosphingolipids, GSLs, synthesised at the Golgi (a process inhibited by inhibitors of sphingolipid biosynthesis), out of late endosomes.

The term "inhibitor of sphingolipid biosynthesis", as used herein, means a compound that is capable of inhibiting the synthesis or expression of a sphingolipid.

Typically, the sphingolipid is a glycosphingolipid (GSL). More typically, the sphingolipid is a ganglioside. Alternatively, the sphingolipid is a neutral GSL.

Inhibitors of sphingolipid biosynthesis are either known or readily identifiable, without undue experimentation, using known procedures.

GSLs are synthesized from ceramide by the sequential addition of monosaccharides mediated by Golgi-resident glycosyltransferases. The two main classes of GSL are the neutral GSLs (lacto and globo series) and the gangliosides. Gangliosides contain sialic acid (neuraminic acid) and are consequently negatively charged. The majority of GSLs are glucose derivatives of ceramide. However, galactose based GSLs are also present and are particularly abundant in the CNS. Such galactose-based GSLs include the sulfatides.

There are several classes of compounds which can affect the metabolism of sphingolipids, including compounds of formulae (I), (II), (III), (IV), (V), (IX), (XII) defined above. Some of these compounds (notably, NB-DNJ) have found use in the treatment of congenital disorders of glycolipid storage (such as type I Gaucher disease, reviewed in Aerts J M et al. J. Inherit Metab. Dis. (2006) 29(2-3): 449-453), or as potential anti-microbial agents (for example to modulate the toxicity of cholera toxin to ganglioside-type glycolipids, reviewed in Svensson M et al. Mol Microbiol. (2003) 47: 453-461).

Defects in GSL catabolism result in a build up of GSLs. Such diseases are termed GSL storage disorders. Small-molecule inhibitors such as the alkyl-iminosugars have been developed to inhibit the biosynthesis of glucosylceramide, the first step in the biosynthesis of GSLs. Such compounds are thus inhibitors of sphingolipid biosynthesis which may be employed in the present invention. Glucosylceramide is synthesised by the action of glucosylceramide synthase (also known as UDP-glucose: N-acylsphingosine glucosyltransferase), which catalyses the transfer of glucose to ceramide. The inhibition of glucosylceramide synthase can be achieved in vivo by small-molecule inhibitors (Reviewed in Asano N. Glycobiology (2003) 13:93-104). Inhibition can be achieved by small-molecule mimics of the substrate, transition state or product of glucosylceramide synthase. Broadly, three classes of inhibitors can be deduced: (1) mimics of the carbohydrate moiety ("sugar mimics"), (2) mimics of the ceramide or sphingosine moiety ("lipid mimics") and (3) mimics of the nucleotide moiety of the sugar-nucleotide substrate of the glycosyltransferase ("nucleotide mimics"). Many inhibitors exhibit properties of more than one class. For example, inhibitors can exhibit properties of both (1) and (2) (e.g. Alkylated-DNJ, and AMP-DNJ, discussed below).

The sugar mimics (1) have received considerable attention and include iminosugars such as nojirimycin, N-butyldeoxynojirimycin (NB-DNJ) and N-butyldeoxygalactonojirimycin (NB-DGJ) (see U.S. Pat. No. 5,472,969; U.S. Pat. No. 5,656,641; U.S. Pat. No. 6,465,488; U.S. Pat. No. 6,610,703; U.S. Pat. No. 6,291,657; U.S. Pat. No. 5,580,884; Platt F, J. Biol. Chem. (1994) 269:8362-8365; Platt F M et al. Phil. Trans. R. Soc. Lond. B (2003) 358:947-954; and Butters T D et al. Glycobiology (2005) 15:43-52). The modification of the iminosugar core with an alkyl chain such as a butyl group (as in NB-DNJ) or a nonyl group (as in NN-DNJ) are important for the clinical applications. Further sugar derivatives include N-(5-adamantane-1-yl-methoxypentyl)-DNJ (AMP-DNJ) (Overkleeft et al. J. Biol. Chem. (1998) 41:26522-26527), α-homogalactonojirimycin (HGJ) (Martin et al. 1995 Tetrahedron Letters 36:10101-10116), α-homoallonojirimycin (HAJ) (Asano et al. 1997 J. Nat. Prod. 60:98-101, Martin et al 1999 Bioorg. Med. Chem. Lett 9:3171-3174) and β-1-C-butyl-DGJ (CB-DGJ) (Ikeda et al 2000 Carbohydrate Res. 323:73-80). NB-DNJ results in measurable decrease in GSL levels within a day of treatment with the effect on GSL levels stabilizing after 10 days of treatment in mice (Platt F M J. Biol. Chem. (1997) August 1; 272(31):19365-72.). Critically, both NB-DNJ and NB-DGJ penetrate the CNS without significant effects on behaviour or CNS development, and treatment of adult mice with NB-DNJ or NB-DGJ has been shown not to cause neurological side effects (U. Andersson et al., Neurobiology of Disease, 16 (2004) 506-515). NB-DGJ resulted in a marked reduction in total ganglioside and GM1 content in cerebrum-brainstem (Kasperzyk et al. J. Lipid Res. (2005) 46:744-751).

Lipid mimics (2) have been developed to inhibit sphingolipid biosynthesis (Abe A. et al. J. Biochem Tokyo (1992) 111:191-196. Reviewed in Asano N. Glycobiology (2003) 13:93-104). Ceramide-based inhibitors include D,L-threo-1-phenyl-2-decanoylamino-3-morpholino-1-propanol (PDMP) and D,L-threo-1-phenyl-2-hexadecanoylamino-3-morpholino-1-propanol (PPMP). Numerous derivatives have subsequently been developed such as: D-threo-1-phenyl-2-palmitoilamino-3-pyrrolidino-1-propanol (P4), 4'-hydroxy-P4 (pOH-P4) and 3',4'-ethylenedioxy-P4 (EtDO-P4; Genz-78132, Genzyme). L-DMDP (Yu C Y et al. Chem Commun (Camb). 2004 Sep. 7; (17):1936-7). Small-molecule inhibitors of galactosyltransferases have also been developed and are described in Chung S J, Bioorg Med Chem Lett. 1998 Dec. 1; 8(23):3359-64.

Sphingolipid biosynthesis can also be disrupted by the use of small molecule inhibitors of the glycosidases, glycosyltransferases and other enzymes such as transferases and synthases, that act upstream or downstream of glucosylceramide synthase or galactosylceramide synthase. Such inhibitors are capable of inhibiting the synthesis of a sphingolipid and are therefore inhibitors of sphingolipid biosynthesis which may be employed in the present invention.

Inhibitors of the glycosidases and glycosyltransferases that act downstream of the glucosylceramide synthase or galactosylceramide synthase may be employed in the present invention. For example in the biosynthesis of sialic acid containing sphingolipids, the gangliosides can be downregulated by the use of inhibitors of the sialyltransferases. Example compounds include sialic acid (N-acetylneuraminic acid), lithocholic acid analogues which potently inhibit α2-3-sialyltransferase (Chang K H et al. Chem Commun (Camb). 2006 Feb. 14; (6):629-31), cytidin-5'-yl sialylethylphosphonate which inhibits rat recombinant α-2,3- and α-2,6-ST (IC(50)=0.047, 0.34 mM (Izumi M J Org Chem. 2005 Oct. 28; 70(22):8817-24), and Soyasaponin I, a potent and specific sialyltransferase inhibitor (Wu C Y Biochem Biophys Res Commun. 2001 Jun. 8; 284(2):466-9). Furthermore, some carbohydrates are modified by the addition or removal of chemical groups from the glycan backbone. For example sulfatides are formed by the action of sulfotransferase on carbohydrate moiety of glycolipids. These enzymes are themselves targets for the reduction of sphingolipids.

Accordingly, in one embodiment of the invention the inhibitor of sphingolipid biosynthesis is an inhibitor of a glycosyltransferase. Typically, the inhibitor mimics the substrate, transition state or product of the glycosyltransferase. In particular, the inhibitor may be a compound that mimics the carbohydrate moiety of the substrate, transition state or product of the glycosyltransferase. Alternatively, the inhibitor is a compound that mimics the lipid moiety of the substrate, transition state or product of the glycosyltransferase. Alternatively, the inhibitor is a compound that mimics the nucleotide moiety of the sugar-nucleotide substrate or transition state of the glycosyltransferase. Typically, the glycosyltransferase is a glucosyltransferase. The glucosyltransferase is, for instance, glucosylceramide synthase. Alternatively, the glycosyltransferase may be a galactosyltransferase. The galactosyltransferase may be, for instance, β1-4 galactosyltransferase. Alternatively, the glycosyltransferase may be a ceramide galactosyltransferase. The ceramide galactosyltransferase may be, for instance, UDP-galactose:ceramide galactosyltransferase (also known as galactosylceramide synthase). Alternatively, the glycosyltransferase is a sialyltransferase.

In principle, all glycosyltransferases can be inhibited by substrate mimics (Chung S J, Bioorg Med Chem Lett. 1998 Dec. 1; 8(23):3359-64). Such substrate mimics can be employed for use in the present invention as inhibitors of sphingolipid biosynthesis.

Further examples of inhibitors of sphingolipid biosynthesis include inhibitors of sulfotransferase, fucosyltransferase, or N-acetylhexosaminetransferase. Thus in one embodiment of the present invention, the inhibitor of sphingolipid biosynthesis is an inhibitor of a sulfotransferase. In another embodiment of the present invention, the inhibitor of sphingolipid biosynthesis is an inhibitor of a fucosyltransferase. In another embodiment of the present invention, the inhibitor of sphingolipid biosynthesis is an inhibitor of an N-acetylhexosaminetransferase. Sulfotransferase inhibitors are described in Armstrong, J. I. et al. *Angew. Chem. Int. Ed.* 2000, 39, No. 7, 1303-1306 and references therein. Examples of sulfotransferase inhibitors are given in Table 3 below. In one embodiment, the inhibitor of sphingolipid biosynthesis is an inhibitor of a glycosyltransferase or a sulfotransferase. Fucosyltransferase inhibitors are described in Qiao, L. et al., J. Am. Chem. Soc. 1996, 118, 7653-7662. An example of a fucosyltransferase inhibitor is propyl 2-acetamido-2-deoxy-4-O-(β-D-galactopyranosyl)-3-O-(2-(N-(β-L-homofuconojirimycinyl))ethyl)-α-D-glucopyranoside, which is an azatrisaccharide compound. Qiao, L. et al. found that compound, in the presence of guanosine diphosphate (GDP), to be an effective inhibitor of human α-1,3-fucosyltransferase V. In addition, Wong, C-H, Pure & Appl. Chem., Vol. 67, No. 10, pp 1609-1616 describes the synergistic inhibition of α-1,3-fucosyltransferase using an azasugar and GDP. Azasugar compounds (such as those of formula I herein) can be employed for use in the present invention as inhibitors of sphingolipid biosynthesis. Such azasugar compounds can be used as inhibitors of sphingolipid biosynthesis either alone or in combination with a nucleotide mimic compound, for instance in combination with GDP or a compound of formula III herein. N-acetylhexosaminetransferase inhibitors are described in Schäfer et al., J. Org. Chem. 2000, 65, 24-29. Compounds 58a to 58c and 59a to 59c in Table 2 below are examples of N-acetylhexosaminetransferase inhibitors.

Sphingolipid biosynthesis can be disrupted by the use of inhibitors of enzymes, such as transferases and synthases, that act upstream of glucosylceramide synthase or galactosylceramide synthase. Such inhibitors are termed "inhibitors of ceramide biosynthesis". Inhibitors of ceramide biosynthesis are capable of inhibiting the synthesis of a sphingolipid and are therefore inhibitors of sphingolipid biosynthesis which may be employed in the present invention.

Figure 2:
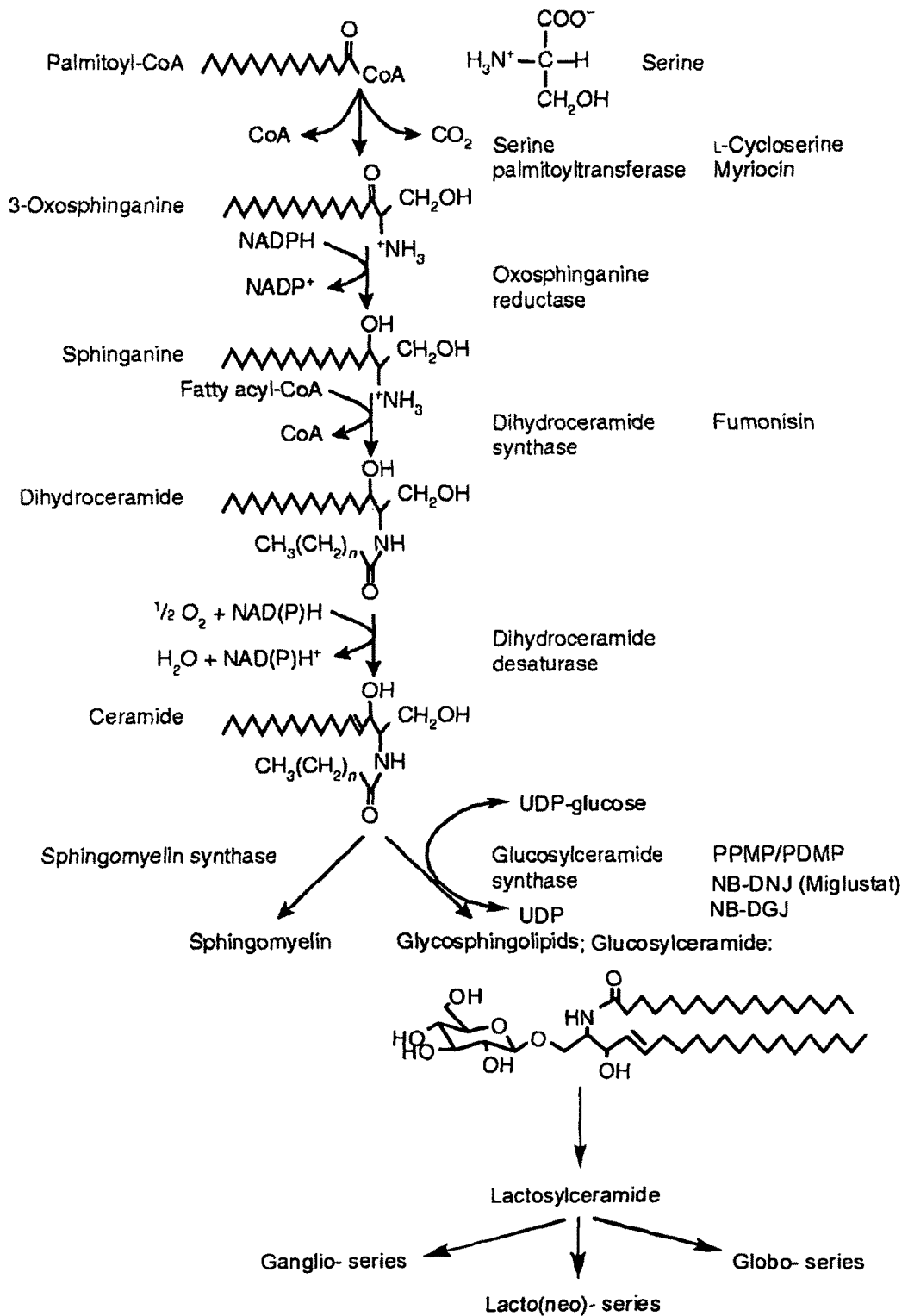
FIG. 2 is a schematic diagram of sphingolipid biosynthesis, indicating the actions of the inhibitor compounds NB-DNJ; NB-DGJ; PDMP (D,L-threo-1-phenyl-2-decanoylamino-3-morpholino-1-propanol); PPMP (D,L-threo-1-phenyl-2-hexadecanoylamino-3-morpholino-1-propanol); fumonisin; myriocin; and L-cycloserine.

Enzymes which act upstream of glucosylceramide synthase include serine palmitoyltransferase and dihydroceramide synthase. Inhibitors of serine palmitoyltransferase include L-Cycloserine and Myriocin. Inhibitors of dihydroceramide synthase include Fumonisin. These particular enzymes and inhibitors of ceramide biosynthesis are indicated in the schematic diagram of sphingolipid biosynthesis in FIG. 2.

In one embodiment, the inhibitor of sphingolipid biosynthesis is an inhibitor of ceramide biosynthesis. Typically, the inhibitor of sphingolipid biosynthesis is an inhibitor of serine palmitoyltransferase or an inhibitor of dihydroceramide synthase. More typically, in this embodiment, the inhibitor of sphingolipid biosynthesis is L-Cycloserine, Myriocin or Fumonisin.

In one embodiment, the inhibitor of sphingolipid biosynthesis is an inhibitor of ceramide degradation. The skilled person can readily identify inhibitors of ceramide degradation without undue experimentation, using known procedures (see for instance J. Med. Chem. 2008, 51, 219-237 and Bioorg. Med. Chem., 9 (2001) 2901-2904, which describe the identification of sphingomyelinase inhibitor compounds, and Bioorg. Med. Chem., 16 (2008) 1032-1045 which describes the identification of ceramidase inhibitors). Typically, the inhibitor of sphingolipid biosynthesis is a ceramidase inhibitor, for instance an inhibitor of acidceramidase.

The skilled person can readily identify inhibitors of sphingolipid biosynthesis without undue experimentation, using known procedures. For instance, inhibitors of sphingolipid biosynthesis can be identified by incubating and or growing cells in culture in the presence of the putative inhibitor together with an assay for the effect of sphingolipid biosynthesis. Such assays include the analysis of fluorescently-labelled glycosphingolipid carbohydrate headgroups by HPLC, thin-layer chromatography (TLC) of sphingolipids and analysis of sphingolipids using mass spectrometry (Neville D C, Anal. Biochem. 2004 Aug. 15; 331(2):275-82; Mellor H R Biochem. J. 2004 Aug. 1; 381(Pt 3):861-6; Hayashi Y. et al., Anal. Biochem. 2005 Oct. 15; 345(2):181-6; Sandhoff, R. et al., J. Biol. Chem., vol. 277, no. 23, 20386-20398, 2002; Sandhoff, R. et al., J. Biol. Chem., vol. 280, no. 29, 27310-27318, 2005; Platt, F. M. et al., J. Biol. Chem., vol. 269, issue 11, 8362-8365, 1994; Platt, F. M. et al., J. Biol. Chem., vol. 269, issue 43, 27108-27114, 1994).

Neville D C et al. (Anal. Biochem. 2004 Aug. 15; 331(2): 275-82) have developed an optimised assay method in which fluorescently labelled glycosphingolipid-derived oligosaccharides are analysed. Thus, inhibitors of sphingolipid biosynthesis for use in accordance with the present invention can be identified by incubating or growing cells in culture, in the presence of the putative inhibitor, and applying the assay described in Neville et al. The assay described in Neville et al. enables GSL levels to be measured by HPLC analysis of GSL-derived oligosaccharides following ceramide glycanase digestion of the GSLs and anthranilic acid labelling of the released oligosaccharides. In the assay, glycosphingolipids (GSLs) are extracted from the sample and purified by column chromatography. The extracted GSLs are then digested with ceramide glycanase. The extracted GSLs are first dried and redissolved, with mixing in 10 µl incubation buffer (50 µM sodium acetate, pH 5.0, containing 1 mg/ml sodium cholate or sodium taurodeoxycholate). To this is added, with gentle mixing, 0.05 U ceramide glycanase in a further 10 µl incubation buffer (giving a final concentration of 2.5 U/ml). One unit (U) is defined as the amount of enzyme that will hydrolyze 1.0 nmol of ganglioside, GM1, per minute at 37° C. Incubations are performed at 37° C. for 18 hours. The ceramide-glycanase-released oligosaccharides are then labelled with anthranilic acid and purified essentially as described in Anumula and Dhume, Glycobiology 8 (1998) 685-694 with the modifications described in Neville D C et al. Anal. Biochem. 2004 Aug. 15; 331(2):275-82. The purified 2-AA-labelled oligosaccharides are then separated by normal phase HPLC, as described in Neville D C et al., and glucose unit values are determined following comparison with a 2-AA-labelled glucose oligomer ladder (derived from a partial hydrolysate of dextran) external standard. Inhibitors of sphingolipid biosynthesis are identified by measuring the decrease in GSL levels observed in the presence of the inhibitor. A similar assay method is described in Mellor H R Biochem. J. 2004 Aug. 1; 381(Pt 3):861-6. That document describes the synthesis of a series of DNJ analogues to study their inhibitory activity in cultured HL60 cells. When the cells are treated for 16 hours at non-cytotoxic concentrations of DNJ analogue, a 40-50% decrease in GSL levels can be observed by HPLC analysis of GSL-derived oligosaccharides following ceramide glycanase digestion of GSL and 2-aminobenzamide labelling of the released oligosaccharides.

Hayashi Y. et al., Anal. Biochem. 2005 Oct. 15; 345(2): 181-6 reports an HPLC-based method that uses fluorescent acceptors and nonradioisotope UDP-sugar donors to provide a fast, sensitive and reproducible assay to determine glucosylceramide synthase (GlcT) and lactosylceramide synthase (GalT) activities. Thus, inhibitors of sphingolipid biosynthesis for use in accordance with the present invention can be identified by incubating and or growing cells in culture in the presence of the putative inhibitor, and applying the assay method described in Hayashi et al. The HPLC-based assay procedures described in Hayashi et al. involve mixing a fluorescent acceptor substrate, either 50 pmol of C6-NBD-Cer or C6-NBD-GlcCer, and 6.5 nmol of lecithin in 100 μmol of ethanol, and then evaporating the solvent. Next 10 μl of water is added and the mixture is sonicated to form liposomes. For the GlcT assay, 50 μl of reaction mixture contains 500 μM UDP-Glc, 1 mM EDTA, 10 μl C6-NBD-Cer liposome and 20 μl of an appropriate amount of enzyme in lysis buffer 1. For the GalT assay, 50 μl of mixture contains 100 μM UDP-Gal, 5 mM $MgCl_2$, 5 mM $MnCl_2$, 10 μl C6-NBD-GlcCer liposome, and 20 μl of an appropriate amount of enzyme in lysis buffer 2. The assays are carried out at 37° C. for 1 hour. The reaction is stopped by adding 200 μl of chloroform/methanol (2:1, v/v). After a few seconds of vortexing, 5 μl of 500 μM KCl is added and then centrifuged. After the organic phase has dried up, lipids are dissolved in 200 μl of isopropyl alcohol/n-hexane/$H_2O$ (55:44:1) and then transferred to a glass vial in an autosampler. A 100 μl aliquot sample is then loaded onto a normal-phase column and eluted with isopropyl alcohol/n-hexane/$H_2O$ (55:44:1) for the GlcT assay or isopropyl alcohol/n-hexane/$H_2O$/phosphoric acid (110:84:5.9:0.1) for the GalT assay at a flow rate of 2.0 ml/min. Fluorescence can be determined using a fluorescent detector set to excitation and emission wavelengths of 470 and 530 nm, respectively. Fluorescent peaks are identified by comparing their retention times with those of standards.

Further assays include fluorescent-activated cells sorting (FACS) with glycosphingolipid-binding proteins such as anti-glycosphingolipid antibodies or lectins (see for example Rouquette-Jazdanian et al., The Journal of Immunology, 2005, 175: 5637-5648 and Chefalo, P et al., Biochemistry 2006, Mar. 21; 45(11): 3733-9).

Sandhoff et al. (J. Biol. Chem., vol. 277, no. 23, 20386-20398, 2002 and J. Biol. Chem., vol. 280, no. 29, 27310-27318, 2005) describe assay methods in which sphingolipid are analysed by mass spectrometry or by TLC. Inhibitors of sphingolipid biosynthesis for use in accordance with the present invention can be identified by incubating and or growing cells in culture in the presence of the putative inhibitor, and applying the TLC assay method or mass spectrometry assay method described by Sandhoff et al. Further details of these methods are given below.

In the methods described by Sandhoff et al. (J. Biol. Chem., vol. 277, no. 23, 20386-20398, 2002 and J. Biol. Chem., vol. 280, no. 29, 27310-27318, 2005) the glycosphingolipid profiles in mice were measured by nano-electrospray ionization tandem mass spectrometry (nano-ESI-MS/MS). Glycosphingolipids were first extracted from murine tissue for mass spectrometric analysis. The samples prepared included both the extracted GSLs and synthesised GSL MS standards. Nano-ESI-MS/MS analyses were performed with a triple quadropole instrument equipped with a nano-electrospray source operating at an estimated flow rate of 20-50 nl/min. Usually 10 μL of sample, dissolved in methanol or methanolic ammonium acetate (5 mM), was filled into a gold-sputtered capillary, which was positioned at a distance of 1-3 mm in front of the cone. The source temperature was set to 30° C. and the spray was started by applying 800-1200 V to the capillary. For each spectrum 20-50 scans of 15-30 s duration were averaged. The resulting Nano-ESI-MS/MS data could then be evaluated for quantification of the GSLs as follows: Quantitative spectra were measured with an average mass resolution of 1200 (ion mass/full width half maximum). Peak height values of the first mono-isotopic peak of each compound were taken for evaluation. A linear trend was calculated from the peak intensities of the corresponding internal standard lipids. The obtained calibration curve represented the intensity of the internal standard amount at a given m/z value. The quantities of the individual species of a GSL were calculated using a corrected intensity ratio (sample GSL/internal standard trend), knowing the amount of the internal standard added. The amount of the GSL was then calculated from the sum of the individual molecular species.

Sandhoff et al. (J. Biol. Chem., vol. 277, no. 23, 20386-20398, 2002 and J. Biol. Chem., vol. 280, no. 29, 27310-27318, 2005) also describe a procedure for analysing GSLs using TLC. Glycosphingolipids were extracted from murine tissue for analysis by TLC. Neutral and acidic GSL fractions were each taken up in 100 μL chloroform/methanol/water (10:10:1). Aliquots were then spotted on TLC plates with a Linomat IV from CAMAG (Muttenz, C H). A pre-run was performed with chloroform/alcohol (1:1). The plates were then dried and the GSLs were separated with the running solvent chloroform, methanol, 0.2% aqueous $CaCl_2$ (60:35:8). GSL bands were detected with orcinol/sulphuric acid spray reagent at 110° C. for 10 to 20 mins and the GSLs were identified by comparison with GSL standards.

TLC assays for analysing sphingolipid biosynthesis are also described in Platt, F. M. et al., J. Biol. Chem., vol. 269, issue 11, 8362-8365 and 1994; Platt, F. M. et al., J. Biol. Chem., vol. 269, issue 43, 27108-27114, 1994.

In another embodiment, the inhibitor of sphingolipid biosynthesis is Ribonucleic acid (RNA). RNA can be used to reduce ("knock down") expression of a target enzyme which is involved in sphingolipid biosynthesis, such as a transferase enzyme, in order to achieve the same result as a small molecule inhibitor of that enzyme. The transferase enzyme may be a glycosyltransferase, for instance. Typically, the transferase enzyme is a glucosyltransferase, sialyltransferase, galactosyltransferase, ceramide galactosyltransferase, sulfotransferase, fucosyltransferase, or an N-acetylhexosaminetransferase. In one embodiment, the transferase enzyme is a galactosyltransferase, for instance α-1,3-galactosyltransferase. Typically the RNA is antisense RNA or siRNA (small interfering RNA).

The skilled person can readily identify RNA inhibitors of sphingolipid biosynthesis without undue experimentation, using known procedures. By considering the coding sequence of a particular target enzyme which is involved in sphingolipid biosynthesis, the skilled person is able to design RNA, for instance antisense RNA or siRNA, that is able to reduce ("knock down") expression of that enzyme (see, for example, Huesken, D. et al. (2005) Design of a genome-wide siRNA library using an artificial neural network. Nat. Biotechnol. 23, 995).

Zhu, M. et al., *Transplantation* 2005; 79: 289-296 describes the use of siRNA to reduce expression of the galactosyltransferase enzyme α-1,3-galactosyltransferase and, consequently, reduce synthesis of the α-Gal epitope (Galα1-3Galβ1-4GlcNAc-R). In Zhu et al., α-1,3-galactosyltransferase-specific siRNA was transfected into the porcine aortic endothelial cell line, PED. α-Gal expression was assessed by Western blotting, flow cytometric analyses (FACS) and immunofluorescence. RNA interference was successfully achieved in PED cells as shown by the specific knock-down of α1,3 galactosyltransferase mRNA levels. Flow cytometric analysis using the *Griffonia simplicifolia* isolectin B4 lectin confirmed the suppression of α-1,3-galactosyltransferase activity, as evidenced by decreased α-Gal.

The siRNA duplexes used by Zhu et al. were synthesised by in vitro transcription with T7 RNA polymerase and obtained readily annealed (Genesil, Wuhan, China). The duplexes were designed by considering the various isoforms of α-1,3-galactosyltransferase, termed α1,3GT isoforms 1, 2, 3, 4 and 5 respectively. These isoforms are a result of the alternative splicing of exons 5, 6 and 7 of α-1,3-galactosyltransferase. Porcine endothelial cells express isoforms 1, 2 and 4 only. The catalytic domain of α-1,3-galactosyltransferase is encoded by exons 7, 8 and 9. Thus, in order to avoid missing certain splice variants, and to efficaciously knock-down the expression of the α-1,3-galactosyltransferase mRNA translating the three PED isoforms simultaneously, two siRNA duplexes were synthesised that were specific for the α-1,3-galactosyltransferase mRNA sequence located in exons 7 and 9 as the target of siRNA. The siRNA duplex specific for the α-1,3-galactosyltransferase mRNA sequence located in exon 7 was termed "siRNA-1", and the siRNA duplex specific for the α-1,3-galactosyltransferase mRNA sequence located in exon 9 was termed "siRNA-2". Zhu et al. found siRNA-1 to be effective in reducing α-1,3-galactosyltransferase mRNA expression. The siRNA-1 sequence is from position +199 to +217 relative to the start codon of the porcine α-1,3-galactosyltransferase coding sequence (Genbank Accession No. AF221508). The sequence of the siRNA-1 duplex is as follows:

```
sense:       5'-GAAGAAGACGCUAUAGGCAdTdT-3'
antisense:   5'-UGCCUAUAGCGUCUUCUUCdTdT-3'
```

According to Zhu, M. et al., FACS analysis and immunofluorescent assay indicated that the transfection with siRNA-1 led to a dramatic decrease in binding of fluorescein isothiocyanate-conjugated *Griffonia simplicifolia* isolectin B4 (FITC-GS-IB4) to the α-Gal epitope as compared with parental PED, indicating that decreased α-Gal expression had occurred. Western Blot analysis further confirmed the α-1,3-galactosyltransferase RNA interference effect on the synthesis of Glycoproteins which have the α-Gal residue.

The following definitions apply to the compounds of formulae (I), (II), (III), (IV), (V), (IX) and (XII):

A $C_{1-20}$ alkyl group is an unsubstituted or substituted, straight or branched chain saturated hydrocarbon radical. Typically it is $C_{1-10}$ alkyl, for example methyl, ethyl, propyl, butyl, pentyl, hexyl, heptyl, octyl, nonyl or decyl, or $C_{1-6}$ alkyl, for example methyl, ethyl, propyl, butyl, pentyl or hexyl, or $C_{1-4}$ alkyl, for example methyl, ethyl, i-propyl, n-propyl, t-butyl, s-butyl or n-butyl. When an alkyl group is substituted it typically bears one or more substituents selected from substituted or unsubstituted $C_{1-20}$ alkyl, substituted or unsubstituted aryl (as defined herein), cyano, amino, $C_{1-10}$ alkylamino, alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. Examples of substituted alkyl groups include haloalkyl, hydroxyalkyl, aminoalkyl, alkoxyalkyl and alkaryl groups. The term alkaryl, as used herein, pertains to a $C_{1-20}$ alkyl group in which at least one hydrogen atom has been replaced with an aryl group. Examples of such groups include, but are not limited to, benzyl (phenylmethyl, $PhCH_2$—), benzhydryl ($Ph_2CH$—), trityl (triphenylmethyl, $Ph_3C$—), phenethyl (phenylethyl, Ph-$CH_2CH_2$—), styryl (Ph-CH=CH—), cinnamyl (Ph-CH=CH—$CH_2$—).

Typically a substituted $C_{1-20}$ alkyl group carries 1, 2 or 3 substituents, for instance 1 or 2.

A $C_{3-25}$ cycloalkyl group is an unsubstituted or substituted alkyl group which is also a cyclyl group; that is, a monovalent moiety obtained by removing a hydrogen atom from an alicyclic ring atom of a carbocyclic ring of a carbocyclic compound, which moiety has from 3 to 25 carbon atoms (unless otherwise specified), including from 3 to 25 ring atoms. Thus, the term "cycloalkyl" includes the sub-classes cycloalkyenyl and cycloalkynyl. Examples of groups of $C_{3-25}$ cycloalkyl groups include $C_{3-20}$ cycloalkyl, $C_{3-15}$ cycloalkyl, $C_{3-10}$ cycloalkyl, $C_{3-7}$ cycloalkyl. When a $C_{3-25}$ cycloalkyl group is substituted it typically bears one or more substituents selected from $C_{1-6}$ alkyl which is unsubstituted, aryl (as defined herein), cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, phosphoric acid, phosphate ester, phosphonic acid and phosphonate ester and sulfonyl. Typically a substituted $C_{3-25}$ cycloalkyl group carries 1, 2 or 3 substituents, for instance 1 or 2.

Examples of $C_{3-25}$ cycloalkyl groups include, but are not limited to, those derived from saturated monocyclic hydrocarbon compounds, which $C_{3-25}$ cycloalkyl groups are unsubstituted or substituted as defined above:

cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$);

unsaturated monocyclic hydrocarbon compounds:
cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$);

saturated polycyclic hydrocarbon compounds:
thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$);

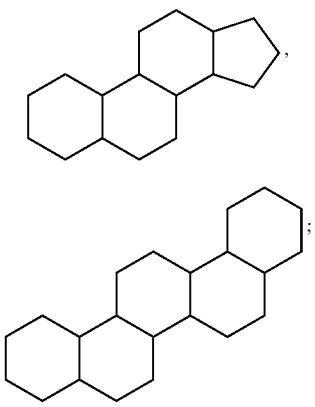

($C_{17}$)

($C_{22}$)

unsaturated polycyclic hydrocarbon compounds: camphene ($C_{10}$), limonene ($C_{10}$), pinene ($C_{10}$),

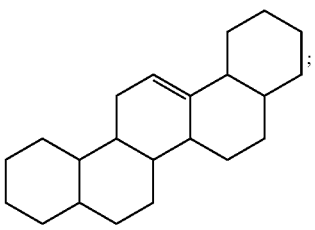

($C_{22}$)

polycyclic hydrocarbon compounds having an aromatic ring:

indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

A $C_{3-20}$ heterocyclyl group is an unsubstituted or substituted monovalent moiety obtained by removing a hydrogen atom from a ring atom of a heterocyclic compound, which moiety has from 3 to 20 ring atoms (unless otherwise specified), of which from 1 to 10 are ring heteroatoms. Preferably, each ring has from 3 to 7 ring atoms, of which from 1 to 4 are ring heteroatoms. When a $C_{3-20}$ heterocyclyl group is substituted it typically bears one or more substituents selected from $C_{1-6}$ alkyl which is unsubstituted, aryl (as defined herein), cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, phosphoric acid, phosphate ester, phosphonic acid and phosphonate ester and sulfonyl. Typically a substituted $C_{3-20}$ heterocyclyl group carries 1, 2 or 3 substituents, for instance 1 or 2.

Examples of groups of heterocyclyl groups include $C_{3-20}$heterocyclyl, $C_{5-20}$heterocyclyl, $C_{3-15}$heterocyclyl, $C_{5-15}$heterocyclyl, $C_{3-12}$heterocyclyl, $C_{5-12}$heterocyclyl, $C_{3-10}$heterocyclyl, $C_{5-10}$heterocyclyl, $C_{3-7}$heterocyclyl, $C_{5-7}$heterocyclyl, and $C_{5-6}$heterocyclyl.

Examples of (non-aromatic) monocyclic $C_{3-20}$ heterocyclyl groups include, but are not limited to, those derived from:

$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);

$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);

$S_1$: thiirane ($C_3$), thietane ($C_4$), thiolane (tetrahydrothiophene) ($C_5$), thiane (tetrahydrothiopyran) ($C_6$), thiepane ($C_7$);

$O_2$: dioxolane ($C_5$), dioxane ($C_6$), and dioxepane ($C_7$);

$O_3$: trioxane ($C_6$);

$N_2$: imidazolidine ($C_5$), pyrazolidine (diazolidine) ($C_5$), imidazoline ($C_5$), pyrazoline (dihydropyrazole) ($C_5$), piperazine ($C_6$);

$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);

$N_1S_1$: thiazoline ($C_5$), thiazolidine ($C_5$), thiomorpholine ($C_6$);

$N_2O_1$: oxadiazine ($C_6$);

$O_1S_1$: oxathiole ($C_5$) and oxathiane (thioxane) ($C_6$); and, $N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose. $C_{3-20}$ heterocyclyl includes groups derived from heterocyclic compounds of the following structure:

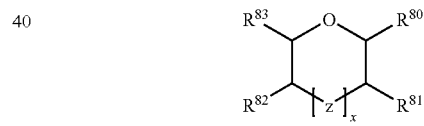

wherein x is 0 or 1; z is $CHR^{84}$; and $R^{80}$, $R^{81}$, $R^{82}$, $R^{83}$ and $R^{84}$, which are the same or different, are independently selected from H, $C_{1-6}$ alkyl, OH, acyloxy, SH, $C_{1-6}$ alkoxy, aryloxy, amino, $C_{1-10}$ alkylamino, di($C_{1-10}$)alkylamino, amido, acylamido and a group derived from a second group of the following structure:

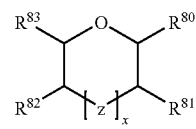

in which second group x is 0 or 1; z is $CHR^{84}$; and $R^{80}$, $R^{81}$, $R^{82}$, $R^{83}$ and $R^{84}$, which are the same or different, are independently selected from H, $C_{1-6}$ alkyl, OH, acyloxy, SH, $C_{1-6}$ alkoxy, aryloxy, amino, $C_{1-10}$ alkylamino, di($C_{1-10}$)alkylamino, amido and acylamido. The term "group derived from" in this case means that the group is a monovalent moiety obtained by removing the $R^{80}$, $R^{81}$, $R^{82}$, $R^{83}$ or $R^{84}$ atom from a carbon atom of the above compounds. Thus, $C_{3-20}$ heterocyclyl includes groups of the following structure:

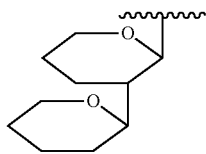 [SMILES: *C1OCCCC1C1CCCCO1]

wherein each of the ring carbon atoms is independently unsubstituted or substituted with $C_{1-6}$ alkyl, OH, acyloxy, SH, $C_{1-6}$ alkoxy, aryloxy, amino, $C_{1-10}$ alkylamino, di($C_{1-10}$)alkylamino, amido and acylamido.

$C_{3-20}$ heterocyclyl also includes groups in which two heterocyclic rings are linked by an oxygen atom. Thus, $C_{3-20}$ heterocyclyl includes disaccharide groups, in which two monosaccharide heterocyclic rings are linked with an oxygen atom. Accordingly, $C_{3-20}$ heterocyclyl includes groups of the following formula (m):

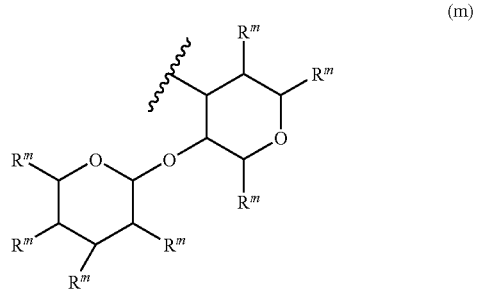

(m)

wherein each $R^m$, which is the same or different, is independently selected from $C_{1-6}$ alkyl, OH, acyloxy, SH, $C_{1-6}$ alkoxy, aryloxy, amino, $C_{1-10}$ alkylamino, di($C_{1-10}$)alkylamino, amido and acylamido. Thus, the following disaccharide group is one example of a substituted $C_{3-20}$ heterocyclic group:

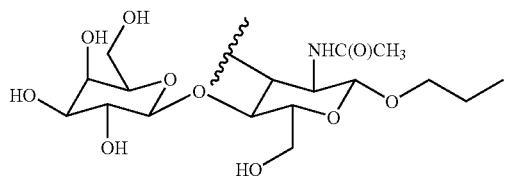

Examples of $C_{3-20}$ heterocyclyl groups which are also aryl groups are described below as heteroaryl groups.

An aryl group is a substituted or unsubstituted, monocyclic or bicyclic aromatic group which typically contains from 6 to 14 carbon atoms, preferably from 6 to 10 carbon atoms in the ring portion. Examples include phenyl, naphthyl, indenyl and indanyl groups. An aryl group is unsubstituted or substituted. When an aryl group as defined above is substituted it typically bears one or more substituents selected from $C_1$-$C_6$ alkyl which is unsubstituted (to form an aralkyl group), aryl which is unsubstituted, cyano, amino, $C_{1-10}$ alkylamino, di($C_{1-10}$) alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfhydryl (i.e. thiol, —SH), $C_{1-10}$ alkylthio, arylthio, sulfonic acid, phosphoric acid, phosphate ester, phosphonic acid and phosphonate ester and sulfonyl. Typically it carries 0, 1, 2 or 3 substituents. A substituted aryl group may be substituted in two positions with a single $C_{1-6}$ alkylene group, or with a bidentate group represented by the formula —X—$C_{1-6}$ alkylene, or —X—$C_{1-6}$ alkylene-X—, wherein X is selected from O, S and NR, and wherein R is H, aryl or $C_{1-6}$ alkyl. Thus a substituted aryl group may be an aryl group fused with a cycloalkyl group or with a heterocyclyl group. The term aralkyl as used herein, pertains to an aryl group in which at least one hydrogen atom (e.g., 1, 2, 3) has been substituted with a $C_{1-6}$ alkyl group. Examples of such groups include, but are not limited to, tolyl (from toluene), xylyl (from xylene), mesityl (from mesitylene), and cumenyl (or cumyl, from cumene), and duryl (from durene). The ring atoms of an aryl group may include one or more heteroatoms (as in a heteroaryl group). Such an aryl group (a heteroaryl group) is a substituted or unsubstituted mono- or bicyclic heteroaromatic group which typically contains from 6 to 10 atoms in the ring portion including one or more heteroatoms. It is generally a 5- or 6-membered ring, containing at least one heteroatom selected from O, S, N, P, Se and Si. It may contain, for example, 1, 2 or 3 heteroatoms. Examples of heteroaryl groups include pyridyl, pyrazinyl, pyrimidinyl, pyridazinyl, furanyl, thienyl, pyrazolidinyl, pyrrolyl, oxazolyl, oxadiazolyl, isoxazolyl, thiadiazolyl, thiazolyl, isothiazolyl, imidazolyl, pyrazolyl, quinolyl and isoquinolyl. A heteroaryl group may be unsubstituted or substituted, for instance, as specified above for aryl. Typically it carries 0, 1, 2 or 3 substituents.

A $C_{1-20}$ alkylene group is an unsubstituted or substituted bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below. Typically it is $C_{1-10}$ alkylene, for instance $C_{1-6}$ alkylene. Typically it is $C_{1-4}$ alkylene, for example methylene, ethylene, i-propylene, n-propylene, t-butylene, s-butylene or n-butylene. It may also be pentylene, hexylene, heptylene, octylene and the various branched chain isomers thereof. An alkylene group may be unsubstituted or substituted, for instance, as specified above for alkyl. Typically a substituted alkylene group carries 1, 2 or 3 substituents, for instance 1 or 2.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkylene," as used herein, pertains to an alkylene group having from 1 to 4 carbon atoms. Examples of groups of alkylene groups include $C_{1-4}$ alkylene ("lower alkylene"), $C_{1-7}$ alkylene, $C_{1-10}$ alkylene and $C_{1-20}$ alkylene.

Examples of linear saturated $C_{1-7}$ alkylene groups include, but are not limited to, —$(CH_2)_n$— where n is an integer from 1 to 7, for example, —$CH_2$— (methylene), —$CH_2CH_2$— (ethylene), —$CH_2CH_2CH_2$— (propylene), and —$CH_2CH_2CH_2CH_2$— (butylene).

Examples of branched saturated $C_{1-7}$ alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{1-7}$ alkylene groups include, but is not limited to, —CH=CH— (vinylene), —CH=CH—$CH_2$—, —$CH_2$—CH=$CH_2$—, —CH=CH—$CH_2$—$CH_2$—, —CH=CH—$CH_2$—$CH_2$—

$CH_2$—, —CH=CH—CH=CH—, —CH=CH—CH=CH—$CH_2$—, —CH=CH—CH=CH—$CH_2$—$CH_2$—, —CH=CH—$CH_2$—CH=CH—, and —CH=CH—$CH_2$—$CH_2$—CH=CH—.

Examples of branched partially unsaturated $C_{1-7}$ alkylene groups include, but is not limited to, —C($CH_3$)=CH—, —C($CH_3$)=CH—$CH_2$—, and —CH=CH—CH($CH_3$)—.

Examples of alicyclic saturated $C_{1-7}$ alkylene groups include, but are not limited to, cyclopentylene (e.g., cyclopent-1,3-ylene), and cyclohexylene (e.g., cyclohex-1,4-ylene).

Examples of alicyclic partially unsaturated $C_{1-7}$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

$C_{1-20}$ alkylene and $C_{1-20}$ alkyl groups as defined herein are either uninterrupted or interrupted by one or more heteroatoms or heterogroups, such as S, O or N(R") wherein R" is H, $C_{1-6}$ alkyl or aryl (typically phenyl), or by one or more arylene (typically phenylene) groups. The phrase "optionally interrupted" as used herein thus refers to a $C_{1-20}$ alkyl group or an alkylene group, as defined above, which is uninterrupted or which is interrupted between adjacent carbon atoms by a heteroatom such as oxygen or sulfur, by a heterogroup such as N(R") wherein R" is H, aryl or $C_1$-$C_6$ alkyl, or by an arylene group. For instance, a $C_{1-20}$ alkyl group such as n-butyl may be interrupted by the heterogroup N(R") as follows: —$CH_2$N(R")$CH_2$$CH_2$$CH_3$, —$CH_2$$CH_2$N(R")$CH_2$$CH_3$, or —$CH_2$$CH_2$$CH_2$N(R")$CH_3$. Similarly, an alkylene group such as n-butylene may be interrupted by the heterogroup N(R") as follows: —$CH_2$N(R")$CH_2$$CH_2$$CH_2$—, —$CH_2$$CH_2$N(R")$CH_2$$CH_2$—, or —$CH_2$$CH_2$$CH_2$N(R")$CH_2$—. Typically an interrupted group, for instance an interrupted $C_{1-20}$ alkylene or $C_{1-20}$ alkyl group, is interrupted by 1, 2 or 3 heteroatoms or heterogroups or by 1, 2 or 3 arylene (typically phenylene) groups. More typically, an interrupted group, for instance an interrupted $C_{1-20}$ alkylene or $C_{1-20}$ alkyl group, is interrupted by 1 or 2 heteroatoms or heterogroups or by 1 or 2 arylene (typically phenylene) groups. For instance, a $C_{1-20}$ alkyl group such as n-butyl may be interrupted by 2 heterogroups N(R") as follows: —$CH_2$N(R")$CH_2$N(R")$CH_2$$CH_3$.

An arylene group is an unsubstituted or substituted bidentate moiety obtained by removing two hydrogen atoms, one from each of two different aromatic ring atoms of an aromatic compound, which moiety has from 5 to 14 ring atoms (unless otherwise specified). Typically, each ring has from 5 to 7 or from 5 to 6 ring atoms. An arylene group may be unsubstituted or substituted, for instance, as specified above for aryl.

In this context, the prefixes (e.g., $C_{5-20}$, $C_{6-20}$, $C_{5-14}$, $C_{5-7}$, $C_{5-6}$, etc.) denote the number of ring atoms, or range of number of ring atoms, whether carbon atoms or heteroatoms. For example, the term "$C_{5-6}$ arylene," as used herein, pertains to an arylene group having 5 or 6 ring atoms. Examples of groups of arylene groups include $C_{5-20}$ arylene, $C_{6-20}$ arylene, $C_{5-14}$ arylene, $C_{6-14}$ arylene, $C_{6-10}$ arylene, $C_{5-12}$ arylene, $C_{5-10}$ arylene, $C_{5-7}$ arylene, $C_{5-6}$ arylene, $C_5$ arylene, and $C_6$ arylene.

The ring atoms may be all carbon atoms, as in "carboarylene groups" (e.g., $C_{6-20}$ carboarylene, $C_{6-14}$ carboarylene or $C_{6-10}$ carboarylene).

Examples of $C_{6-20}$ arylene groups which do not have ring heteroatoms (i.e., $C_{6-20}$ carboarylene groups) include, but are not limited to, those derived from the compounds discussed above in regard to aryl groups, e.g. phenylene, and also include those derived from aryl groups which are bonded together, e.g. phenylene-phenylene (diphenylene) and phenylene-phenylene-phenylene (triphenylene).

Alternatively, the ring atoms may include one or more heteroatoms, as in "heteroarylene groups" (e.g., $C_{5-10}$ heteroarylene).

Examples of $C_{5-10}$ heteroarylene groups include, but are not limited to, those derived from the compounds discussed above in regard to heteroaryl groups.

As used herein the term oxo represents a group of formula: =O

As used herein the term acyl represents a group of formula: —C(=O)R, wherein R is an acyl substituent, for example, a substituted or unsubstituted $C_{1-20}$ alkyl group, a substituted or unsubstituted $C_{3-20}$ heterocyclyl group, or a substituted or unsubstituted aryl group. Examples of acyl groups include, but are not limited to, —C(=O)$CH_3$ (acetyl), —C(=O)$CH_2$$CH_3$ (propionyl), —C(=O)C($CH_3$)$_3$ (t-butyryl), and —C(=O)Ph (benzoyl, phenone).

As used herein the term acyloxy (or reverse ester) represents a group of formula: —OC(=O)R, wherein R is an acyloxy substituent, for example, substituted or unsubstituted $C_{1-20}$ alkyl group, a substituted or unsubstituted $C_{3-20}$heterocyclyl group, or a substituted or unsubstituted aryl group, typically a $C_{1-6}$ alkyl group. Examples of acyloxy groups include, but are not limited to, —OC(=O)$CH_3$ (acetoxy), —OC(=O)$CH_2$$CH_3$, —OC(=O)C($CH_3$)$_3$, —OC(=O)Ph, and —OC(=O)$CH_2$Ph.

As used herein the term ester (or carboxylate, carboxylic acid ester or oxycarbonyl) represents a group of formula: —C(=O)OR, wherein R is an ester substituent, for example, a substituted or unsubstituted $C_{1-20}$ alkyl group, a substituted or unsubstituted $C_{3-20}$ heterocyclyl group, or a substituted or unsubstituted aryl group (typically a phenyl group).

Examples of ester groups include, but are not limited to, —C(=O)O$CH_3$, —C(=O)O$CH_2$$CH_3$, —C(=O)OC($CH_3$)$_3$, and —C(=O)OPh.

As used herein the term phosphonic acid represents a group of the formula: —P(=O)(OH)$_2$. As would be understood by the skilled person, a phosphonic acid group can exist in protonated and deprotonated forms (i.e. —P(=O)(OH)$_2$, —P(=O)(O$^-$)$_2$ and —P(=O)(OH)(O$^-$)) all of which are within the scope of the term "phosphonic acid".

As used herein the term phosphonic acid salt represents a group which is a salt of a phosphonic acid group. For example a phosphonic acid salt may be a group of the formula —P(=O)(OH)(O$^-$X$^+$) wherein X is a monovalent cation. X$^+$ may be an alkali metal cation. X$^+$ may be Na$^+$ or K$^+$, for example.

As used herein the term phosphonate ester represents a group of one of the formulae: —P(=O)(OR)$_2$ and —P(=O)(OR)O$^-$ wherein each R is independently a phosphonate ester substituent, for example, —H, substituted or unsubstituted $C_{1-20}$ alkyl, substituted or unsubstituted $C_{3-20}$ heterocyclyl, $C_{3-20}$ heterocyclyl substituted with a further $C_{3-20}$ heterocyclyl, substituted or unsubstituted $C_{1-20}$ alkylene-$C_{3-20}$ heterocyclyl, substituted or unsubstituted $C_{3-25}$ cycloalkyl, substituted or unsubstituted $C_{1-20}$ alkylene-$C_{3-25}$ cycloalkyl, aryl, substituted or unsubstituted $C_{1-20}$ alkylene-aryl. Examples of phosphonate ester groups include, but are not limited to, —P(=O)(O$CH_3$)$_2$, —P(=O)(O$CH_2$$CH_3$)$_2$, —P(=O)(O-t-Bu)$_2$, and —P(=O)(OPh)$_2$, As used herein the term phosphoric acid represents a group of the formula: —OP(=O)(OH)$_2$.

As used herein the term phosphate ester represents a group of one of the formulae: —OP(=O)(OR)$_2$ and —OP(=O)(OR)O$^-$ wherein each R is independently a phosphate ester substituent, for example, —H, substituted or unsubstituted $C_{1-20}$ alkyl, substituted or unsubstituted $C_{3-20}$ heterocyclyl, $C_{3-20}$ heterocyclyl substituted with a further $C_{3-20}$ heterocyclyl, substituted or unsubstituted $C_{1-20}$ alkylene-$C_{3-20}$ heterocyclyl, substituted or unsubstituted $C_{3-25}$ cycloalkyl, substituted or unsubstituted $C_{1-20}$ alkylene-$C_{3-25}$ cycloalkyl, aryl, substituted or unsubstituted $C_{1-20}$ alkylene-aryl. Examples of phosphate ester groups include, but are not limited to, —OP(=O)(OCH$_3$)$_2$, —OP(=O)(OCH$_2$CH$_3$)$_2$, —OP(=O)(O-t-Bu)$_2$, and —OP(=O)(OPh)$_2$.

As used herein the term amino represents a group of formula —NH$_2$. The term $C_1$-$C_{10}$ alkylamino represents a group of formula —NHR' wherein R' is a $C_{1-10}$ alkyl group, preferably a $C_{1-6}$ alkyl group, as defined previously. The term di($C_{1-10}$)alkylamino represents a group of formula —NR'R" wherein R' and R" are the same or different and represent $C_{1-10}$ alkyl groups, preferably $C_{1-6}$ alkyl groups, as defined previously. The term arylamino represents a group of formula —NHR' wherein R' is an aryl group, preferably a phenyl group, as defined previously. The term diarylamino represents a group of formula —NR'R" wherein R' and R" are the same or different and represent aryl groups, preferably phenyl groups, as defined previously. The term arylalkylamino represents a group of formula —NR'R" wherein R' is a $C_{1-10}$ alkyl group, preferably a $C_{1-6}$ alkyl group, and R" is an aryl group, preferably a phenyl group.

As used herein the term amido represents a group of formula: —C(=O)NR'R", wherein R' and R" are independently amino substituents, as defined for di($C_{1-10}$)alkylamino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R' and R", together with the nitrogen atom to which they are attached, form a heterocyclic structure as in, for example, piperidinocarbonyl, morpholinocarbonyl, thiomorpholinocarbonyl, and piperazinocarbonyl.

As used herein the term acylamido represents a group of formula: —NR$^1$C(=O)R$^2$, wherein R$^1$ is an amide substituent, for example, hydrogen, a $C_{1-20}$alkyl group, a $C_{3-20}$ heterocyclyl group, an aryl group, preferably hydrogen or a $C_{1-20}$ alkyl group, and R$^2$ is an acyl substituent, for example, a $C_{1-20}$ alkyl group, a $C_{3-20}$ heterocyclyl group, or an aryl group, preferably hydrogen or a $C_{1-20}$ alkyl group. Examples of acylamide groups include, but are not limited to, —NHC(=O)CH$_3$, —NHC(=O)CH$_2$CH$_3$, —NHC(=O)Ph, —NHC(=O)C$_{15}$H$_{31}$ and —NHC(=O)C$_9$H$_{19}$. Thus, a substituted $C_{1-20}$ alkyl group may comprise an acylamido substituent defined by the formula —NHC(=O)—$C_{1-20}$ alkyl, such as —NHC(=O)C$_{15}$H$_{31}$ or —NHC(=O)C$_9$H$_{19}$. R$^1$ and R$^2$ may together form a cyclic structure, as in, for example, succinimidyl, maleimidyl, and phthalimidyl:

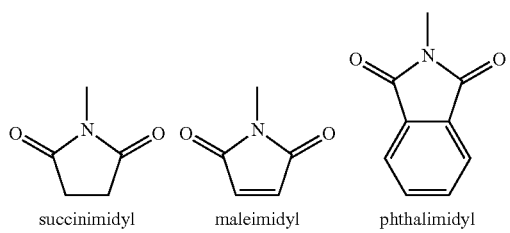

succinimidyl    maleimidyl    phthalimidyl

A $C_{1-10}$ alkylthio group is a said $C_{1-10}$ alkyl group, preferably a $C_{1-6}$ alkyl group, attached to a thio group. An arylthio group is an aryl group, preferably a phenyl group, attached to a thio group.

A $C_{1-20}$ alkoxy group is a said substituted or unsubstituted $C_{1-20}$ alkyl group attached to an oxygen atom. A $C_{1-6}$ alkoxy group is a said substituted or unsubstituted $C_{1-6}$ alkyl group attached to an oxygen atom. A $C_{1-4}$ alkoxy group is a substituted or unsubstituted $C_{1-4}$ alkyl group attached to an oxygen atom. Said $C_{1-20}$, $C_{1-6}$ and $C_{1-4}$ alkyl groups are optionally interrupted as defined herein. Examples of $C_{1-4}$ alkoxy groups include, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy). Further examples of $C_{1-20}$ alkoxy groups are —O(Adamantyl), —O—CH$_2$-Adamantyl and —O—CH$_2$—CH$_2$-Adamantyl. A further example of a $C_{1-20}$ alkoxy group is —O—($C_{1-9}$ alkylene)-O—CH$_2$-Adamantyl. This includes, for instance, —O—(CH$_2$)$_5$—O—CH$_2$-Adamantyl. An aryloxy group is a substituted or unsubstituted aryl group, as defined herein, attached to an oxygen atom. An example of an aryloxy group is —OPh (phenoxy).

Unless otherwise specified, included in the above are the well known ionic, salt, solvate, and protected forms of these substituents. For example, a reference to carboxylic acid or carboxyl group (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Certain compounds may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R—, S—, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto, enol, and enolate forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

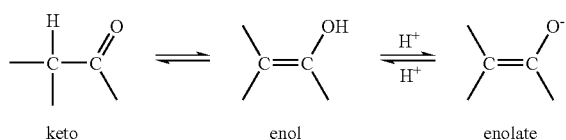

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Unless otherwise specified, a reference to a particular compound includes all such isomeric forms, including (wholly or partially) racemic and other mixtures thereof. Methods for the preparation (e.g., asymmetric synthesis) and separation (e.g., fractional crystallisation and chromatographic means) of such isomeric forms are either known in the art or are readily obtained by adapting known methods, in a known manner.

Unless otherwise specified, a reference to a particular compound also includes ionic, salt, solvate, protected forms and prodrugs thereof.

Examples of pharmaceutically acceptable salts of the compounds for use in accordance with the present invention include salts with inorganic acids such as hydrochloric acid, hydrobromic acid, hydroiodic acid, sulphuric acid, nitric acid and phosphoric acid; and organic acids such as methanesulfonic acid, benzenesulphonic acid, formic acid, acetic acid, trifluoroacetic acid, propionic acid, butyric acid, isobutyric acid, oxalic acid, malonic acid, succinic acid, fumaric acid, maleic acid, lactic acid, malic acid, tartaric acid, citric acid, ethanesulfonic acid, aspartic acid, benzoic acid and glutamic acid. Typically the salt is a hydrochloride, an acetate, a propionate, a benzoate, a butyrate or an isobutyrate. Examples of pharmaceutically acceptable salts are discussed in Berge et al., 1977, "Pharmaceutically Acceptable Salts," J. Pharm. Sci., Vol. 66, pp. 1-19.

A prodrug of an inhibitor of sphingolipid biosynthesis is a compound which, when metabolised (e.g., in vivo), yields the desired active compound. Typically, the prodrug is inactive, or less active than the active compound, but may provide advantageous handling, administration, or metabolic properties.

For example, some prodrugs are O-acylated (acyloxy) derivatives of the active compound, i.e. physiologically acceptable metabolically labile acylated derivatives. During metabolism, the one or more —O-acyl (acyloxy) groups (—O—C(═O)R$^P$) are cleaved to yield the active drug. R$^P$ may be a C$_{1-10}$ alkyl group, an aryl group or a C$_{3-20}$ cycloalkyl group. Typically, R$^P$ is a C$_{1-10}$ alkyl group including, but not limited to, methyl, ethyl, propyl, butyl, pentyl, hexyl, heptyl, octyl, nonyl and decyl. Such derivatives may be formed by acylation, for example, of any of the hydroxyl groups (—OH) in the parent compound, with, where appropriate, prior protection of any other reactive groups present in the parent compound, followed by deprotection if required. Thus, the free hydroxyl groups on an iminosugar inhibitor of sphingolipid biosynthesis (for instance DNJ, DGJ, or an N-alkylated derivative of DNJ or DGJ such as NB-DNJ or NB-DGJ) may be acylated with up to four, typically exactly four, O-acyl groups. The O-acyl groups are enzymatically removed in vivo to provide the non-O-acylated (i.e. hydroxyl-containing) active inhibitor of sphingolipid biosynthesis.

Some prodrugs are esters of the active compound (e.g., a physiologically acceptable metabolically labile ester). During metabolism, the ester group (—C(═O)OR) is cleaved to yield the active drug. Such esters may be formed by esterification, for example, of any of the carboxylic acid groups (—C(═O)OH) in the parent compound, with, where appropriate, prior protection of any other reactive groups present in the parent compound, followed by deprotection if required.

The compound which is an inhibitor of sphingolipid biosynthesis for use in accordance with the invention can be used in the free form or the salt form. For example, when the compound is an iminosugar such as DNJ, DGJ or an N-alkylated derivative thereof, it can be used in the free amine form or in the salt form. The compound may also be used in prodrug form. The prodrug can itself be used in the free form or the salt form. For example, when the prodrug is an iminosugar such as an O-acylated prodrug of DNJ, DGJ or an N-alkylated derivative thereof, it can be used in the free amine form or in the salt form.

In one embodiment the invention provides a compound for use in the treatment of a disease which has a secondary Niemann-Pick type C disease like cellular phenotype, which compound is an inhibitor of sphingolipid biosynthesis of the following formula (I):

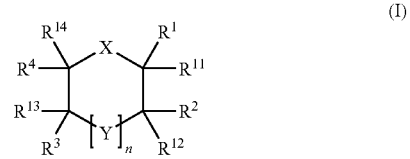

(I)

wherein:

X is O, S or NR$^5$;

R$^5$ is hydrogen, substituted or unsubstituted C$_{1-20}$ alkyl, substituted or unsubstituted C$_{1-20}$ alkylene-aryl, substituted or unsubstituted C$_{1-20}$ alkylene-C$_{3-20}$ heteroaryl, substituted or unsubstituted C$_{1-20}$ alkylene-C$_{3-25}$ cycloalkyl, substituted or unsubstituted C$_{1-20}$ alkylene-C$_{3-20}$ heterocyclyl, substituted or unsubstituted C$_{1-20}$ alkylene-O—C$_{3-20}$ heterocyclyl, substituted or unsubstituted aryl, substituted or unsubstituted C$_{3-20}$ heteroaryl, substituted or unsubstituted C$_{3-25}$ cycloalkyl or substituted or unsubstituted C$_{3-20}$ heterocyclyl, or R$^5$ forms, together with R$^1$, R$^{11}$, R$^4$ or R$^{14}$, a substituted or unsubstituted C$_{1-6}$ alkylene group, wherein said C$_{1-20}$ alkyl and C$_{1-20}$ alkylene are optionally interrupted by N(R'), O, S or arylene wherein R' is H, C$_{1-6}$ alkyl or aryl;

n is 0 or 1;

Y is O, S or CR$^6$R$^{16}$;

R$^1$, R$^{11}$, R$^4$ and R$^{14}$, which may be the same or different, are independently selected from hydrogen, hydroxyl, carboxyl, amino, thiol, substituted or unsubstituted C$_{1-20}$ alkyl, substituted or unsubstituted C$_{1-20}$ alkoxy, substituted or unsubstituted aryloxy, acyl, ester, acyloxy, C$_{1-10}$ alkylamino, di(C$_{1-10}$)alkylamino, amido, acylamido, —O—C$_{3-25}$ cycloalkyl and —O—C$_{3-20}$ heterocyclyl, provided that one of R$^1$, R$^{11}$, R$^4$ and R$^{14}$ may form, together with R$^5$, a substituted or unsubstituted C$_{1-6}$ alkylene group, wherein said C$_{1-20}$ alkyl is optionally interrupted by N(R'), O, S or arylene; and R$^2$, R$^{12}$, R$^3$, R$^{13}$, R$^6$ and R$^{16}$, which may be the same or different, are independently selected from hydrogen, hydroxyl, carboxyl, amino, thiol, substituted or unsubstituted C$_{1-20}$ alkyl, substituted or unsubstituted C$_{1-20}$ alkoxy, substituted or unsubstituted aryloxy, acyl, ester, acyloxy, C$_{1-10}$ alkylamino, di(C$_{1-10}$)alkylamino, amido, acylamido —O—C$_{3-25}$ cycloalkyl and —O—C$_{3-20}$ heterocyclyl, wherein said C$_{1-20}$ alkyl is optionally interrupted by N(R'), O, S or arylene, or a pharmaceutically acceptable salt thereof.

In the compounds of formula (I), typically either $R^1$ or $R^{11}$ (more typically $R^{11}$) is H. Typically, either $R^2$ or $R^{12}$ (more typically $R^{12}$) is H. Typically, either $R^3$ or $R^{13}$ (more typically $R^{13}$) is H. Typically, either $R^4$ or $R^{14}$ (more typically $R^{14}$) is H. Typically, where Y is CR$^6$R$^{16}$, either $R^6$ or $R^{16}$ (more typically $R^{16}$) is H.

Typically, $R^1$ or $R^{11}$ is selected from hydrogen, hydroxyl, carboxyl, substituted or unsubstituted C$_{1-20}$ alkyl, substituted C$_{1-20}$ alkoxy, substituted or unsubstituted aryloxy, —O—C$_{3-25}$ cycloalkyl and —O—C$_{3-20}$ heterocyclyl. More typically, $R^{11}$ is hydrogen and $R^1$ is selected from hydrogen, hydroxyl, carboxyl, substituted or unsubstituted C$_{1-20}$ alkyl, substituted C$_{1-20}$ alkoxy, substituted or unsubstituted aryloxy, —O—C$_{3-25}$ cycloalkyl and —O—C$_{3-20}$ heterocyclyl.

Typically, when $R^1$ or $R^{11}$ is C$_{1-20}$ alkoxy, said C$_{1-20}$ alkoxy group is substituted with an ester group or an aryl group, for instance with —C(O)OCH$_3$ or Ph.

Typically, when $R^1$ or $R^{11}$ is an aryloxy group, the aryl group bonded to the oxygen of said aryloxy is either substituted or unsubstituted phenyl, or substituted or unsubstituted naphthyl. Typically, the phenyl or naphthyl is either unsubstituted or monosubstituted with halo or methoxy.

When $R^1$ or $R^{11}$ is a substituted C$_{1-20}$ alkyl group, the substituent may be a hydroxyl, phosphate ester or phosphonate ester group. For instance, $R^1$ or $R^{11}$ may be CH$_2$OH or a group of the following formula (VII):

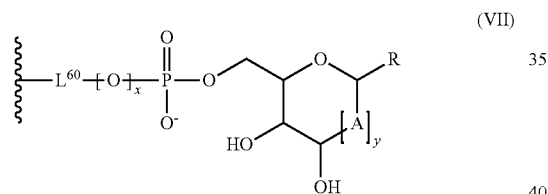

(VII)

wherein L$^{60}$ is substituted or unsubstituted C$_{1-20}$ alkylene; x is 0 or 1; y is 0 or 1; A is CHR''' and R is H, C$_{1-20}$ alkyl, C$_{3-20}$ heterocyclyl, C$_{3-25}$ cycloalkyl, aryl or C$_{1-20}$ alkoxy, wherein R''' is hydroxyl, C$_{1-6}$ alkoxy, aryloxy or acyl. Typically R''' is hydroxyl. Typically R is either —OCH$_3$ or a heterocyclic group of the following structure:

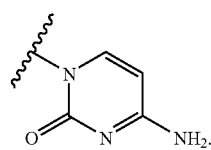

Typically, both $R^1$ and $R^{11}$ are groups of formula (VII) above. An example of a compound in which both $R^1$ and $R^{11}$ are groups of formula (VII) is cytidin-5'-yl sialylethylphosphonate.

Typically, when $R^1$ or $R^{11}$ is unsubstituted C$_{1-20}$ alkyl, it is a methyl, ethyl, propyl, butyl, pentyl, hexyl, heptyl, octyl, nonyl or decyl group.

Typically, when $R^1$ or $R^{11}$ is —O—C$_{3-25}$ cycloalkyl, the cycloalkyl group is a group derived from a compound of one of the following formulae, which compound may be substituted or unsubstituted:

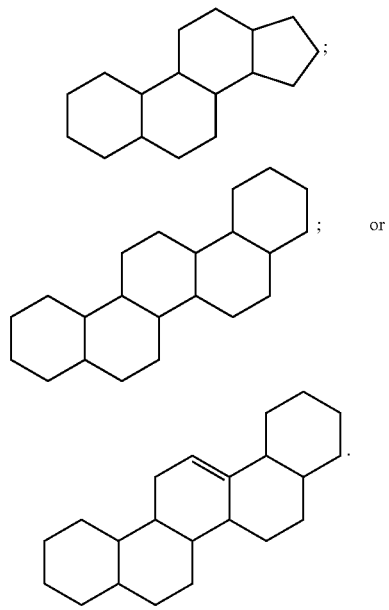

The term "group derived from a compound" in this case means that the group is a monovalent moiety obtained by removing a hydrogen atom from a carbon atom of the compound. An example of a compound in which $R^1$ or $R^{11}$ is —O—C$_{3-25}$ cycloalkyl is Soyasaponin I, in which $R^1$ or $R^{11}$ has the following structure:

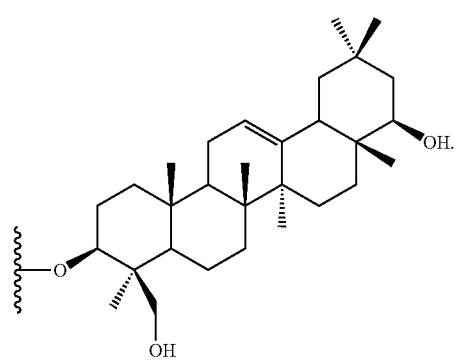

Typically, when $R^1$ or $R^{11}$ is —O—C$_{3-20}$ heterocyclyl, said heterocyclyl group is a group derived from a monosaccharide in cyclic form, for instance a group of the following structure:

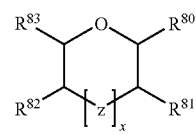

wherein x is 0 or 1; z is CHR$^{84}$; and R$^{80}$, R$^{81}$, R$^{82}$, R$^{83}$ and R$^{84}$, which are the same or different, are independently selected from H, C$_{1-6}$ alkyl, OH, acyloxy, SH, C$_{1-6}$ alkoxy, aryloxy, amino, C$_{1-10}$ alkylamino, di(C$_{1-10}$)alkylamino, amido and acylamido. The term "group derived from" in this case means that the group is a monovalent moiety obtained by removing the R$^{80}$, R$^{81}$, R$^{82}$, R$^{83}$ or R$^{84}$ atom from a carbon atom of the above compound.

More typically, when $R^1$ or $R^{11}$ is —O—$C_{3-20}$ heterocyclyl, said —O—$C_{3-20}$ heterocyclyl group is a group of any one of the following structures:

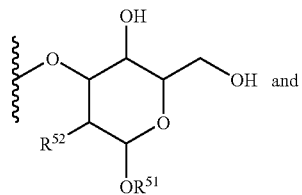

and

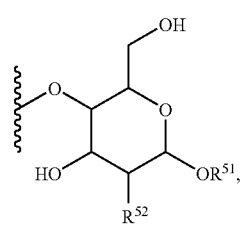

in which $R^{51}$ is a substituted or unsubstituted $C_{1-10}$ alkyl group, typically methyl, or a substituted or unsubstituted aryl group, typically a phenyl or naphthyl group. The phenyl or naphthyl may be unsubstituted or substituted. When substituted, the phenyl or naphthyl is typically substituted with a halo group, for instance with a bromo group. $R^{52}$ is typically hydroxyl, $C_{1-10}$ alkoxy, acyloxy, aryloxy or acylamido. Typically, $R^{52}$ is —OH or —NHC(O)Me.

In the compounds of formula (I), typically either $R^2$ or $R^{12}$ is selected from hydrogen, hydroxyl, acyloxy, acylamido, $C_{1-20}$ alkoxy, $C_{1-20}$ alkyl and —O—$C_{3-20}$ heterocyclyl. More typically, $R^{12}$ is hydrogen and $R^2$ is selected from hydrogen, hydroxyl, acyloxy, $C_{1-20}$ alkoxy, $C_{1-20}$ alkyl and —O—$C_{3-20}$ heterocyclyl.

Typically, when $R^2$ or $R^{12}$ is acylamido, said acylamido is —NHC(O)CH$_3$.

Typically, when $R^2$ or $R^{12}$ is acyloxy, said acyloxy is selected from —OC(O)CH$_3$, —OC(O)CH$_2$CH$_3$, —OC(O)CH$_2$CH$_2$CH$_3$ and —OC(O)CH$_2$CH$_2$CH$_2$CH$_3$. More typically, when $R^2$ or $R^{12}$ is acyloxy, said acyloxy is —OC(O)CH$_2$CH$_2$CH$_3$.

Typically, when $R^2$ or $R^{12}$ is —O—$C_{3-20}$ heterocyclyl, said heterocyclyl group is a group derived from a monosaccharide in cyclic form, for instance a group of the following structure:

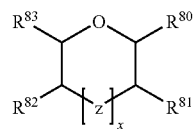

wherein x is 0 or 1; z is CHR$^{84}$; and $R^{80}$, $R^{81}$, $R^{82}$, $R^{83}$ and $R^{84}$, which are the same or different, are independently selected from H, $C_{1-6}$ alkyl, OH, SH, $C_{1-6}$ alkoxy, aryloxy, amino, $C_{1-10}$ alkylamino, di($C_{1-10}$)alkylamino, amido, acylamido and a group derived from a second group of the following structure:

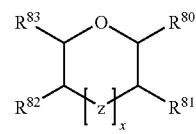

in which second group x is 0 or 1; z is CHR$^{84}$; and $R^{80}$, $R^{81}$, $R^{82}$, $R^{83}$ and $R^{84}$, which are the same or different, are independently selected from H, $C_{1-6}$ alkyl, OH, SH, $C_{1-6}$ alkoxy, aryloxy, amino, $C_{1-10}$ alkylamino, di($C_{1-10}$)alkylamino, amido and acylamido. The term "group derived from" in this case means that the group is a monovalent moiety obtained by removing the $R^{80}$, $R^{81}$, $R^{82}$, $R^{83}$ or $R^{84}$ atom or group from a carbon atom of the compound. Thus when $R^2$ or $R^{12}$ is —O—$C_{3-20}$ heterocyclyl, said heterocyclyl group may be a group of the following structure:

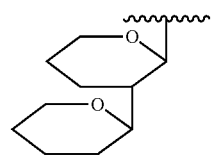

wherein each of the ring carbon atoms is independently unsubstituted or substituted with $C_{1-6}$ alkyl, OH, SH, $C_{1-6}$ alkoxy, aryloxy, amino, $C_{1-10}$ alkylamino, di($C_{1-10}$)alkylamino, amido and acylamido. An example of a compound in which $R^2$ or $R^{12}$ is —O—$C_{3-20}$ heterocyclyl is Soyasaponin I, in which $R^2$ or $R^{12}$ is a group of the following structure:

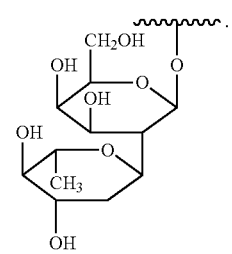

Typically, when $R^2$ or $R^{12}$ is $C_{1-20}$ alkoxy or $C_{1-20}$ alkyl, the group is methyl, ethyl, propyl, butyl, pentyl, hexyl, methoxy, ethoxy, propoxy, butoxy, pentoxy or hexoxy.

More typically, $R^2$ or $R^{12}$ is selected from H, OH, —OC(O)CH$_2$CH$_2$CH$_3$ and NHC(O)CH$_3$. In another embodiment, $R^2$ or $R^{12}$ is selected from H and OH.

In the compounds of formula (I), typically either $R^3$ or $R^{13}$ is selected from hydrogen, hydroxyl, acyloxy, acylamido, $C_{1-20}$ alkoxy and $C_{1-20}$ alkyl. More typically, $R^{13}$ is hydrogen and $R^3$ is selected from hydrogen, hydroxyl, acyloxy, $C_{1-20}$ alkoxy and $C_{1-20}$ alkyl.

Typically, when $R^3$ or $R^{13}$ is acylamido, said acylamido is —NHC(O)CH$_3$.

Typically, when $R^3$ or $R^{13}$ is acyloxy, said acyloxy is selected from —OC(O)CH$_3$, —OC(O)CH$_2$CH$_3$, —OC(O)CH$_2$CH$_2$CH$_3$ and —OC(O)CH$_2$CH$_2$CH$_2$CH$_3$. More typically, when $R^3$ or $R^{13}$ is acyloxy, said acyloxy is —OC(O)CH$_2$CH$_2$CH$_3$.

Typically, when $R^3$ or $R^{13}$ is $C_{1-20}$ alkoxy or $C_{1-20}$ alkyl, the group is methyl, ethyl, propyl, butyl, pentyl, hexyl, methoxy, ethoxy, propoxy, butoxy, pentoxy or hexoxy.

More typically, $R^3$ or $R^{13}$ is selected from H, OH and NHC(O)CH$_3$. In another embodiment, $R^3$ or $R^{13}$ is selected from H and OH.

In the compounds of formula (I), typically either $R^4$ or $R^{14}$ is hydrogen, hydroxyl, acyloxy, carboxyl, ester or $C_{1-20}$ alkyl which is substituted or unsubstituted, or $R^4$ or $R^{14}$ forms, together with $R^5$, a substituted or unsubstituted $C_{1-6}$ alkylene group. More typically, $R^{14}$ is hydrogen and $R^4$ is hydrogen, hydroxyl, acyloxy, carboxyl, ester or $C_{1-20}$ alkyl which is substituted or unsubstituted, or $R^4$ forms, together with $R^5$, a substituted or unsubstituted $C_{1-6}$ alkylene group.

Typically, when $R^4$ or $R^{14}$ is acyloxy, said acyloxy is selected from —OC(O)CH$_3$, —OC(O)CH$_2$CH$_3$, —OC(O)CH$_2$CH$_2$CH$_3$ and —OC(O)CH$_2$CH$_2$CH$_2$CH$_3$.

Typically, when $R^4$ or $R^{14}$ is a $C_{1-20}$ alkyl, said $C_{1-20}$ alkyl is substituted with one, two, three or four groups selected from hydroxyl, acyloxy, thiol and —SC(O)R$^{95}$, wherein R$^{95}$ is $C_{1-6}$ alkyl. More typically, said $C_{1-20}$ alkyl is methyl, ethyl, propyl or butyl substituted with one, two, three or four groups respectively, which groups are selected from hydroxyl, acyloxy and thiol, more typically from hydroxyl and thiol.

Typically, when $R^4$ or $R^{14}$ forms, together with $R^5$, a substituted or unsubstituted $C_{1-6}$ alkylene group, said alkylene group is substituted or unsubstituted propylene. Typically, said propylene is unsubstituted or substituted with a $C_{1-4}$ alkyl group, for instance with a methyl group. Examples of compounds of formula (I) in which $R^4$ or $R^{14}$ forms, together with $R^5$, a methyl-substituted propylene group are Castanospermine and MDL25874, whose structures are given below.

$R^4$ or $R^{14}$ is typically H, —CH$_2$OH, —CH$_2$SH, —CH(OH)CH(OH)CH$_2$OH or —COOH or $R^4$ or $R^{14}$ forms, together with $R^5$, a propylene group substituted with a methyl group.

In the compounds of formula (I), typically n is 1, Y is CR$^6$R$^{16}$ and either $R^6$ or $R^{16}$ is selected from hydrogen, hydroxyl, acyloxy, amino, $C_{1-20}$ alkoxy and $C_{1-20}$ alkyl. More typically, n is 1, Y is CR$^6$R$^{16}$, R$^{16}$ is hydrogen and R$^6$ is selected from hydrogen, hydroxyl, acyloxy, amino, $C_{1-20}$ alkoxy and $C_{1-20}$ alkyl.

Typically, when $R^6$ or $R^{16}$ is acyloxy, said acyloxy is selected from —OC(O)CH$_3$, —OC(O)CH$_2$CH$_3$, —OC(O)CH$_2$CH$_2$CH$_3$ and —OC(O)CH$_2$CH$_2$CH$_2$CH$_3$.

Typically, when $R^6$ or $R^{16}$ is $C_{1-20}$ alkoxy or $C_{1-20}$ alkyl, the group is methyl, ethyl, propyl, butyl, pentyl, hexyl, methoxy, ethoxy, propoxy, butoxy, pentoxy or hexoxy.

Typically, $R^6$ or $R^{16}$ is selected from —OH and —NH$_2$.

Alternatively, n is 1 and Y is O or S. More typically, n is 1 and Y is O.

Alternatively, n is 0.

In the compounds of formula (I), typically $R^5$ is hydrogen, substituted or unsubstituted $C_{1-20}$ alkyl, substituted or unsubstituted $C_{1-20}$ alkylene-aryl, substituted or unsubstituted $C_{1-20}$ alkylene-$C_{3-20}$ heteroaryl, substituted or unsubstituted $C_{1-20}$ alkylene-$C_{3-25}$ cycloalkyl, substituted or unsubstituted $C_{1-20}$ alkylene-$C_{3-20}$ heterocyclyl, substituted or unsubstituted $C_{1-20}$ alkylene-O—$C_{3-20}$ heterocyclyl or $R^5$ forms, together with $R^1$, $R^{11}$, $R^4$ or $R^{14}$, a substituted or unsubstituted $C_{1-6}$ alkylene group, wherein said $C_{1-20}$ alkyl and $C_{1-20}$ alkylene are optionally interrupted by N(R'), O, S or arylene wherein R' is H, $C_{1-6}$ alkyl or aryl.

Typically, when $R^5$ is substituted or unsubstituted $C_{1-20}$ alkylene-$C_{3-25}$ cycloalkyl, $R^5$ is —($C_{1-10}$ alkylene)-O—CH$_2$-Adamantyl. This includes, for instance, —(CH$_2$)$_5$—O—CH$_2$-Adamantyl.

Typically, when $R^5$ is substituted or unsubstituted $C_{1-20}$ alkylene-O—$C_{3-20}$ heterocyclyl, said $C_{1-20}$ alkylene is unsubstituted, and is, for instance, an unsubstituted $C_{1-4}$ alkylene group, for example ethylene. Typically, when $R^5$ is substituted or unsubstituted $C_{1-20}$ alkylene-O—$C_{3-20}$ heterocyclyl, said $C_{3-20}$ heterocyclyl is a group of the following formula (m):

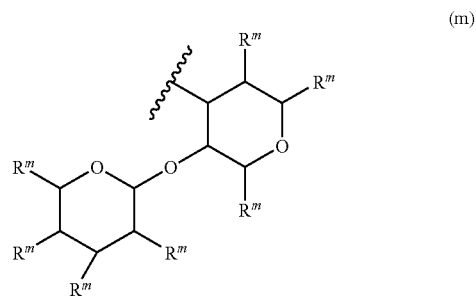

wherein each R$^m$, which is the same or different, is independently selected from $C_{1-6}$ alkyl, OH, acyloxy, SH, $C_{1-6}$ alkoxy, aryloxy, amino, $C_{1-10}$ alkylamino, di($C_{1-10}$)alkylamino, amido and acylamido. More typically, when $R^5$ is substituted or unsubstituted $C_{1-20}$ alkylene-O—$C_{3-20}$ heterocyclyl, said $C_{3-20}$ heterocyclyl is a group of the following structure:

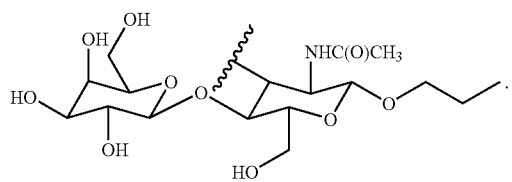

Alternatively, $R^5$ may be substituted or unsubstituted aryl, substituted or unsubstituted $C_{3-20}$ heteroaryl, substituted or unsubstituted $C_{3-20}$ heterocyclyl or substituted or unsubstituted $C_{3-25}$ cycloalkyl. Thus, $R^5$ may be substituted or unsubstituted phenyl or substituted or unsubstituted cyclohexyl, for example.

In the compounds of formula (I), typically X is NR$^5$, and R$^5$ forms, together with $R^4$ or $R^{14}$ (typically $R^4$), a substituted or unsubstituted $C_{1-6}$ alkylene group, or $R^5$ is selected from hydrogen, unsubstituted or substituted $C_{1-20}$ alkyl which is optionally interrupted by O, and a group of the following formula (VIII)

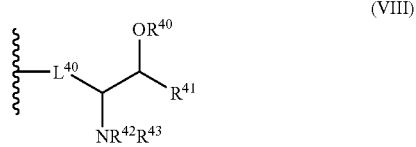

in which:

$R^{40}$ and $R^{42}$, which are the same or different, are independently selected from H, substituted or unsubstituted $C_{1-6}$ alkyl or substituted or unsubstituted phenyl;

$R^{41}$ is H, substituted or unsubstituted aryl, —CH═CHR$^{44}$, or substituted or unsubstituted $C_{1-20}$ alkyl, which $C_{1-20}$ alkyl is optionally interrupted by N(R'), O, S or arylene wherein R' is H, $C_{1-6}$ alkyl or aryl;

$R^{43}$ is H, substituted or unsubstituted $C_{1-6}$ alkyl, substituted or unsubstituted phenyl or —C(O)R$^{47}$;

$R^{44}$ is H or substituted or unsubstituted $C_{1-20}$ alkyl, which $C_{1-20}$ alkyl is optionally interrupted by N(R'), O, S or arylene;

$R^{47}$ is substituted or unsubstituted $C_{1-20}$ alkyl, which $C_{1-20}$ alkyl is optionally interrupted by N(R'), O, S or arylene; and $L^{40}$ is substituted or unsubstituted $C_{1-10}$ alkylene.

Typically, $R^{40}$ is H. Typically, $R^{42}$ is H. Typically, $R^{43}$ is H or —C(O)$R^{47}$. More typically, $R^{43}$ is —C(O)$R^{47}$. Typically, $R^{47}$ is unsubstituted $C_{1-20}$ alkyl. $R^{47}$ may be, for instance, $C_9H_{19}$ or $C_{15}H_{31}$. Typically $L^{40}$ is $CH_2$. In one embodiment, $R^{41}$ is —CH=$CHR^{44}$ and $R^{44}$ is unsubstituted $C_{1-20}$ alkyl. In that embodiment, $R^{44}$ may be, for instance, —$C_{13}H_{27}$. In another embodiment, $R^{41}$ is a group of the following formula (VIIIa):

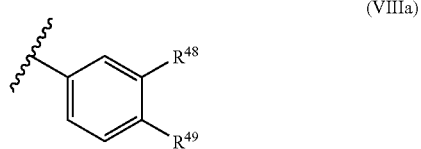

(VIIIa)

in which $R^{48}$ is H, $C_{1-6}$ alkyl, phenyl or, together with $R^{49}$ a bidentate group of the structure —O-alk-O—; $R^{49}$ is H, $C_{1-6}$ alkyl, phenyl or, together with $R^{48}$ a bidentate group of the structure —O-alk-O—, wherein alk is substituted or unsubstituted $C_{1-6}$ alkylene. Typically, $R^{48}$ is H or, together with $R^{49}$ a bidentate group of the structure —O—$CH_2$—$CH_2$—O—. Typically, $R^{49}$ is H, OH or, together with $R^{48}$ a bidentate group of the structure —O—$CH_2$—$CH_2$—O—. Typically, $R^{48}$ is H and $R^{49}$ is either H or OH.

Typically, when $R^5$ is $C_{1-20}$ alkyl optionally interrupted by O, $R^5$ is methyl, ethyl, propyl, butyl, pentyl, hexyl, heptyl, octyl, nonyl, decyl, methyl-O—$R^{90}$, ethyl-O—$R^{90}$, propyl-O—$R^{90}$, butyl-O—$R^{90}$, pentyl-O—$R^{90}$, hexyl-O—$R^{90}$, heptyl-O—$R^{90}$, octyl-O—$R^{90}$, nonyl-O—$R^{90}$ or decyl-O—$R^{90}$ wherein $R^{90}$ is methyl, ethyl, propyl, butyl, pentyl, hexyl, heptyl, octyl, nonyl, decyl or adamantyl.

Typically, when $R^5$ forms, together with $R^4$ or $R^{14}$, a substituted or unsubstituted $C_{1-6}$ alkylene group, the alkylene group is substituted or unsubstituted propylene. Typically, said propylene is unsubstituted or substituted with a $C_{1-4}$ alkyl group, for instance with a methyl group. Examples of compounds of formula (I) in which $R^4$ or $R^{14}$ forms, together with $R^5$, a methyl-substituted propylene group are Castanospermine and MDL25874, whose structures are given below.

Alternatively, X is O or S. More typically, X is O.

Typically, $R^{12}$, $R^{13}$, $R^{14}$ and $R^{16}$ are all H and the inhibitor of sphingolipid biosynthesis is of formula (Ia) below:

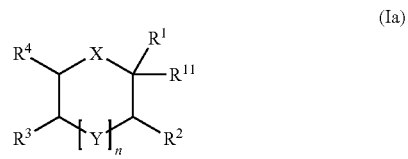

(Ia)

wherein X is O, S or $NR^5$; Y is O, S or $CHR^6$; n is 0 or 1; and $R^1$, $R^2$, $R^3$, $R^4$ $R^5$, $R^6$ and $R^{11}$ are as defined above for formula (I).

In one embodiment, the inhibitor of sphingolipid biosynthesis is of formula (Ia) and: X is $NR^5$; n is 1; Y is $CHR^6$; and $R^5$ is selected from: hydrogen and unsubstituted or substituted $C_{1-20}$ alkyl which is optionally interrupted by O, or $R^5$ forms, together with $R^4$, a substituted or unsubstituted $C_{1-6}$ alkylene group.

Typically in this embodiment, $R^{11}$ is H. Typically in this embodiment, $R^1$, $R^2$, $R^3$ and $R^6$, which may be the same or different, are independently selected from H, OH, acyloxy, and substituted or unsubstituted $C_{1-6}$ alkyl. When said $C_{1-6}$ alkyl is substituted, it is typically substituted with 1, 2, 3 or 4 groups selected from hydroxyl and acyloxy. Typically, in this embodiment, $R^4$ is either $C_{1-6}$ alkyl substituted with 1, 2, 3 or 4 groups selected from hydroxyl and acyloxy, or $R^4$ forms, together with $R^5$, a substituted or unsubstituted $C_{1-6}$ alkylene group. For instance, $R^4$ may be methyl, ethyl, propyl or butyl substituted with 1, 2, 3 or 4 groups respectively, which groups are selected from hydroxyl and acyloxy, more typically hydroxyl. $R^4$ may be $CH_2OH$. Alternatively $R^4$ may be a group which, together with $R^5$, is a substituted or unsubstituted propylene group. Typically, in this embodiment, $R^2$, $R^3$ and $R^6$ are all OH. Typically, in this embodiment $R^1$ is selected from H, OH and $C_{1-6}$ alkyl which is unsubstituted or substituted with one, two, three or four groups selected from hydroxyl and acyloxy. For instance, $R^1$ may be H, OH, unsubstituted $C_{1-6}$ alkyl, methyl, ethyl, propyl or butyl, which methyl, ethyl, propyl and butyl are substituted with 1, 2, 3 or 4 groups respectively, which groups are selected from hydroxyl and acyloxy, more typically hydroxyl. More typically, $R^4$ is H, OH, $CH_2OH$ or $C_{1-6}$ alkyl. In this embodiment, the modification of the iminosugar core with an N-alkyl chain such as a N-butyl group (as in NB-DNJ) or a N-nonyl group (as in NN-DNJ) is believed to be important for clinical applications. Thus, typically in this embodiment $R^5$ is $C_{1-20}$ alkyl which is optionally interrupted by O. For instance, $R^5$ may be methyl, ethyl, propyl, butyl, pentyl, hexyl, heptyl, octyl, nonyl, decyl, methyl-O—$R^{90}$, ethyl-O—$R^{90}$, propyl-O—$R^{90}$, butyl-O—$R^{90}$, pentyl-O—$R^{90}$, hexyl-O—$R^{90}$, heptyl-O—$R^{90}$, octyl-O—$R^{90}$, nonyl-O—$R^{90}$ or decyl-O—$R^{90}$ wherein $R^{90}$ is methyl, ethyl, propyl, butyl, pentyl, hexyl, heptyl, octyl, nonyl, decyl or adamantyl. Alternatively, $R^5$, together with $R^4$ is a substituted or unsubstituted $C_{1-6}$ alkylene group. Typically, the alkylene group is substituted or unsubstituted propylene. Typically, said propylene is unsubstituted or substituted with a $C_{1-4}$ alkyl group, for instance with a methyl group. Alternatively, $R^5$ may be H. Typically, when $R^2$ is acyloxy, said acyloxy is selected from —OC(O)$CH_3$, —OC(O)$CH_2CH_3$, —OC(O)$CH_2CH_2CH_3$ and —OC(O)$CH_2CH_2CH_2CH_3$. More typically, when $R^2$ is acyloxy, said acyloxy is —OC(O)$CH_2CH_2CH_3$. Alternatively, $R^5$ is substituted or unsubstituted $C_{1-20}$ alkylene-O—$C_{3-20}$ heterocyclyl. More typically, $R^5$ is $C_{1-4}$ alkylene-O—$C_{3-20}$ heterocyclyl, wherein said $C_{1-4}$ alkylene is unsubstituted and said $C_{3-20}$ heterocyclyl is a group of the following formula (m):

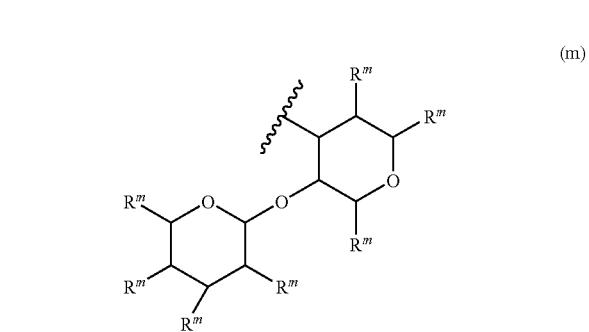

(m)

wherein each $R^m$, which are the same or different, is independently selected from $C_{1-6}$ alkyl, OH, acyloxy, SH, $C_{1-6}$ alkoxy, aryloxy, amino, $C_{1-10}$ alkylamino, di($C_{1-10}$)alkylamino, amido and acylamido. Even more typically, $R^5$ is $C_{1-4}$ alkylene-O—C$_{3-20}$ heterocyclyl, wherein said C$_{1-4}$ alkylene is unsubstituted and said C$_{3-20}$ heterocyclyl is a group of the following structure:

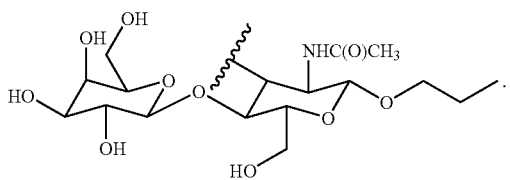

In another embodiment, the inhibitor of sphingolipid biosynthesis is of formula (Ia) and: X is NR$^5$; Y is O or S; n is either 0 or 1; and R$^5$ is selected from hydrogen and a group of the following formula (VIII):

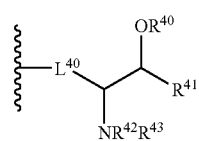

(VIII)

in which R$^{40}$ and R$^{42}$, which are the same or different, are independently selected from H, substituted or unsubstituted C$_{1-6}$ alkyl or substituted or unsubstituted phenyl; R$^{41}$ is H, substituted or unsubstituted aryl, —CH=CHR$^{44}$, or substituted or unsubstituted C$_{1-20}$ alkyl, which C$_{1-20}$ alkyl is optionally interrupted by N(R'), O, S or arylene wherein R' is H, C$_{1-6}$ alkyl or aryl; R$^{43}$ is H, substituted or unsubstituted C$_{1-6}$ alkyl, substituted or unsubstituted phenyl or —C(O)R$^{47}$; R$^{44}$ is H or substituted or unsubstituted C$_{1-20}$ alkyl, which C$_{1-20}$ alkyl is optionally interrupted by N(R'), O, S or arylene; R$^{47}$ is substituted or unsubstituted C$_{1-20}$ alkyl, which C$_{1-20}$ alkyl is optionally interrupted by N(R'), O, S or arylene; and L$^{40}$ is substituted or unsubstituted C$_{1-10}$ alkylene. Typically, R$^{40}$ is H. Typically, R$^{42}$ is H. Typically, R$^{43}$ is H or —C(O)R$^{47}$. More typically, R$^{43}$ is —C(O)R$^{47}$. Typically, R$^{47}$ is unsubstituted C$_{1-20}$ alkyl. R$^{47}$ may be, for instance, C$_9$H$_{19}$ or C$_{15}$H$_{31}$. Typically L$^{40}$ is CH$_2$. In one embodiment, R$^{4I}$ is —CH=CHR$^{44}$ and R$^{44}$ is unsubstituted C$_{1-20}$ alkyl. In that embodiment, R$^{44}$ may be, for instance, —C$_{13}$H$_{27}$. Alternatively, R$^{41}$ is a group of the following formula (VIIIa):

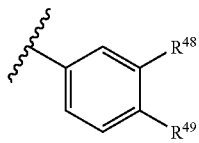

(VIIIa)

in which R$^{48}$ is H, C$_{1-6}$ alkyl, phenyl or, together with R$^{49}$ a bidentate group of the structure —O-alk-O—; R$^{49}$ is H, C$_{1-6}$ alkyl, phenyl or, together with R$^{48}$ a bidentate group of the structure —O-alk-O—, wherein alk is substituted or unsubstituted C$_{1-6}$ alkylene. Typically, R$^{48}$ is H or, together with R$^{49}$ a bidentate group of the structure —O—CH$_2$—CH$_2$—O—. Typically, R$^{49}$ is H, OH or, together with R$^{48}$ a bidentate group of the structure —O—CH$_2$—CH$_2$—O—. Typically, R$^{48}$ is H and R$^{49}$ is either H or OH. Typically in this embodiment, R$^{11}$ is H. Typically in this embodiment, R$^1$, R$^2$, R$^3$, R$^4$ and R$^6$, which may be the same or different, are independently selected from H, OH, acyloxy and C$_{1-6}$ alkyl which is unsubstituted or substituted with one, two, three or four groups selected from hydroxyl and acyloxy. More typically, in this embodiment, R$^1$, R$^2$, R$^3$, R$^4$ and R$^6$ are independently selected from H, OH and CH$_2$OH. Typically, in this embodiment, Y is O. Examples of compounds of this embodiment include D,L-threo-1-phenyl-2-decanoylamino-3-morpholino-1-propanol (PDMP); D,L-threo-1-phenyl-2-hexadecanoylamino-3-morpholino-1-propanol (PPMP); D-threo-1-phenyl-2-palmitoilamino-3-pyrrolidino-1-propanol (P4); 4'-hydroxy-D-threo-1-phenyl-2-palmitoilamino-3-pyrrolidino-1-propanol (4'-hydroxy-P4); 3',4'-ethylenedioxy-P4 (EtDO-P4); and 2,5-dihydroxymethyl-3,4-dihydroxypyrrolidine (L-DMDP).

In another embodiment, the inhibitor of sphingolipid biosynthesis is of formula (Ia) and: X is O or S; n is 1; Y is CHR$^6$; R$^6$ is H, hydroxyl, acyloxy, C$_{1-20}$ alkoxy, C$_{1-10}$ alkylamino or di(C$_{1-10}$)alkylamino; R$^{11}$ is H; R$^2$ and R$^3$, which may be the same or different, are independently selected from H, hydroxyl, C$_{1-20}$ alkoxy, acyloxy or acylamido; R$^4$ is H, hydroxyl, acyloxy, thiol or C$_{1-20}$ alkyl which is unsubstituted or substituted with one, two, three or four groups selected from hydroxyl, acyloxy and thiol; and R$^1$ is C$_{1-20}$ alkoxy, aryloxy or —O—C$_{3-20}$ heterocyclyl, wherein said heterocyclyl is a group derived from a group of the following structure:

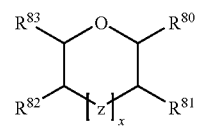

wherein x is 0 or 1; z is CHR$^{84}$; and R$^{80}$, R$^{81}$, R$^{82}$, R$^{83}$ and R$^{84}$, which are the same or different, are independently selected from H, C$_{1-6}$ alkyl, OH, acyloxy, SH, C$_{1-6}$ alkoxy, aryloxy, amino, C$_{1-10}$ alkylamino, di(C$_{1-10}$)alkylamino, amido and acylamido. Typically, in this embodiment, X is O. Examples of compounds of this embodiment are the Galactosyltransferase inhibitor compounds described in Chung S J, Bioorg Med Chem Lett. 1998 Dec. 1; 8(23):3359-64, whose structures are given hereinbelow.

Typically, in this embodiment, R$^1$ is a group of any one of the following structures:

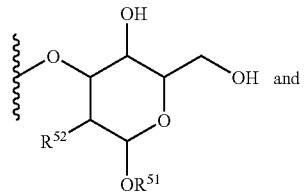

and

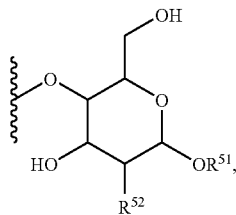

in which R$^{51}$ is a substituted or unsubstituted C$_{1-10}$ alkyl group, typically methyl, or a substituted or unsubstituted aryl group, typically a phenyl or naphthyl group. The phenyl or naphthyl may be unsubstituted or substituted. When substituted, the phenyl or naphthyl is typically substituted with a halo group, for instance with a bromo group. $R^{52}$ is typically hydroxyl, $C_{1-10}$ alkoxy, acyloxy, aryloxy or acylamido. Typically, $R^{52}$ is —OH or —NHC(O)Me.

Alternatively, in this embodiment, $R^1$ may be $C_{1-20}$ alkoxy wherein said $C_{1-20}$ alkoxy group is substituted with an ester group or an aryl group, for instance with —C(O)OCH$_3$ or Ph. Alternatively, in this embodiment, $R^1$ may be aryloxy wherein the aryl group bonded to the oxygen of said aryloxy is either substituted or unsubstituted phenyl, or substituted or unsubstituted naphthyl. Typically, the phenyl or naphthyl is either unsubstituted or monosubstituted with halo or methoxy.

Typically, in this embodiment, $R^6$ is H, amino or hydroxyl, more typically, amino or hydroxyl. Typically, in this embodiment, $R^2$ is H, hydroxyl or —NHC(O)CH$_3$, more typically hydroxyl or —NHC(O)CH$_3$. Typically, in this embodiment, $R^3$ is H or hydroxyl, more typically hydroxyl. Typically, in this embodiment, $R^4$ is H, CH$_2$OH or CH$_2$SH, more typically CH$_2$OH or CH$_2$SH.

In another embodiment, the inhibitor of sphingolipid biosynthesis is of formula (Ia) and:

X is O or S; n is 1; Y is CHR$^6$; R$^6$ is H, hydroxyl, acyloxy or $C_{1-20}$ alkoxy;

$R^1$ and $R^{11}$ which may be the same or different, are independently selected from H, $C_{1-20}$ alkyl, hydroxyl, acyloxy, $C_{1-20}$ alkoxy, carboxyl, ester, —O—$C_{3-25}$ cycloalkyl, and a group of the following formula (VII):

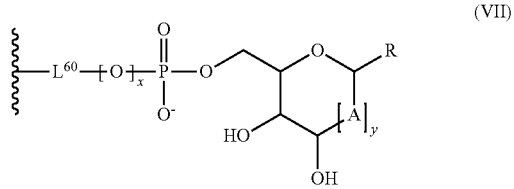
(VII)

wherein $L^{60}$ is substituted or unsubstituted $C_{1-20}$ alkylene; x is 0 or 1; y is 0 or 1; A is CHR''' and R is H, $C_{1-20}$ alkyl, $C_{3-20}$ heterocyclyl, $C_{3-25}$ cycloalkyl, aryl or $C_{1-20}$ alkoxy, wherein R''' is hydroxyl, $C_{1-6}$ alkoxy, aryloxy or acyl;

$R^2$ is H, $C_{1-20}$ alkyl, hydroxyl, acyloxy or —O—$C_{3-20}$ heterocyclyl, wherein said heterocyclyl is a group derived from a group of the following structure:

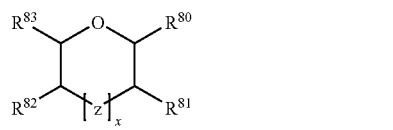

wherein x is 0 or 1; z is CHR$^{84}$; and R$^{80}$, R$^{81}$, R$^{82}$, R$^{83}$ and R$^{84}$, which are the same or different, are independently selected from H, $C_{1-6}$ alkyl, OH, SH, $C_{1-6}$ alkoxy, aryloxy, amino, $C_{1-10}$ alkylamino, di($C_{1-10}$)alkylamino, amido, acylamido and a group derived from a second group of the following structure:

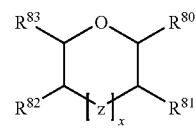

in which second group x is 0 or 1; z is CHR$^{84}$; and R$^{80}$, R$^{81}$, R$^{82}$, R$^{83}$ and R$^{84}$, which are the same or different, are independently selected from H, $C_{1-6}$ alkyl, OH, SH, $C_{1-6}$ alkoxy, aryloxy, amino, $C_{1-10}$ alkylamino, di($C_{1-10}$)alkylamino, amido and acylamido;

$R^3$ is H, hydroxyl, acyloxy, $C_{1-20}$ alkoxy or acylamido; and $R^4$ is H, carboxyl, ester or $C_{1-20}$ alkyl which is unsubstituted or substituted with one, two, three or four groups selected from hydroxyl and thiol.

Examples of compounds of this embodiment are sialic acid, cytidin-5'-yl sialylethylphosphonate and Soyasaponin I.

Typically, in this embodiment, X is O.

Typically, in this embodiment, $R^6$ is H or hydroxyl, more typically hydroxyl.

Typically, in this embodiment, $R^1$ and $R^{11}$ are independently selected from H, hydroxyl, carboxyl, —O—$C_{3-25}$ cycloalkyl and a group of formula (VII) in which $L^{60}$ is ethylene or methylene, R''' is hydroxyl, and R is either —OCH$_3$ or a heterocyclic group of the following structure:

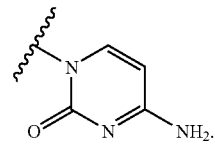 [SMILES: *n1ccc(N)nc1=O]

Both $R^1$ and $R^{11}$ may be groups of formula (VII).

When $R^1$ or $R^{11}$ is —O—$C_{3-25}$ cycloalkyl, the cycloalkyl group is a group derived from a compound of one of the following formulae, which compound may be substituted or unsubstituted:

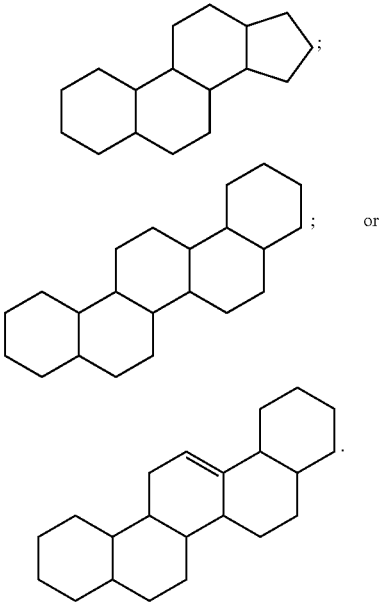

More typically, the cycloalkyl group of said —O—$C_{3-25}$ cycloalkyl is a group derived from the following compound:

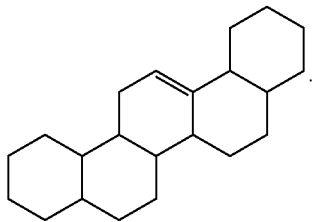 [SMILES: C1=C2C3CCCCC3CCC2C2CCC3CCCCC3C2C1]

Typically, if either $R^1$ or $R^{11}$ is —O—$C_{3-25}$ cycloalkyl, then the other one of those groups, i.e. $R^{11}$ or $R^1$ respectively, is H.

Typically, in this embodiment, $R^2$ is H or —O—$C_{3-20}$ heterocyclyl, wherein said heterocyclyl is a group of the following structure:

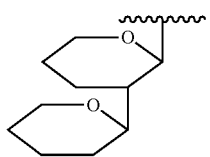

wherein each of the ring carbon atoms is independently unsubstituted or substituted with $C_{1-6}$ alkyl, OH, SH, $C_{1-6}$ alkoxy, aryloxy, amino, $C_{1-10}$ alkylamino, di($C_{1-10}$)alkylamino, amido and acylamido. Typically, each of the ring carbon atoms is independently unsubstituted or substituted with OH, $CH_2OH$ or a $C_{1-6}$ alkyl group, for instance a methyl group.

Typically, in this embodiment, $R^3$ is hydroxyl or acylamido. More typically, $R^3$ is hydroxyl or $NHC(O)CH_3$.

Typically, in this embodiment, $R^4$ is carboxyl, methyl, ethyl, propyl or butyl, which methyl, ethyl, propyl or butyl are substituted with one, two, three and four groups respectively, which groups are selected from hydroxyl and thiol. More typically, $R^4$ is carboxyl or —CH(OH)CH(OH)$CH_2OH$.

Any one of the following compounds of formula (I) may be employed in the present invention:

Iminosugars (azasugars) such as: N-butyldeoxynojirimycin (NB-DNJ), also known as miglustat or ZAVESCA®; N-nonyldeoxynojirimycin (NN-DNJ); N-butyldeoxygalactonojirimycin (NB-DGJ); N-5-adamantane-1-yl-methoxypentyl-deoxynojirimycin (AMP-DNJ); alpha-homogalactonojirimycin (HGJ); Nojirimycin (NJ); Deoxynojirimycin (DNJ); N7-oxadecyl-deoxynojirimycin; deoxygalactonojirimycin (DGJ); N-butyl-deoxygalactonojirimycin (NB-DGJ); N-nonyl-deoxygalactonojirimycin (NN-DGJ); N-nonyl-6deoxygalactonojirimycin; N7-oxanonyl-6deoxy-DGJ; alpha-homoallonojirimycin (HAJ); beta-1-C-butyl-deoxygalactonojirimycin (CB-DGJ). Such compounds are glycosyltransferase inhibitors ("sugar mimics").

D,L-threo-1-phenyl-2-decanoylamino-3-morpholino-1-propanol (PDMP); D,L-threo-1-phenyl-2-hexadecanoylamino-3-morpholino-1-propanol (PPMP); D-threo-1-phenyl-2-palmitoilamino-3-pyrrolidino-1-propanol (P4); 4'-hydroxy-D-threo-1-phenyl-2-palmitoilamino-3-pyrrolidino-1-propanol (4'-hydroxy-P4); 3',4'-ethylenedioxy-P4 (EtDO-P4); 2,5-dihydroxymethyl-3,4-dihydroxypyrrolidine (L-DMDP). Such compounds are glycosyltransferase inhibitors and derivatives of sphingosine ("lipid mimics").

Iminosugars such as Castanospermine and MDL25874, which have the following structures respectively:

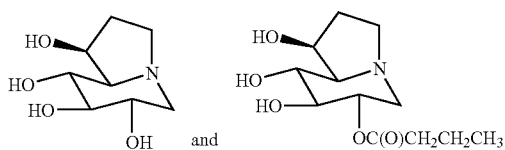

Sialyltransferase inhibitors such as N-acetylneuraminic acid (sialic acid); cytidin-5'-yl sialylethylphosphonate; and Soyasaponin I.

Galactosyltransferase inhibitor compounds of the following structures, which compounds are described in Chung S J, Bioorg Med Chem Lett. 1998 Dec. 1; 8(23): 3359-64:

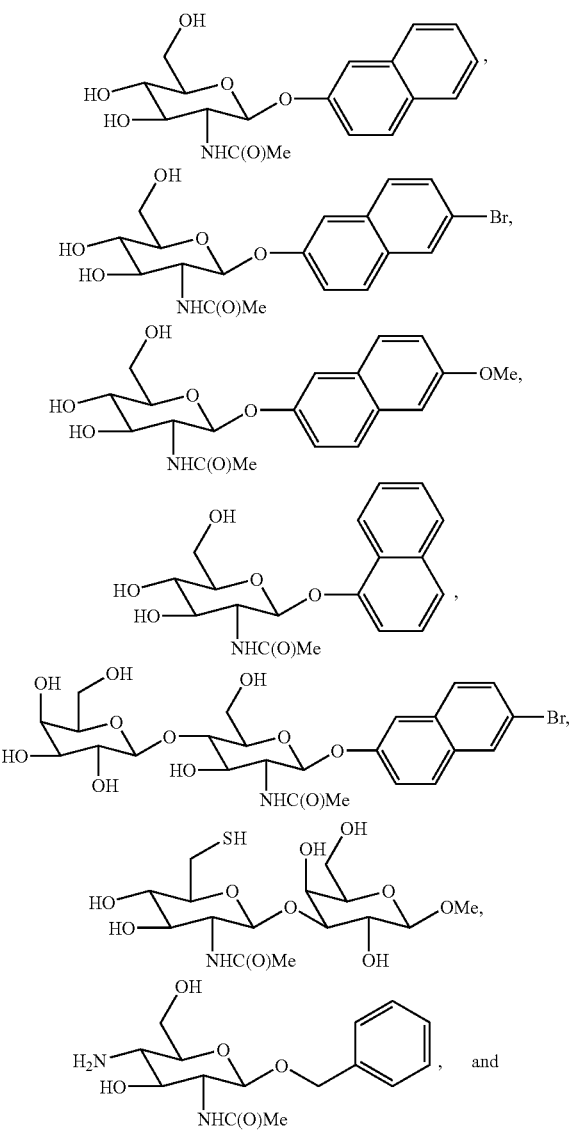

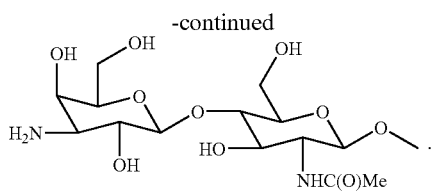

Iminosugars, such as 1,5-dideoxy-1,5-imino-D-glucitol, and their N-alkyl, N-acyl and N-aryl, and optionally O-acylated derivatives, such as: 1,5-(Butylimino)-1,5-dideoxy-D-glucitol, also known as N-butyldeoxynojirimycin (NB-DNJ), miglustat or ZAVESCA®; 1,5-(Methylimino)-1,5-dideoxy-D-glucitol; 1,5-(Hexylimino)-1,5-dideoxy-D-glucitol; 1,5-(Nonylylimino)-1,5-dideoxy-D-glucitol; 1,5-(2-Ethylbutylimino)-1,5-dideoxy-D-glucitol; 1,5-(2-Methylpentylimino)-1,5-dideoxy-D-glucitol; 1,5-(Benzyloxycarbonylimino)-1,5-dideoxy-D-glucitol, tetraacetate; 1,5-(Phenylacetylimino)-1,5-dideoxy-D-glucitol, tetraacetate; 1,5-(Benzoylimino)-1,5-dideoxy-D-glucitol, tetraacetate; 1,5-(Butylimino)-1,5-dideoxy-D-glucitol, tetraacetate; 1,5-(Ethyl malonylimino)-1,5-dideoxy-D-glucitol, tetraacetate; 1,5-(Hexylimino)-1,5-dideoxy-D-glucitol, tetraacetate; 1,5-(Nonylimino)-1,5-dideoxy-D-glucitol, tetraacetate; 1,5-(Benzyloxycarbonylimino)-1,5-dideoxy-D-glucitol, tetraisobutyrate; 1,5-(Butylimino)-1,5-dideoxy-D-glucitol, tetrabutyrate; 1,5-(Butylimino)-1,5-dideoxy-D-glucitol, tetrapropionate; 1,5-(Butylimino)-1,5-dideoxy-D-glucitol, tetrabenzoate; 1,5-Dideoxy-1,5-imino-D-glucitol, tetraisobutyrate; 1,5-(Hydrocinnamoylimino)-1,5-dideoxy-D-glucitol, tetraacetate; 1,5-(Methyl malonylimino)-1,5-dideoxy-D-glucitol, tetraacetate; 1,5-(Butylimino)-1,5-dideoxy-D-glucitol, tetraisobutyrate; 1,5-(Butylimino)-1,5-dideoxy-4R,6-O-(phenylmethylene)-D-glucitol, diacetate; 1,5-[(Phenoxymethyl)carbonylimino]-1,5-dideoxy-D-glucitol, tetraacetate; 1,5-[(Ethylbutyl)imino]-1,5-dideoxy-D-glucitol, tetraacetate; 1,5-(Butylimino)-1,5-dideoxy-D-glucitol, 2,3-diacetate; 1,5-(Hexylimino)-1,5-dideoxy-4R,6-O-(phenylmethylene)-D-glucitol, diacetate; 1,5-(Hexylimino)-1,5-dideoxy-D-glucitol, 2,3-diacetate; 1,5-[(2-Methylpentyl)imino]-1,5-dideoxy-D-glucitol, tetraacetate; 1,5-(Butylimino)-1,5-dideoxy-D-glucitol, 6-acetate; 1,5-[(3-Nicotinoyl)imino]-1,5-dideoxy-D-glucitol, tetraacetate; 1,5-(Cinnamoylimino)-1,5-dideoxy-D-glucitol, tetraacetate; 1,5-(Butylimino)-1,5-dideoxy-D-glucitol, 2,3-dibutyrate; 1,5-(Butylimino)-1,5-dideoxy-4R,6-O-(phenylmethylene)-D-glucitol, 2,3-dibutyrate; 1,5-(Phenylacetylimino)-1,5-dideoxy-D-glucitol, tetraisobutyrate; 1,5-[(4-Chlorophenyl)acetylimino]-1,5-dideoxy-D-glucitol, tetraacetate; 1,5-[(4-Biphenyl)acetylimino]-1,5-dideoxy-D-glucitol, tetraacetate; 1,5-(Benzyloxycarbonylimino)-1,5-dideoxy-D-glucitol, tetrabutyrate; 1,5-Dideoxy-1,5-imino-D-glucitol, tetrabutyrate; 3,4,5-piperidinetriol, 1-propyl-2-(hydroxymethyl)-, (2S,3R,4R,5S); 3,4,5-piperidinetriol, 1-pentyl-2-(hydroxymethyl)-, (2S,3R,4R,5S); 3,4,5-piperidinetriol, 1-heptyl-2-(hydroxymethyl)-, (2S,3R,4R,5S); 3,4,5-piperidinetriol, 1-butyl-2-(hydroxymethyl)-, (2S,3S,4R,5S); 3,4,5-piperidinetriol, 1-nonyl-2-(hydroxymethyl)-, (2S,3R,4R,5S); 3,4,5-piperidinetriol, 1-(1-ethyl)propyl-2-(hydroxymethyl)-, (2S,3R,4R,5S); 3,4,5-piperidinetriol, 1-(3-methyl)butyl-2-(hydroxymethyl)-, (2S,3R,4R,5S); 3,4,5-piperidinetriol, 1-(2-phenyl)ethyl-2-(hydroxymethyl)-, (2S,3R,4R,5S); 3,4,5-piperidinetriol, 1-(3-phenyl)propyl-2-(hydroxymethyl)-, (2S,3R,4R,5S); 3,4,5-piperidinetriol, 1-(1-ethyl)hexyl-2-(hydroxymethyl)-, (2S,3R,4R,5S); 3,4,5-piperidinetriol, 1-(2-ethyl)butyl-2-(hydroxymethyl)-, (2S,3R,4R,5S); 3,4,5-piperidinetriol, 1-[(2R)-(2-methyl-2-phenyl)ethyl]-2-(hydroxymethyl)-, (2S,3R,4R,5S); 3,4,5-piperidinetriol, 1-[(2S)-(2-methyl-2-phenyl)ethyl]-2-(hydroxymethyl)-, (2S,3R,4R,5S), β-L-homofuconojirimycin; and propyl 2-acetamido-2-deoxy-4-O-(β-D-galactopyranosyl)-3-O-(2-(N-(β-L-homofuconojirimycinyl))ethyl)-α-D-glucopyranoside.

Iminosugars, such as ido-N-(5-adamantane-1-yl-methoxy-pentyl)deoxynojirimycin; N-(adamantane-1-yl-methoxypentyl)-L-ido-deoxynojirimycin; N-(adamantane-1-yl-methoxypentyl)-D-galacto-deoxynojirimycin; C1-beta-(adamantane-1-yl-methoxypentyl)-deoxynojirimycin; N-methyl-C1-beta-(adamantane-1-yl-methoxypentyl)-deoxynojirimycin; N-butyl-C1-beta-(adamantane-1-yl-methoxypentyl)-deoxynojirimycin; 2-O-(adamantane-1-yl-methoxypentyl)-deoxynojirimycin; N-methyl-2-O-(adamantane-1-yl-methoxy-pentyl)-deoxynojirimycin; N-butyl-2-O-(adamantane-1-yl-methoxy-pentyl)-deoxynojirimycin; N-benzyloxycarbonyl-2-O-(adamantane-1-yl-methoxypentyl)-3,4,6-tri-O-benzyl-deoxy-nojirimycin; and N-(5-adamantane-1-yl-methoxy-pentyl)deoxynojirimycin.

Methods of synthesizing such iminosugar compounds are known and are described, for example, in WO 02/055498 and in U.S. Pat. Nos. 5,622,972, 4,246,345, 4,266,025, 4,405,714, and 4,806,650, U.S. patent application Ser. No. 07/851,818, filed Mar. 16, 1992, US 2007/0066581 and EP 1528056. For example, N-nonyl-DNJ and N-decyl-DNJ can be conveniently prepared by the N-nonylation or N-decylation, respectively, of 1,5-dideoxy-1,5-imino-D-glucitol (DNJ) by methods analogous to the N-butylation of DNJ as described in Example 2 of U.S. Pat. No. 4,639,436 by substituting an equivalent amount of n-nonylaldehyde or n-decylaldehyde for n-butylraldehyde. The starting materials are readily available from many commercial sources.

Typically, the compound of formula (I) employed is N-butyldeoxynojirimycin (NB-DNJ) or N-butyldeoxygalactonojirimycin (NB-DGJ). More typically, the compound of formula (I) is NB-DNJ.

NB-DGJ is the galactose analogue of NB-DNJ. NB-DGJ inhibits GSL biosynthesis comparably to NB-DNJ but lacks certain side effect activities associated with NB-DNJ. There has been extensive use of NB-DGJ in mouse models of GSL storage diseases and it is very well tolerated. Thus, in one embodiment, the compound of formula (I) employed is NB-DGJ.

In one embodiment, the compound of formula (I) employed is selected from: ido-N-(5-adamantane-1-yl-methoxy-pentyl)deoxynojirimycin; N-(adamantane-1-yl-methoxypentyl)-L-ido-deoxynojirimycin; N-(adamantane-1-yl-methoxypentyl)-D-galacto-deoxynojirimycin; C1-beta-(adamantane-1-yl-methoxypentyl)-deoxynojirimycin; N-methyl-C1-beta-(adamantane-1-yl-methoxypentyl)-deoxynojirimycin; N-butyl-C1-beta-(adamantane-1-yl-methoxypentyl)-deoxynojirimycin; 2-O-(adamantane-1-yl-methoxypentyl)-deoxynojirimycin; N-methyl-2-O-(adamantane-1-yl-methoxy-pentyl)-deoxynojirimycin; N-butyl-2-O-(adamantane-1-yl-methoxy-pentyl)-deoxynojirimycin; N-benzyloxycarbonyl-2-O-(adamantane-1-yl-methoxypentyl)-3,4,6-tri-O-benzyl-deoxy-nojirimycin; and N-(5-adamantane-1-yl-methoxy-pentyl)deoxynojirimycin.

In one embodiment the invention provides a compound for use in the treatment of a disease which has a secondary Niemann-Pick type C disease like cellular phenotype, which compound is an inhibitor of sphingolipid biosynthesis of the following formula (II):

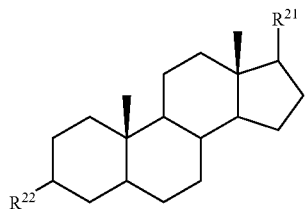
(II)

wherein:
$R^{21}$ is selected from oxo, -$L^{30}$-$R^{23}$, -$L^{30}$-C(O)N(H)—$R^{24}$ and a group of the following formula (VI):

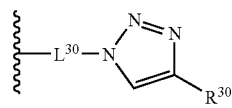
(VI)

$L^{30}$ is substituted or unsubstituted $C_{1-20}$ alkylene which is optionally interrupted by N(R'), O, S or arylene;

$R^{23}$ is carboxyl, hydroxyl, ester, phosphonate ester, phosphate ester, phosphoric acid and phosphonic acid;

$R^{24}$ is $C_{1-20}$ alkyl which is unsubstituted or substituted with one or more groups selected from carboxyl, hydroxyl, ester, phosphonate ester, phosphate ester, phosphoric acid and phosphonic acid, wherein said $C_{1-20}$ alkyl is optionally interrupted by N(R'), O, S or arylene;

$R^{30}$ is $C_{1-20}$ alkyl which is unsubstituted or substituted with one or more groups selected from carboxyl, hydroxyl, ester, amino, phosphonate ester, phosphate ester, phosphoric acid and phosphonic acid, wherein said $C_{1-20}$ alkyl is optionally interrupted by N(R'), O, S or arylene; and $R^{22}$ is hydroxyl, oxo, acyloxy, phosphoric acid or —OC(O)-alk-C(O)OH, wherein alk is substituted or unsubstituted $C_{1-20}$ alkylene which is optionally interrupted by N(R'), O, S or arylene, or a pharmaceutically acceptable salt thereof.

Typically, in the compounds of formula (II), $R^{21}$ is selected from oxo, -$L^{30}$-$R^{23}$, -$L^{30}$-C(O)N(H)—$R^{24}$ and a group of the following formula (VI):

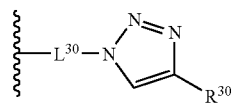
(VI)

wherein
$L^{30}$ is substituted or unsubstituted $C_{1-6}$ alkylene,
$R^{23}$ is hydroxyl, carboxyl, ester or phosphate ester,
$R^{24}$ is $C_{1-6}$ alkyl which is unsubstituted or substituted with one or two carboxyl groups, and
$R^{30}$ is $C_{1-6}$ alkyl which is unsubstituted or substituted with one or two groups selected from hydroxyl, carboxyl, amino and phosphonate ester.

More typically, $R^{21}$ is a group selected from oxo and the groups having the following structures:

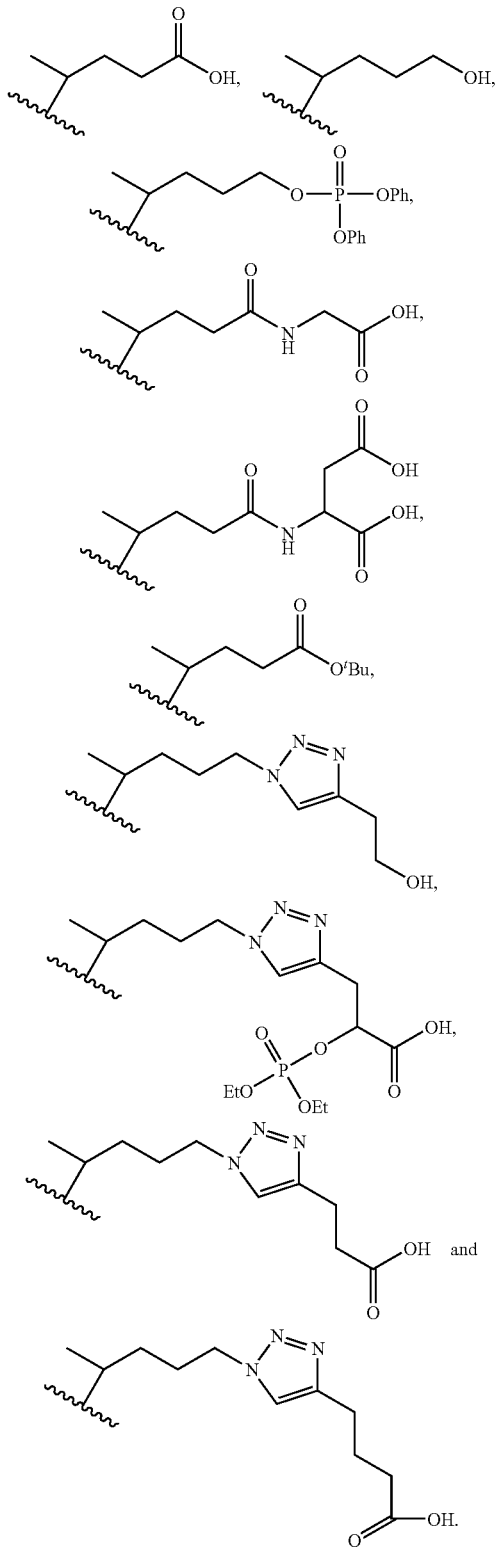

Typically, in the compounds of formula (II), $R^{22}$ is selected from hydroxyl, oxo, phosphoric acid, —OC(O)—CH$_2$—CH$_2$—C(O)OH and —OC(O)—CH(NH$_2$)—CH$_2$—C(O)OH.

Table 1 shows examples of compounds of formula (II) which may be employed in the present invention:
TABLE 1
| Compound | $R^{21}$ | $R^{22}$ |
|---|---|---|
| 1 | =O | —OC(O)CH$_2$CH$_2$C(O)OH |
| 2 | 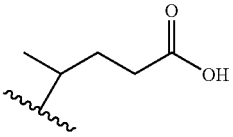 [SMILES: *C(C)CCC(=O)O] | —OH |
| 3 | =O | —OC(O)CH(NH$_2$)CH$_2$C(O)OH |
| 4 | =O | —O—P(=O)(OH)$_2$ |
| 5 | =O | —OC(O)CH$_2$CH$_2$C(O)OH |
| 6 | 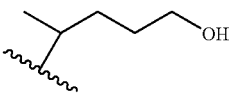 [SMILES: *C(C)CCCO] | —OH |
| 7 | 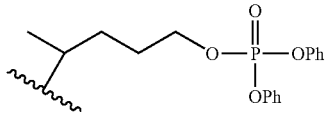 | —OH |
| 8 | 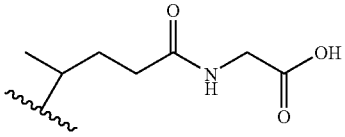 [SMILES: *C(C)CCC(=O)NCC(=O)O] | —OH |
| 9 | 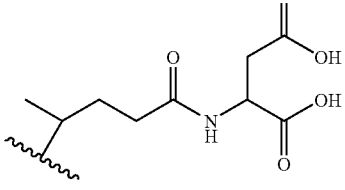 | —OH |
| 10 | 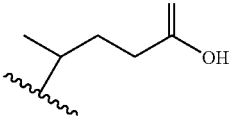 | =O |
| 11 | 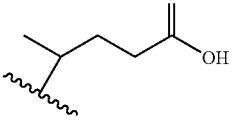 | —OC(O)CH$_2$CH$_2$C(O)OH |
| 12 | 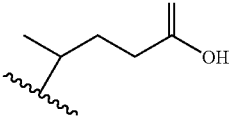 | —OC(O)CH(NH$_2$)CH$_2$C(O)OH |
| 13 | 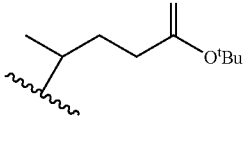 | —OC(O)CH$_2$CH$_2$C(O)OH |

TABLE 1-continued

| Compound | R²¹ | R²² |
|---|---|---|
| 14 | (structure: isopentyl-C(O)-NH-CH₂-C(O)OH) | —OC(O)CH₂CH₂C(O)OH |
| 15 | (structure: isopentyl-C(O)-NH-CH(CH₂C(O)OH)-C(O)OH) | —OC(O)CH₂CH₂C(O)OH |
| 16 | (structure: isopentyl-CH₂-C(O)OH) | —OC(O)CH(NH₂)CH₂C(O)OH |
| 17 | (structure: isopentyl-propyl-triazole-CH₂CH₂OH) | —OH |
| 18 | (structure: isopentyl-propyl-triazole-CH₂-CH(NH₂)-C(O)OH) | —OH |
| 19 | (structure: isopentyl-propyl-triazole-CH₂-CH(OP(O)(OEt)₂)-C(O)OH) | —OH |
| 20 | (structure: isopentyl-propyl-triazole-CH₂CH₂-C(O)OH) | —OH |

TABLE 1-continued

| Compound | $R^{21}$ | $R^{22}$ |
|---|---|---|
| 21 | 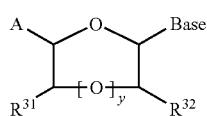 | —OH |

The synthesis of such compounds is described in Chang K H et al. Chem Commun (Camb). 2006 Feb. 14; (6):629-31.

In one embodiment the invention provides a compound for use in the treatment of a disease which has a secondary Niemann-Pick type C disease like cellular phenotype, which compound is an inhibitor of sphingolipid biosynthesis of the following formula (III):

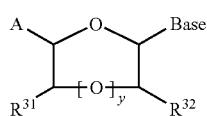

(III)

wherein:

Base is selected from a group of any one of the following formulae (a), (b), (c), (d), (e), (f) and (g):

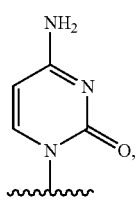

(a)

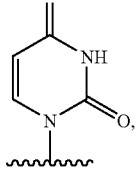

(b)

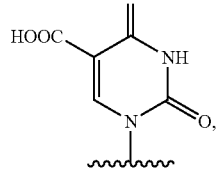

(c)

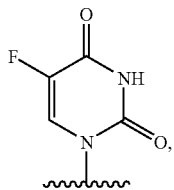

(d)

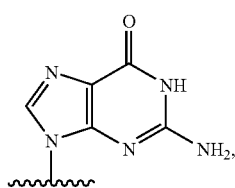

(e)

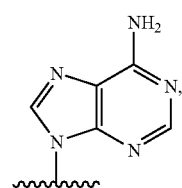

(f)

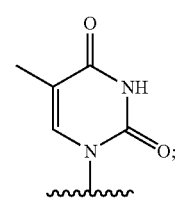

(g)

y is 0 or 1;

$R^{31}$ is OH; $R^{32}$ is H or OH; or, provided that y is 0, $R^{31}$ and $R^{32}$ together form —O—C($R^{33}$)($R^{34}$)—O—, wherein $R^{33}$ and $R^{34}$ are independently selected from H and methyl;

A is substituted or unsubstituted $C_{1-20}$ alkyl, substituted or unsubstituted $C_{1-20}$ alkylene-aryl, substituted or unsubstituted $C_{1-20}$ alkylene-$C_{3-20}$ heteroaryl, substituted or unsubstituted $C_{1-20}$ alkylene-$C_{3-25}$ cycloalkyl or substituted or unsubstituted $C_{1-20}$ alkylene-$C_{3-20}$ heterocyclyl, wherein said $C_{1-20}$ alkyl and $C_{1-20}$ alkylene are optionally interrupted by N(R'), O, S or arylene, wherein R' is H, $C_{1-6}$ alkyl or aryl, or A is a group of any one of the following formulae (g) to (k):

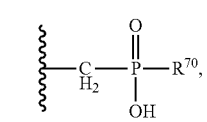

(g)

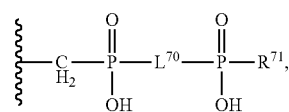

(h)

-continued

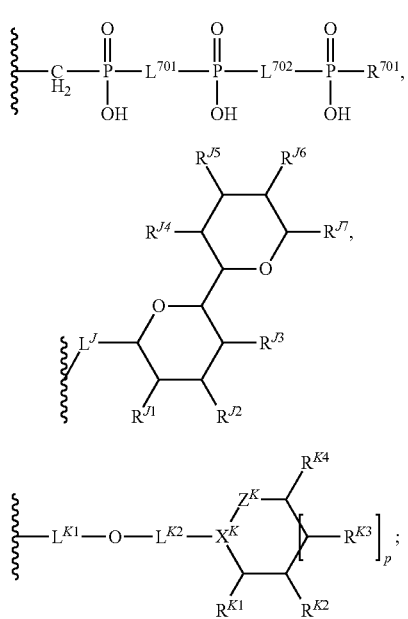

$L^{70}$, $L^{701}$ and $L^{702}$ are independently selected from —O—, —C($R^{35}$)($R^{36}$)— and —NH—, wherein $R^{35}$ and $R^{36}$ are independently selected from H, OH and $CH_3$;

$R^{70}$, $R^{71}$ and $R^{701}$ are selected from OH, substituted or unsubstituted $C_{1-20}$ alkyl, substituted or unsubstituted $C_{1-20}$ alkoxy, substituted or unsubstituted $C_{1-10}$ alkylamino and -$L^{71}$-($X^2$)$_m$-$L^{72}$-$R^{72}$; wherein m is 0 or 1; $X^2$ is O, S, —C($R^{45}$)($R^{46}$)— or —O—C($R^{45}$)($R^{46}$)—, wherein $R^{45}$ and $R^{46}$ are independently selected from H, OH, phosphonic acid or a phosphonic acid salt; $L^{71}$ and $L^{72}$ are independently selected from a single bond and substituted or unsubstituted $C_{1-20}$ alkylene, which $C_{1-20}$ alkylene is optionally interrupted by N(R'), O, S or arylene, wherein R' is H, $C_{1-6}$ alkyl or aryl; and $R^{72}$ is $C_{3-25}$ cycloalkyl or $C_{3-20}$ heterocyclyl;

$L^J$ is substituted or unsubstituted $C_{1-20}$ alkylene;

$R^{J1}$, $R^{J2}$, $R^{J3}$, $R^{J4}$, $R^{J5}$, $R^{J6}$ and $R^{J7}$, which are the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido, —N(H)C(O)CH=CH—$R^{J8}$, —O—$C_{3-25}$ cycloalkyl and —O—$C_{3-20}$ heterocyclyl, wherein said $C_{1-20}$ alkyl is optionally interrupted by N(R'), O, S or arylene, and wherein $R^{J8}$ is substituted or unsubstituted $C_{1-20}$ alkyl;

$L^{K1}$ and $L^{K2}$, which are the same or different, are independently selected from a single bond and substituted or unsubstituted $C_{1-20}$ alkylene;

$X^K$ is N or C($R^{K6}$), wherein $R^{K6}$ is H, COOH or ester;

$Z^K$ is O or CH($R^{K5}$);

p is 0 or 1; and $R^{K1}$, $R^{K2}$, $R^{K3}$, $R^{K4}$ and $R^{K5}$, which are the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido, —O—$C_{3-25}$ cycloalkyl and —O—$C_{3-20}$ heterocyclyl, wherein said $C_{1-20}$ alkyl is optionally interrupted by N(R'), O, S or arylene;

or a pharmaceutically acceptable salt thereof.

Typically, in the compounds of formula (III), Base is selected from (a) (i.e. cytosine), (b) (i.e. uracil), (c) (i.e. carboxy-substituted uracil), (d) (i.e. fluoro-substituted uracil) and (e) (i.e. guanine).

Typically, y is 0 and $R^{31}$ and $R^{32}$ are both —OH.

In one embodiment, y is 1, and $R^{31}$ and $R^{32}$ together form —O—C($R^{33}$)($R^{34}$)—O—, wherein $R^{33}$ and $R^{34}$ are as defined above. Typically, in that embodiment, Base is cytosine. Typically, $R^{33}$ and $R^{34}$ are both methyl.

Typically, A is either (g), (h) or (i). More typically, A is either (g) or (h). Typically, $L^{70}$, $L^{701}$ and $L^{702}$ are independently selected from O, $CH_2$, CHOH, C(OH)($CH_3$) and NH. More typically, $L^{70}$, $L^{701}$ and $L^{702}$ are independently selected from O or $CH_2$. Even more typically, $L^{70}$, $L^{701}$ and $L^{702}$ are O.

Typically, $R^{70}$, $R^{71}$ and $R^{701}$ are -$L^{71}$-($X^2$)$_m$-$L^{72}$-$R^{72}$; wherein m, $X^2$, $L^{71}$, $L^{72}$ and $R^{72}$ are as defined above. Typically, $L^{71}$ is a single bond or a substituted or unsubstituted $C_{1-6}$ alkyl group. Typically, $L^{72}$ is a single bond or a substituted or unsubstituted $C_{1-6}$ alkyl group. Typically, m is 1 and $X^2$ is O, S, —CH(OH)— or —O—CH($R^{46}$)— wherein $R^{46}$ is phosphonic acid or a phosphonic acid salt. Alternatively, m may be 0.

Typically, $R^{72}$ is a group of the following formula (a'):

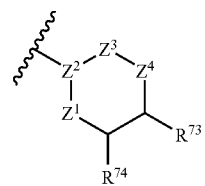

wherein $Z^1$ is CH$R^{Z1}$ and $Z^2$ is C$R^{Z2}$ wherein $Z^1$ and $Z^2$ are connected by a single bond, or $Z^1$ is CH and $Z^2$ is C wherein $Z^1$ and $Z^2$ are connected by a double bond;

$Z^3$ is CH$R^{Z3}$ or O, and $Z^4$ is CH$R^{Z4}$ or O, provided that $Z^3$ and $Z^4$ are not both O;

$R^{Z2}$ is H or COOR$^{Z2a}$, wherein $R^{Z2a}$ is H, methyl or ethyl;

$R^{Z1}$, $R^{Z3}$, $R^{Z4}$, $R^{73}$ and $R^{74}$, which may be the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido —O—$C_{3-25}$ cycloalkyl and —O—$C_{3-20}$ heterocyclyl, wherein said $C_{1-20}$ alkyl is optionally interrupted by N(R'), O, S or arylene.

Typically, $R^{Z1}$ is H, OH, NHC(O)$CH_3$ or phenoxy. Typically, $R^{Z2}$ is H or COOH. Typically, $R^{Z3}$ is H, OH, NHC(O)$CH_3$ or phenoxy. Typically $R^{Z4}$, $R^{73}$ and $R^{74}$ are independently selected from H; OH; $CH_2OH$; $NH_2$; $NH_3^+$; NHC(O)$CH_3$; phenoxy; $C_{1-4}$ alkyl substituted with 1 to 3 hydroxyl, unsubstituted alkoxy or acyloxy groups; and $C_{1-4}$ alkoxy substituted with 1 to 3 hydroxyl, unsubstituted $C_{1-4}$ alkoxy or acyloxy groups. More typically, $R^{Z4}$, $R^{73}$ and $R^{74}$ are independently selected from H; OH; $CH_2OH$; $NH_3^+$; NHC(O)$CH_3$; phenoxy; methyl; ethyl; propyl and butyl; which methyl, ethyl, propyl or butyl are substituted with one, two, three and four hydroxyl groups respectively. Even more typically, $R^{Z4}$, $R^{73}$ and $R^{74}$ are independently selected from H, OH, $CH_2OH$, $NH_3^+$, NHC(O)$CH_3$, phenoxy, —OCH$_2$CH$_2$OH and —CH(OH)CH(OH)CH$_2$OH.

When $R^{72}$ is (a'), typically $L^{71}$ is a single bond, $L^{72}$ is a single bond, m is 1 and $X^2$ is O or S. In another embodiment, when $R^{72}$ is (a'), typically $L^{71}$ is $CH_2$, $L^{72}$ is a single bond, and m is 0. In another embodiment, when $R^{72}$ is (a'), typically $L^{71}$ is a single bond, $L^{72}$ is a single bond, and m is 0.

In one embodiment, $R^{72}$ is a group of the following formula (b'):

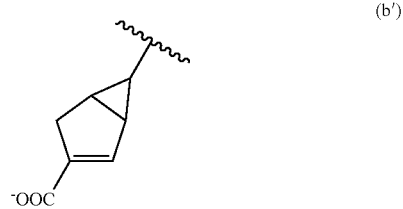

Typically, when $R^{72}$ is (b'), $L^{71}$ is a single bond, $L^{72}$ is substituted or unsubstituted $C_{1-4}$ alkyl, m is 1 and $X^2$ is O or S. More typically, when $R^{72}$ is (b'), $L^{71}$ is a single bond, $L^{72}$ is $CH_2$, m is 1 and $X^2$ is O.

In one embodiment, $R^{70}$, $R^{71}$ and $R^{701}$ are $-L^{71}-(X^2)_m-L^{72}-R^{72}$, wherein $L^{71}$, $X^2$ and m are as defined above and $L^{72}$ and $R^{72}$ together form a group of the following formula (c'):

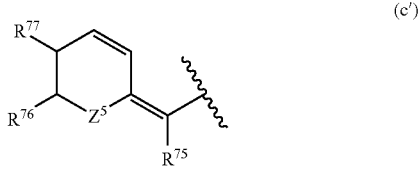

wherein:

$R^{75}$ is H, substituted or unsubstituted $C_{1-4}$ alkyl, or phosphonic acid;

$Z^5$ is O or $CH(R^{Z5})$;

$R^{76}$, $R^{77}$ and $R^{Z5}$, which may be the same or different, are independently selected from hydrogen, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido —O—$C_{3-25}$ cycloalkyl and —O—$C_{3-20}$ heterocyclyl, wherein said $C_{1-20}$ alkyl is optionally interrupted by N(R'), O, S or arylene.

Typically in this embodiment, $L^{71}$ is a single bond. Typically in this embodiment, m is 1 and $X^2$ is O or S. More typically, m is 1 and $X^2$ is O. Typically, $R^{75}$ is H or phosphonic acid. Typically, $R^{76}$, $R^{77}$ and $R^{Z5}$, which are the same or different, are independently selected from H; OH; $CH_2OH$; $NH_2$; $NH_3^+$; $NHC(O)CH_3$; phenoxy; $C_{1-4}$ alkyl substituted with 1 to 3 hydroxyl, unsubstituted $C_{1-4}$ alkoxy or acyloxy groups; and $C_{1-4}$ alkoxy substituted with 1 to 3 hydroxyl, unsubstituted $C_{1-4}$ alkoxy or acyloxy groups. More typically, $R^{76}$, $R^{77}$ and $R^{Z5}$ are independently selected from H; OH; $CH_2OH$; $NH_3^+$; $NHC(O)CH_3$; phenoxy; methyl; ethyl; propyl and butyl; which methyl, ethyl, propyl or butyl are substituted with one, two, three and four hydroxyl groups respectively. Even more typically, $R^{76}$, $R^{77}$ and $R^{Z5}$ are independently selected from H, OH, $CH_2OH$, $NHC(O)CH_3$, phenoxy, —$OCH_2CH_2OH$ and —$CH(OH)CH(OH)CH_2OH$. Typically, $R^{Z5}$ is H. Typically, $R^{76}$ is selected from H, OH, $CH_2OH$, $NHC(O)CH_3$, phenoxy, —$OCH_2CH_2OH$ and —$CH(OH)CH(OH)CH_2OH$. Typically, $R^{77}$ is H, OH or $NHC(O)CH_3$. More typically, $R^{76}$ is —$CH(OH)CH(OH)CH_2OH$ or phenoxy and $R^{77}$ is $NHC(O)CH_3$. Typically, $Z^5$ is O.

In one embodiment, $R^{70}$, $R^{71}$ and $R^{701}$ are selected from a $C_{1-6}$ alkyl group substituted with phosphonic acid, carboxyl or —$CH_3C(=CH_2)COOH$; a $C_{1-10}$ alkylamino group substituted with a carboxyl group; and a $C_{1-10}$ alkoxy group substituted with one or more groups selected from phenyl, phosphonic acid, phosphonic acid salt, 2-furyl, carboxyl, —COONa or benzyl. In particular, $R^{70}$, $R^{71}$ and $R^{701}$ may be selected from a methyl group substituted with phosphonic acid, carboxyl or —$CH_3C(=CH_2)COOH$; an ethyl group substituted with phosphonic acid or carboxyl; a $C_{1-10}$ alkylamino group substituted with a carboxyl group; and $OCH(Z^6)(Z^7)$, wherein $Z^6$ and $Z^7$, which may be the same or different, are independently selected from phenyl, phosphonic acid, phosphonic acid salt, 2-furyl, carboxyl, —COONa and benzyl.

In one embodiment, A in formula (III) is selected from substituted $C_{1-20}$ alkyl, substituted $C_{1-20}$ alkylene-aryl and substituted $C_{1-20}$ alkylene-$C_{3-20}$ heteroaryl. For instance, in one embodiment, A is a group of the following formula (d'):

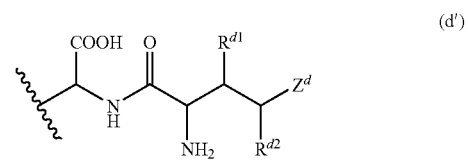

wherein $Z^d$ is substituted or unsubstituted phenyl, substituted or unsubstituted pyridyl or —$CH_2OC(O)NH_2$; $R^{d1}$ is OH, $C_{1-4}$ alkyl or $C_{1-4}$ alkoxy; and $R^{d2}$ is OH, $C_{1-4}$ alkyl or $C_{1-4}$ alkoxy. In one embodiment, A is a group of one of the following formula (d'') and (d'''):

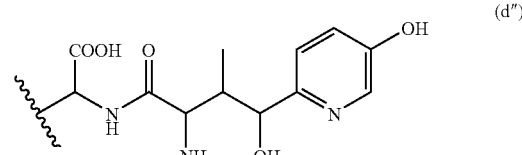

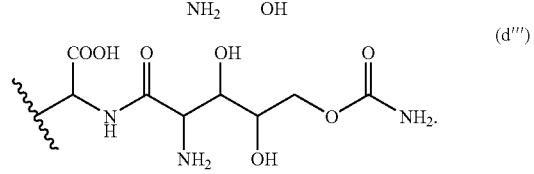

Typically, when A of formula (III) is (j), $L^J$ is substituted or unsubstituted $C_{1-4}$ alkylene. More typically, $L^J$ is $C_{1-4}$ alkylene substituted with a hydroxyl group. For instance, $L^J$ may be —$CH(OH)CH_2$—. Typically, $R^{J1}$ and $R^{J2}$ are selected from H, OH, $CH_2OH$, $NHC(O)CH_3$ and unsubstituted $C_{1-4}$ alkyl. More typically $R^{J1}$ and $R^{J2}$ are both OH. Typically, $R^{J3}$ is —N(H)C(O)CH=CH—$R^{J8}$. Typically $R^{J8}$ is a $C_{1-20}$ alkyl group substituted with an unsubstituted $C_{1-4}$ alkyl group, for instance a $C_{11}$ alkyl group substituted with a methyl group. Typically, $R^{J4}$, $R^{J5}$, $R^{J6}$ and $R^{J7}$ are selected from H, OH, $CH_2OH$, $NHC(O)CH_3$ and unsubstituted $C_{1-4}$ alkyl. More typically, $R^{J7}$ is $CH_2OH$, $R^{J6}$ and $R^{J5}$ are both OH, and $R^{J4}$ is $NHC(O)CH_3$.

Typically, when A of formula (III) is (k), $L^{K1}$ is unsubstituted $C_{1-4}$ alkylene. For instance, $L^{K1}$ may be methylene, ethylene or propylene. Typically, $L^{K2}$ is a single bond or $C_{1-6}$ alkylene, which $C_{1-6}$ alkylene is unsubstituted or substituted with an oxo group. For instance, in one embodiment, $L^{K2}$ is either a single bond or —C(O)CH$_2$C(O)—. Typically X$^K$ is N, CH, COOH or COOCH$_3$. Typically Z$^K$ is O or CH(CH$_2$OH).

In one embodiment, X$^K$ is N, Z$^K$ is CH(R$^{K5}$) and p is 0. Typically, in this embodiment, R$^{K1}$, R$^{K2}$, R$^{K4}$ and R$^{K5}$, which are the same or different, are independently selected from H, OH, CH$_2$OH, NH$_2$, NHC(O)CH$_3$, phenoxy and C$_{1-4}$ alkyl, which C$_{1-4}$ alkyl is unsubstituted or substituted with 1 to 3 hydroxyl groups. More typically, in this embodiment, R$^{K5}$, R$^{K1}$ are both CH$_2$OH, and R$^{K2}$ and R$^{K4}$ both OH.

In another embodiment, X$^K$ is CH, COOH or ester (for instance COOCH$_3$), Z$^K$ is O and p is 1. Typically, in this embodiment, R$^{K1}$ and R$^{K4}$, which are the same or different, are independently selected from H, OH, CH$_2$OH, NH$_2$, NHC(O)CH$_3$, acyloxy, phenoxy and C$_{1-4}$ alkyl, which C$_{1-4}$ alkyl is unsubstituted or substituted with 1 to 3 hydroxyl or acyloxy groups. More typically, R$^{K1}$ and R$^{K4}$ are independently selected from H, OH, CH$_2$OH, —CH(OH)CH(OH)CH$_2$OH and —CH(OAc)CH(OAc)CH$_2$OAc, wherein Ac is —C(O)CH$_3$. Typically, in this embodiment, R$^{K2}$ and R$^{K3}$, which are the same or different, are independently selected from H; OH; CH$_2$OH; NH$_2$; NHC(O)CH$_3$; acyloxy; phenoxy; C$_{1-4}$ alkyl, which C$_{1-4}$ alkyl is unsubstituted or substituted with 1 to 3 hydroxyl or acyloxy groups; and a group of the following formula (e'):

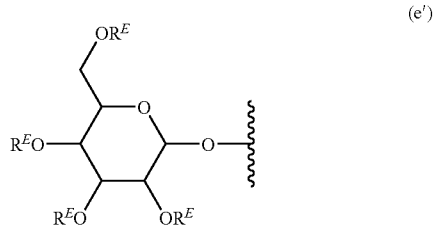

(e')

wherein each R$^E$ is either H or acyl. Typically each R$^E$ is H.

In one embodiment, the inhibitor of sphingolipid biosynthesis is of formula (III) wherein Base is selected from (a), (b), (c), (d) and (e); y is 0 and R$^{31}$ and R$^{32}$ are both —OH; A is either (g), (h) or (i); L$^{70}$, L$^{701}$ and L$^{702}$ are selected from O, CH$_2$, CHOH, C(OH)(CH$_3$) and NH; and R$^{70}$, R$^{71}$ and R$^{701}$ are as defined above.

Table 2 shows examples of compounds of formula (III) which may be employed in the present invention. The compounds in Table 2 are described in R. Wang et al., Bioorg. & Med. Chem., Vol. 5, No. 4, pp 661-672, 1997; X. Wang et al., Medicinal Research Reviews, Vol. 23, No. 1, 32-47, 2003; Schäfer et al., J. Org. Chem. 2000, 65, 24-29; and Qiao et al., J. Am. Chem. Soc., 1996, 118, 7653-7662.

TABLE 2

| Compound | Compound structure |
|---|---|
| 22 | ![structure 22] |
| 23 | ![structure 23] |
| 24 | ![structure 24] |

TABLE 2-continued
| Compound | Compound structure |
|---|---|
| 25 | 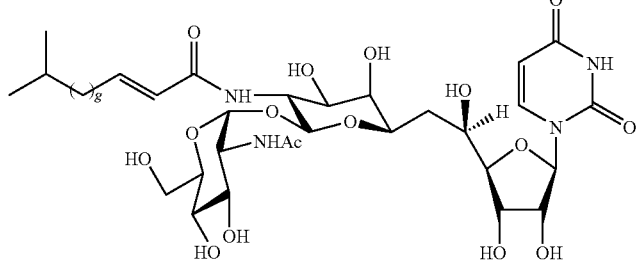 |
| 26 | 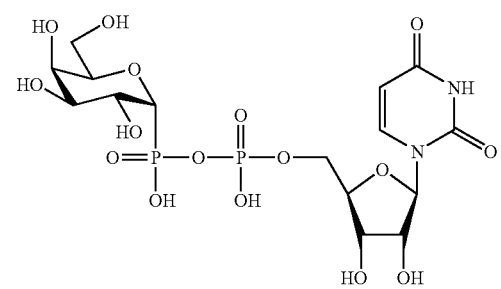 |
| 27 | 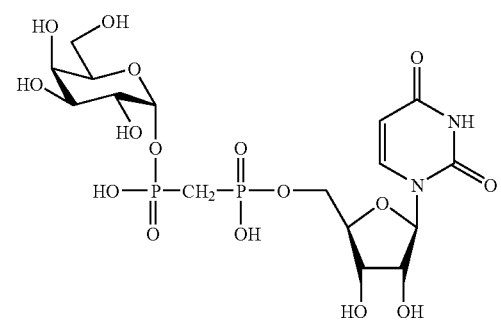 |
| 28 | 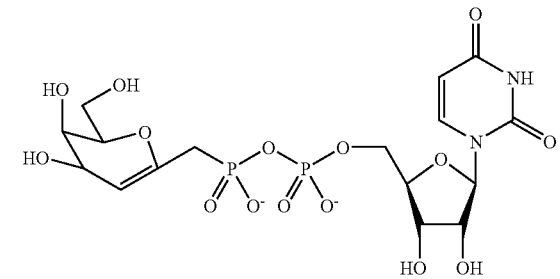 |
| 29 | 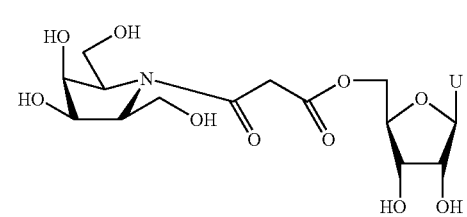 |
(U = uracil)

TABLE 2-continued
| Compound | Compound structure |
|---|---|
| 30 | 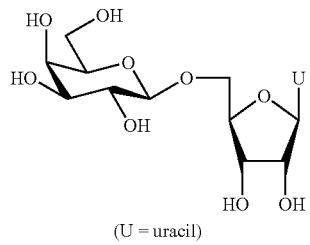<br>(U = uracil) |
| 31 | 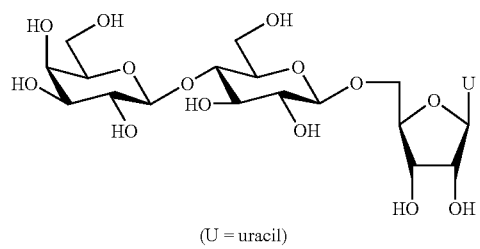<br>(U = uracil) |
| 32 | 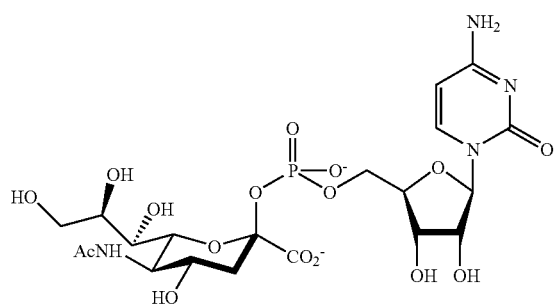 |
| 33 | 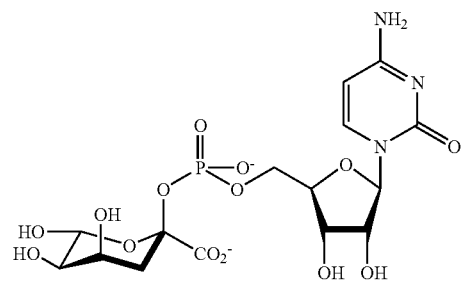 |
| 34 | 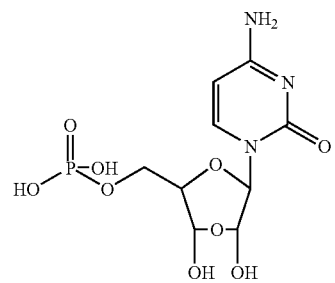 [SMILES: Nc1ccn(C2OC(COP(=O)(O)O)C(O)OC2O)c(=O)n1] |

TABLE 2-continued

| Compound | Compound structure |
|---|---|
| 35 | 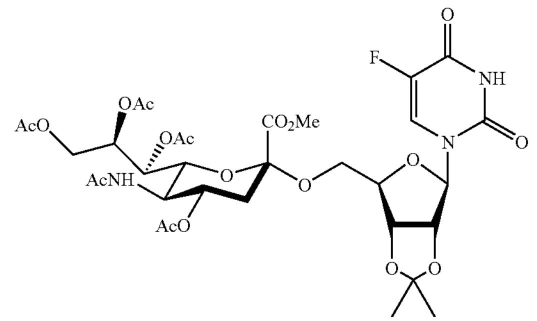 |
| 36 | 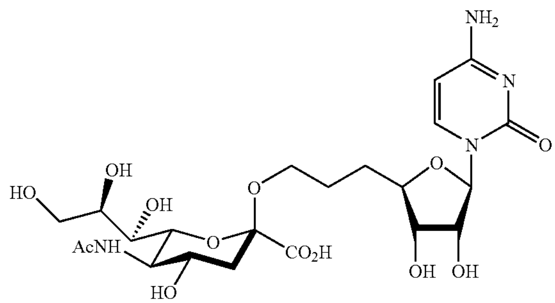 |
| 37 | 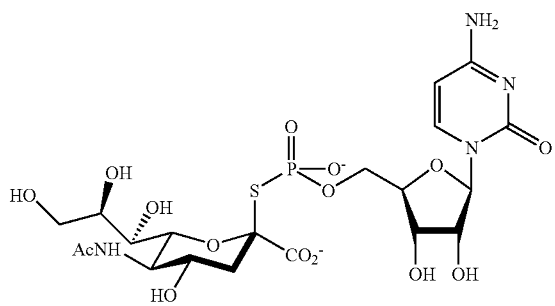 |
| 38 (a and b) | a  R = H<br>b  R = CH(OH)CH(OH)CH₂OH |
| 40 | 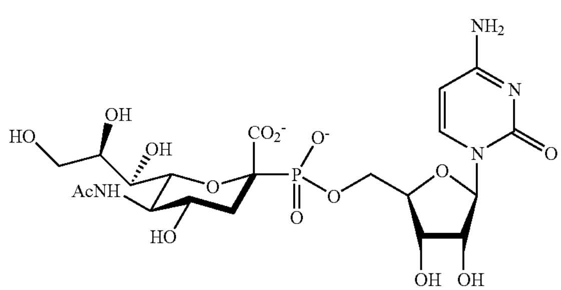 |

TABLE 2-continued
| Compound | Compound structure |
|---|---|
| 41 (a to e) | 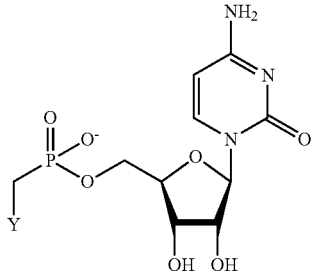 a  Y = PO$_3$H$^-$<br>b  Y = CO$_2^-$<br>c  Y = CH$_2$CO$_2^-$<br>d  Y = CH$_2$PO$_3$H$^-$<br>e  Y = CH$_3$C(=CH$_2$)CO$_2^-$ |
| 42 | 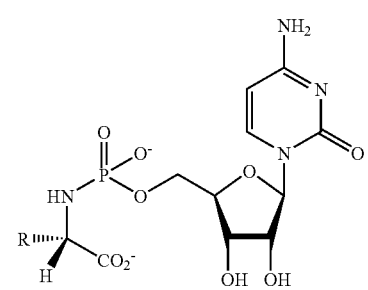 |
| 43 | 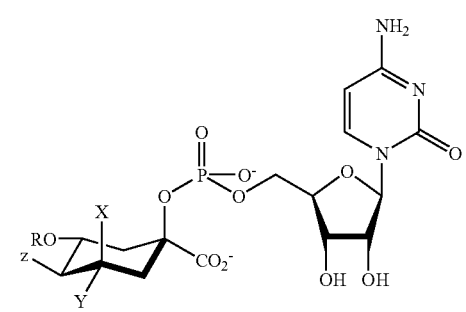 |
| 44 (a and b) | 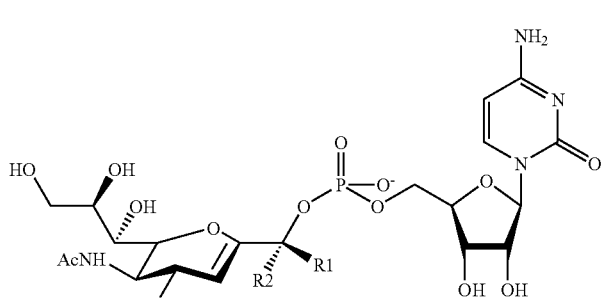 a: R1 = R2 = H<br>b: R1 = H, R2 = P(O)(OH)O$^-$Na$^+$ |

TABLE 2-continued
| Compound | Compound structure |
|---|---|
| 45 | 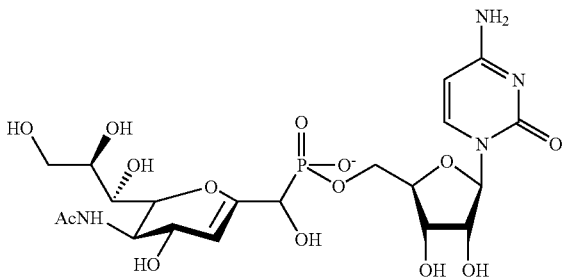 |
| 46 (a to h) | 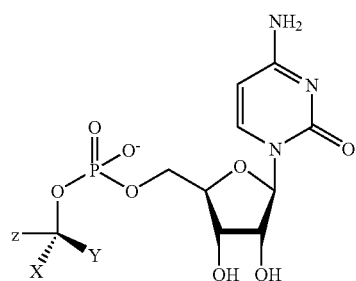<br>a: z = Ph, X = H, Y = P(O)(OH)ONa<br>b: z = Ph, X = P(O)(OH)ONa, Y = H<br>c: z = 2-furyl, X = H, Y = P(O)(OH)ONa<br>d: z = 2-furyl, X = P(O)(OH)ONa, Y = H<br>e: z = Ph, X = H, Y = CO$_2$Na<br>f: z = Ph, X = CO$_2$Na, Y = H<br>g: z = Bn, X = H, Y = CO$_2$Na<br>h: z = Bn, X = CO$_2$Na, Y = H |
| 47 (a and b) | 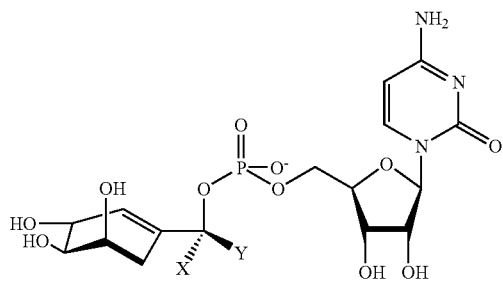<br>a: X = H, Y = P(O)(OH)(ONa)<br>b: X = P(O)(OH)(ONa), Y = H |
| 48 | 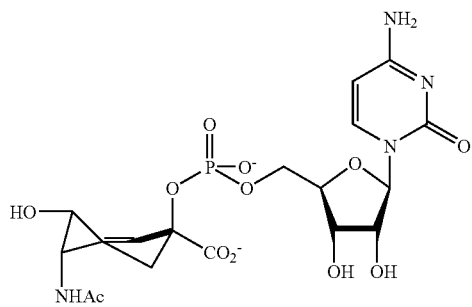 |

TABLE 2-continued

| Compound | Compound structure |
|---|---|
| 49 | 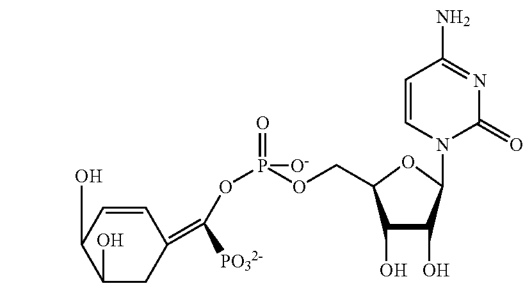 |
| 50 | 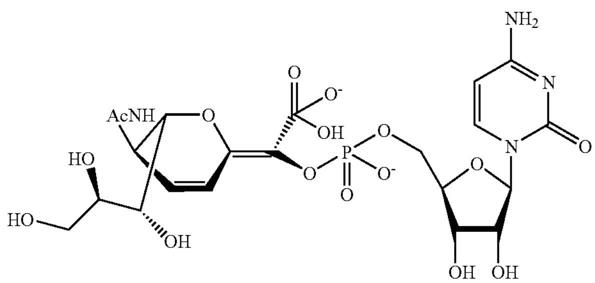 |
| 51 | 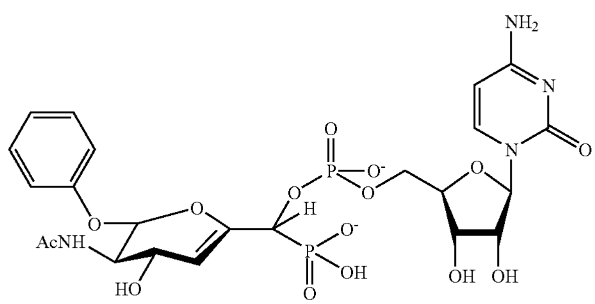 |
| 52 | 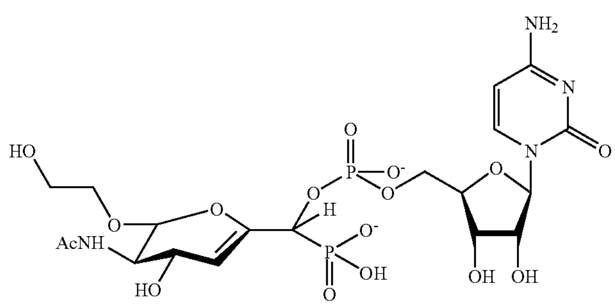 |
| 53 | 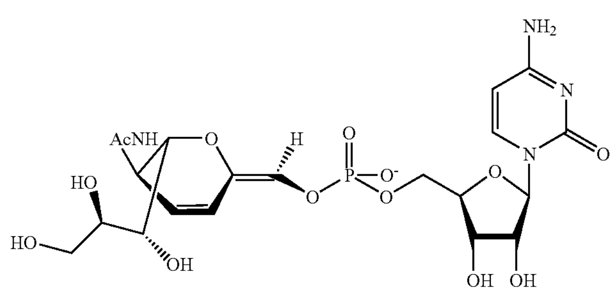 |

TABLE 2-continued

| Compound | Compound structure |
|---|---|
| 54 | 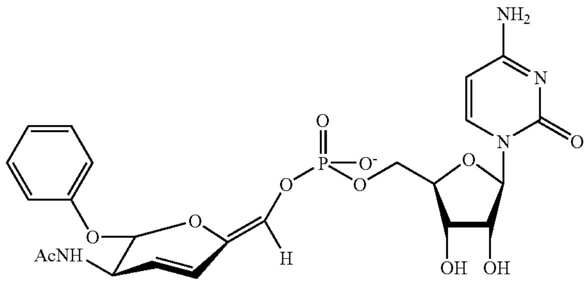 |
| 55 | 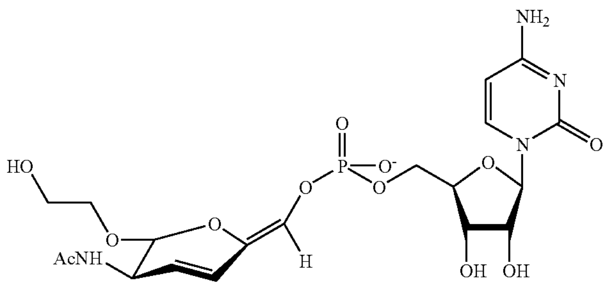 |
| 56 | 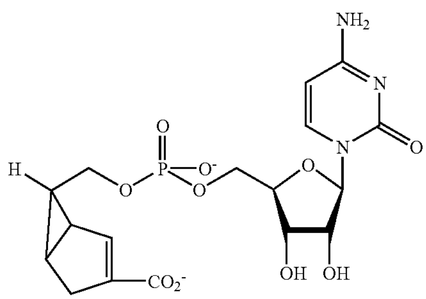 |
| 57 | 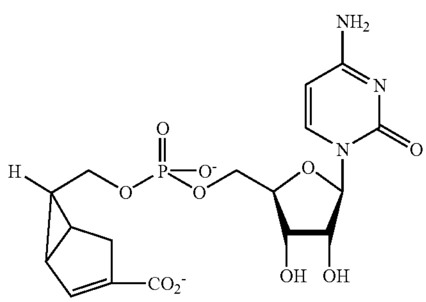 |
| 58 (a to c) | | a: $R^1$ = OH, $R^2$ = H, $R^3$ = OH
b: $R^1$ = NHAc, $R^2$ = OH, $R^3$ = H
c: $R^1$ = NHAc, $R^2$ = H, $R^3$ = OH

TABLE 2-continued

| Compound | Compound structure |
|---|---|
| 59 (a to c) | 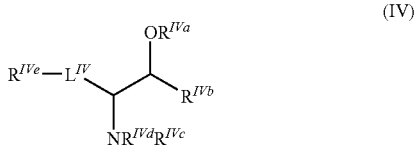<br>a: $R^1 = OH, R^2 = H, R^3 = OH$<br>b: $R^1 = NHAc, R^2 = OH, R^3 = H$<br>c: $R^1 = NHAc, R^2 = H, R^3 = OH$ |
| 60 | 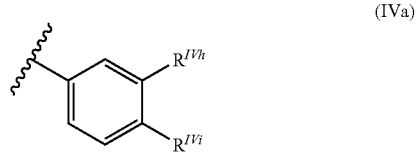 |

In one embodiment the invention provides a compound for use in the treatment of a disease which has a secondary Niemann-Pick type C disease like cellular phenotype, which compound is an inhibitor of sphingolipid biosynthesis of the following formula (IV):

$$R^{IVe}-L^{IV}\underset{NR^{IVd}R^{IVc}}{\overset{OR^{IVa}}{\diagdown}}R^{IVb} \qquad (IV)$$

in which:

$R^{IVa}$ and $R^{IVd}$, which are the same or different, are independently selected from H, substituted or unsubstituted $C_{1-6}$ alkyl or substituted or unsubstituted phenyl;

$R^{IVb}$ is H, substituted or unsubstituted aryl, —CH=CHR$^{IVf}$, or substituted or unsubstituted $C_{1-20}$ alkyl, which $C_{1-20}$ alkyl is optionally interrupted by N(R'), O, S or arylene wherein R' is H, $C_{1-6}$ alkyl or aryl;

$R^{IVc}$ is H, substituted or unsubstituted $C_{1-6}$ alkyl, substituted or unsubstituted phenyl or —C(O)R$^{IVg}$;

$R^{IVf}$ is H or substituted or unsubstituted $C_{1-20}$ alkyl, which $C_{1-20}$ alkyl is optionally interrupted by N(R'), O, S or arylene;

$R^{IVg}$ is H or substituted or unsubstituted $C_{1-20}$ alkyl, which $C_{1-20}$ alkyl is optionally interrupted by N(R'), O, S or arylene;

$R^{IVe}$ is H, hydroxyl, carboxyl, amino, thiol, substituted or unsubstituted $C_{1-20}$ alkyl, substituted or unsubstituted $C_{1-20}$ alkoxy, substituted or unsubstituted aryloxy, acyl, ester, acyloxy, $C_{1-10}$ alkylamino, di($C_{1-10}$)alkylamino, amido, acylamido, —O—$C_{3-25}$ cycloalkyl, —O—$C_{3-20}$ heterocyclyl, substituted or unsubstituted aryl, substituted or unsubstituted $C_{3-20}$ heteroaryl, substituted or unsubstituted $C_{3-25}$ cycloalkyl or substituted or unsubstituted $C_{3-20}$ heterocyclyl, which $C_{1-20}$ alkyl is optionally interrupted by N(R'), O, S or arylene; and $L^{IV}$ is substituted or unsubstituted $C_{1-20}$ alkylene which $C_{1-20}$ alkylene is optionally interrupted by N(R'), O, S or arylene;

or a pharmaceutically acceptable salt thereof.

Typically, $R^{IVa}$ is H. Typically, $R^{IVd}$ is H.

Typically, $R^{IVc}$ is H or —C(O)R$^{IVg}$. More typically, $R^{IVc}$ is —C(O)R$^{IVg}$. Typically, $R^{IVg}$ is unsubstituted $C_{1-20}$ alkyl. $R^{IVg}$ may be, for instance, $C_5H_{11}$, $C_9H_{19}$ or $C_{15}H_{31}$.

Typically $L^{IV}$ is $CH_2$.

Typically, $R^{IVb}$ is —CH=CHR$^{IVf}$. Typically, $R^{IVf}$ is unsubstituted $C_{1-20}$ alkyl. Thus, $R^{IVf}$ may be, for instance, —$C_{13}H_{22}$.

Alternatively, $R^{IVb}$ may be a group of the following formula (IVa):

$$\text{(IVa)}$$

in which $R^{IVh}$ is H, $C_{1-6}$ alkyl, phenyl or, together with $R^{IVi}$ a bidentate group of the structure —O-alk-O—; and $R^{IVi}$ is H, $C_{1-6}$ alkyl, phenyl or, together with $R^{IVh}$ a bidentate group of the structure —O-alk-O—, wherein alk is substituted or unsubstituted $C_{1-6}$ alkylene.

Typically, $R^{IVh}$ is H or, together with $R^{IVi}$ a bidentate group of the structure —O—$CH_2$—$CH_2$—O—. Typically, $R^{IVi}$ is H, OH or, together with $R^{IVh}$ a bidentate group of the structure —O—$CH_2$—$CH_2$—O—. More typically, $R^{IVh}$ is H and $R^{IVi}$ is either H or OH. Alternatively, $R^{IVi}$ and $R^{IVh}$ together form a bidentate group of the structure —O-alk-O—.

Typically, $R^{IVe}$ is substituted or unsubstituted aryl, substituted or unsubstituted $C_{3-20}$ heteroaryl, substituted or unsubstituted $C_{3-25}$ cycloalkyl or substituted or unsubstituted $C_{3-20}$ heterocyclyl. More typically, $R^{IVe}$ is substituted or unsubstituted $C_{3-20}$ heterocyclyl, even more typically a substituted or unsubstituted $C_{4-6}$ heterocyclyl. $R^{IVe}$ may be N-pyrrolidyl or N-morpholinyl, for instance.

Alternatively, $R^{IVe}$ is OH. Typically, when $R^{IVe}$ is OH, $L^{IV}$ is $CH_2$.

Examples of compounds of formula (IV) include D,L-threo-1-phenyl-2-decanoylamino-3-morpholino-1-propanol (PDMP); D,L-threo-1-phenyl-2-hexadecanoylamino-3-morpholino-1-propanol (PPMP); D-threo-1-phenyl-2-palmitoilamino-3-pyrrolidino-1-propanol (P4); 4'-hydroxy-D-threo-1-phenyl-2-palmitoilamino-3-pyrrolidino-1-propanol (4'-hydroxy-P4) and 3',4'-ethylenedioxy-P4 (EtDO-P4). Such compounds are glycosyltransferase inhibitors and derivatives of sphingosine ("lipid mimics").

In one embodiment the invention provides a compound for use in the treatment of a disease which has a secondary Niemann-Pick type C disease like cellular phenotype, which compound is an inhibitor of sphingolipid biosynthesis of the following formula (V):

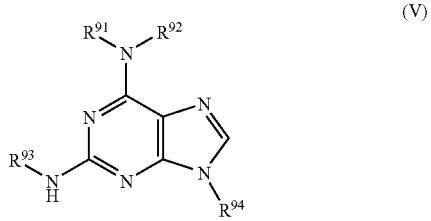

(V)

wherein:

$R^{91}$ and $R^{92}$, which are the same or different, are independently selected from H, substituted or unsubstituted $C_{1-20}$ alkyl, substituted or unsubstituted aryl and $-L^{91}-R^{95}$, wherein $L^{91}$ is substituted or unsubstituted $C_{1-20}$ alkylene, wherein said $C_{1-20}$ alkyl and said $C_{1-20}$ alkylene are optionally interrupted by N(R'), O, S or arylene wherein R' is H, $C_{1-6}$ alkyl or aryl, and wherein $R^{95}$ is substituted or unsubstituted aryl, amino, $C_{1-10}$ alkylamino or di($C_{1-10}$)alkylamino;

$R^{93}$ is $-L^{92}-R^{96}$, wherein $L^{92}$ is a single bond or substituted or unsubstituted $C_{1-20}$ alkylene, which $C_{1-20}$ alkylene is optionally interrupted by N(R'), O, S or arylene, and wherein $R^{96}$ is amido or substituted or unsubstituted aryl; and $R^{94}$ is H or substituted or unsubstituted $C_{1-20}$ alkyl, which $C_{1-20}$ alkyl is optionally interrupted by N(R'), O, S or arylene;

or a pharmaceutically acceptable salt thereof.

Typically, $R^{91}$ is H or $-L^{91}-R^{95}$, wherein $L^{91}$ is unsubstituted $C_{1-10}$ alkylene and $R^{95}$ is amino, $C_{1-10}$ alkylamino or di($C_{1-10}$)alkylamino. More typically, $R^{91}$ is H or $-L^{91}-R^{95}$, wherein $L^{91}$ is unsubstituted $C_{1-4}$ alkylene and $R^{95}$ is amino, $C_{1-10}$ alkylamino or di($C_{1-10}$)alkylamino. Typically, $R^{92}$ is $-L^{91}-R^{95}$, wherein $L^{91}$ is unsubstituted $C_{1-10}$ alkylene and $R^{95}$ is substituted or unsubstituted aryl. More typically, $R^{92}$ is $-L^{91}-R^{95}$, wherein $L^{91}$ is unsubstituted $C_{1-4}$ alkylene and $R^{95}$ is substituted or unsubstituted phenyl. Thus, typically, $R^{91}$ is H and $R^{92}$ is $-C_{1-4}$ alkylene-phenyl, wherein said phenyl is substituted or unsubstituted. Typically said phenyl is unsubstituted or mono-substituted with a halo group, for instance with a chloro or fluoro group. Alternatively, $R^{91}$ is $-L^{91}-R^{95}$, wherein $L^{91}$ is unsubstituted $C_{1-4}$ alkylene and $R^{95}$ is amino, $C_{1-10}$ alkylamino or di($C_{1-10}$)alkylamino and $R^{92}$ is $-C_{1-4}$ alkylene-phenyl, wherein said phenyl is substituted or unsubstituted. Typically said phenyl is unsubstituted or mono-substituted with a halo group, for instance with a chloro or fluoro group.

Typically, $R^{93}$ is $-L^{92}-R^{96}$, wherein $L^{92}$ is unsubstituted $C_{1-10}$ alkylene and $R^{96}$ is amido or substituted or unsubstituted aryl. More typically, $L^{92}$ is methylene or ethylene. More typically, $R^{96}$ is amido or substituted or unsubstituted phenyl. Even more typically, $R^{96}$ is $-C(O)NH_2$ or substituted or unsubstituted phenyl. Typically said phenyl is mono-substituted with a halo group, for instance with a bromo group. Alternatively, said phenyl is unsubstituted.

Typically, $R^{94}$ is $C_{1-10}$ alkyl, which $C_{1-10}$ alkyl is unsubstituted or substituted with a hydroxyl group. More typically $R^{94}$ is selected from methyl, ethyl, propyl, butyl, $CH_2OH$, hydroxy-substituted ethyl, hydroxy-substituted propyl and hydroxy-substituted butyl. Even more typically, $R^{94}$ is methyl or $-CH_2CH_2OH$.

Thus, in one embodiment, $R^{91}$ is H, $-C_{1-4}$ alkylene-amino, $-C_{1-4}$ alkylene-$C_{1-10}$ alkylamino or $-C_{1-4}$ alkylene-di($C_{1-10}$)alkylamino;

$R^{92}$ is $-C_{1-4}$ alkylene-phenyl, wherein said phenyl is substituted or unsubstituted;

$R^{93}$ is $-L^{92}-R^{96}$, wherein $L^{92}$ is unsubstituted $C_{1-10}$ alkylene and $R^{96}$ is amido or substituted or unsubstituted phenyl; and $R^{94}$ is $C_{1-10}$ alkyl, which $C_{1-10}$ alkyl is unsubstituted or substituted with a hydroxyl group.

Table 3 shows examples of compounds of formula (V) which may be employed in the present invention. The compounds in Table 3 are described in Armstrong, J. I. et al., Angew. Chem. Int. Ed. 2000, 39, No. 7, p. 1303-1306.

TABLE 3

| Compound | Compound structure |
|---|---|
| 61 | ![structure] |
| 62 | ![structure] |
| 63 | ![structure] |

TABLE 3-continued

| Compound | Compound structure |
| --- | --- |
| 64 | 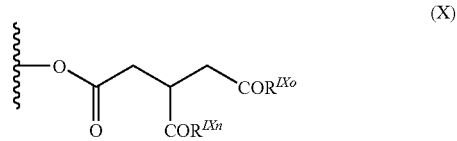 |
| 65 | 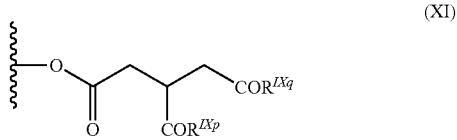 |
| 66 | 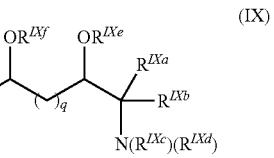 |

In one embodiment the invention provides a compound for use in the treatment of a disease which has a secondary Niemann-Pick type C disease like cellular phenotype, which compound is an inhibitor of sphingolipid biosynthesis of the following formula (IX):

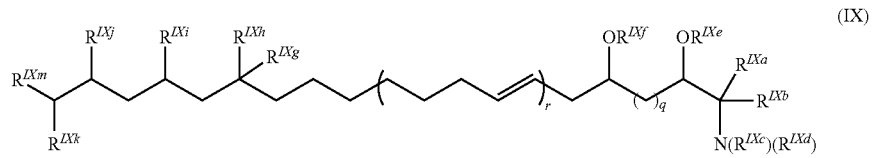

(IX)

in which:

q is 0 or 1;

r is 0 or 1;

$R^{IXa}$ is H, COOH or an unsubstituted or substituted ester;

$R^{IXb}$ is an unsubstituted or substituted $C_{1-6}$ alkyl;

$R^{IXc}$ and $R^{IXd}$, which are the same or different, are each independently selected from H, unsubstituted or substituted $C_{1-6}$ alkyl and unsubstituted or substituted phenyl;

$R^{IXe}$ and $R^{IXf}$, which are the same or different, are each independently selected from H, unsubstituted or substituted $C_{1-6}$ alkyl, unsubstituted or substituted phenyl and unsubstituted or substituted acyl;

either (a) one of $R^{IXg}$ and $R^{IXh}$ is H and the other is $OR^{IXr}$, wherein $R^{IXr}$ is selected from H, unsubstituted or substituted $C_{1-6}$ alkyl, unsubstituted or substituted phenyl and unsubstituted or substituted acyl, or (b) $R^{IXg}$ and $R^{IXh}$ together form an oxo group;

$R^{IXi}$ is H, unsubstituted or substituted $C_{1-6}$ alkyl, unsubstituted or substituted $C_{1-6}$ alkoxy and unsubstituted or substituted phenyl;

$R^{IXj}$ is H, unsubstituted or substituted $C_{1-6}$ alkyl or a group of the following formula (X):

$$\text{(X)}$$

in which $R^{IXn}$ and $R^{IXo}$, which are the same or different, are each independently selected from OH, unsubstituted or substituted $C_{1-6}$ alkoxy, unsubstituted or substituted phenoxy, amino, unsubstituted or substituted $C_{1-6}$ alkylamino and unsubstituted or substituted di($C_{1-6}$)alkylamino;

$R^{IXk}$ is H, unsubstituted or substituted $C_{1-6}$ alkyl or a group of the following formula (XI):

$$\text{(XI)}$$

in which $R^{IXp}$ and $R^{IXq}$, which are the same or different, are each independently selected from OH, unsubstituted or substituted $C_{1-6}$ alkoxy, unsubstituted or substituted phenoxy, amino, unsubstituted or substituted $C_{1-6}$ alkylamino and unsubstituted or substituted di($C_{1-6}$)alkylamino; and $R^{IXm}$ is selected from H and unsubstituted or substituted $C_{1-20}$ alkyl, which $C_{1-20}$ alkyl is optionally interrupted by N(R'), O, S or phenylene, wherein R' is H, $C_{1-6}$ alkyl or phenyl;

or a pharmaceutically acceptable salt thereof.

In one embodiment, r is 0 and q is 1. Typically, in that embodiment, $R^{IXb}$ is unsubstituted $C_{1-6}$ alkyl. More typically, $R^{IXb}$ is methyl. Furthermore, $R^{IXa}$ is typically H. Usually $R^{IXc}$ and $R^{IXd}$ are independently selected from H and unsubstituted $C_{1-6}$ alkyl. More typically, however, $R^{IXc}$ and $R^{IXd}$ are both H. Typically, $R^{IXe}$ and $R^{IXf}$ are independently selected from H and unsubstituted $C_{1-6}$ alkyl. More typically, $R^{IXe}$ and $R^{IXf}$ are both H. Usually, one of $R^{IXg}$ and $R^{IXh}$ is H and the other is $OR^{IXr}$, wherein $R^{IXr}$ is selected from H and unsubstituted $C_{1-6}$ alkyl. More typically, however, one of $R^{IXg}$ and $R^{IXh}$ is H and the other is OH. $R^{IXi}$ is typically unsubstituted $C_{1-6}$ alkyl, more typically methyl. Typically, $R^{IXj}$ is a group of formula (X). Usually, $R^{IXk}$ is a group of formula (XI). Typically, $R^{IXn}$, $R^{IXo}$, $R^{IXp}$ and $R^{IXq}$, which are the same or different, are independently selected from H and unsubstituted $C_{1-6}$ alkyl. More typically, each of $R^{IXn}$, $R^{IXo}$, $R^{IXp}$ and $R^{IXq}$ is H. $R^{IXm}$ is typically selected from unsubstituted or substituted $C_{1-10}$ alkyl. More typically, $R^{IXm}$ is an unsubstituted or substituted $C_{1-6}$ alkyl. $R^{IXm}$ may be, for instance, —CH(CH$_3$)(C$_4$H$_{11}$).

In another embodiment, r is 1 and q is 0. Typically, in this embodiment, $R^{IXb}$ is $C_{1-6}$ alkyl substituted with a hydroxyl group. More typically, $R^{IXb}$ is CH$_2$OH. Furthermore, $R^{IXa}$ is typically COOH or an unsubstituted ester. More typically, $R^{IXa}$ is COOH. Usually $R^{IXc}$ and $R^{IXd}$ are independently selected from H and unsubstituted $C_{1-6}$ alkyl. More typically, however, $R^{IXc}$ and $R^{IXd}$ are both H. Typically, $R^{IXe}$ and $R^{IXf}$ are independently selected from H and unsubstituted $C_{1-6}$ alkyl. More typically, $R^{IXe}$ and $R^{IXf}$ are both H. Usually, in this embodiment, $R^{IXg}$ and $R^{IXh}$ together form an oxo group. $R^{IXi}$ is typically H. Typically, in this embodiment, $R^{IXj}$ and $R^{IXk}$, which may be the same or different, are independently selected from H and unsubstituted $C_{1-6}$ alkyl. More typically, $R^{IXj}$ and $R^{IXk}$ are both H. $R^{IXm}$ is typically, in this embodiment, selected from unsubstituted or substituted $C_{1-6}$ alkyl. More typically, $R^{IXm}$ is an unsubstituted $C_{1-6}$ alkyl. $R^{IXm}$ may be, for instance, methyl.

Table 4 shows examples of compounds of formula (IX) which may be employed in the present invention. Such compounds are inhibitors of ceramide biosynthesis. More specifically, compound 67 (Myriocin) is a serine palmitoyltransferase inhibitor and compound 68 (Fumonisin) is a dihydroceramide synthase inhibitor.

unsubstituted $C_{1-20}$ alkylene-$C_{3-20}$ heteroaryl, substituted or unsubstituted $C_{1-20}$ alkylene-$C_{3-25}$ cycloalkyl, substituted or unsubstituted $C_{1-20}$ alkylene-$C_{3-20}$ heterocyclyl, substituted or unsubstituted $C_{1-20}$ alkylene-O—$C_{3-20}$ heterocyclyl, substituted or unsubstituted aryl, substituted or unsubstituted $C_{3-20}$ heteroaryl, substituted or unsubstituted $C_{3-25}$ cycloalkyl or substituted or unsubstituted $C_{3-20}$ heterocyclyl wherein said $C_{1-20}$ alkyl and $C_{1-20}$ alkylene are optionally interrupted by N(R'), O, S or arylene wherein R' is H, $C_{1-6}$ alkyl or aryl; and $R^{Xb}$ and $R^{Xc}$, which are the same or different, are independently selected from H, unsubstituted or substituted $C_{1-10}$ alkyl and unsubstituted or substituted aryl;

or a pharmaceutically acceptable salt thereof.

Typically, $R^{Xa}$ is H, substituted or unsubstituted $C_{1-10}$ alkyl or substituted or unsubstituted phenyl. More typically, $R^{Xa}$ is H, unsubstituted $C_{1-6}$ alkyl or unsubstituted phenyl. Even more typically, $R^{Xa}$ is H.

Typically, $R^{Xb}$ and $R^{Xc}$, which are the same or different, are independently selected from H, unsubstituted $C_{1-6}$ alkyl and unsubstituted phenyl. More typically, $R^{Xb}$ and $R^{Xc}$ are both H.

Table 5 shows an example of a compound of formula (XII) which may be employed in the present invention. The com-

TABLE 4

| Compound | Compound structure (name) |
|---|---|
| 67 | 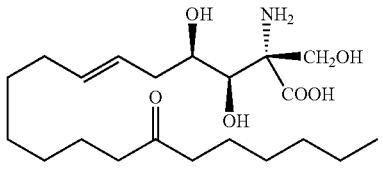<br>(Myriocin) |
| 68 | 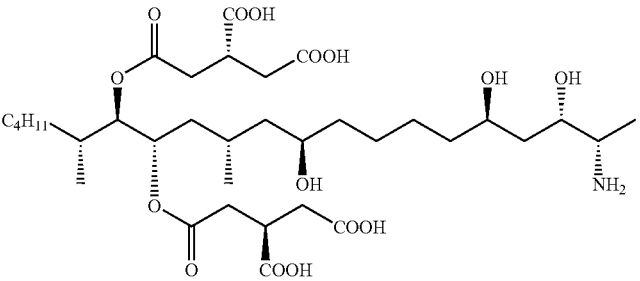<br>(Fumonisin) |

In one embodiment the invention provides a compound for use in the treatment of a disease which has a secondary Niemann-Pick type C disease like cellular phenotype, which compound is an inhibitor of sphingolipid biosynthesis of the following formula (XII):

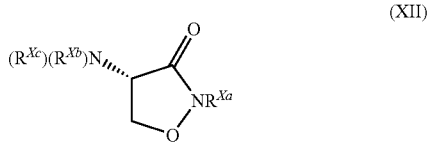

(XII)

in which:

$R^{Xa}$ is H, substituted or unsubstituted $C_{1-20}$ alkyl, substituted or unsubstituted $C_{1-20}$ alkylene-aryl, substituted or pound (compound 69) is an inhibitor of ceramide biosynthesis. More specifically, compound 69 (L-Cycloserine) is a serine palmitoyltransferase inhibitor.

TABLE 5

| Compound | Compound structure (name) |
|---|---|
| 69 | 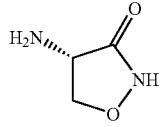<br>(L-Cycloserine) |

Diseases which have a secondary Niemann-Pick type C disease like cellular phenotype can be treated with an inhibitor of sphingolipid biosynthesis in accordance with the present invention.

Niemann-Pick Type C Disease

Niemann-Pick type C disease is characterised by massive accumulation of cholesterol, particularly in peripheral tissues, and historically it has been viewed as a cholesterol storage disease (Traffic 2000; 1(3):218-25; J Cell Biol 1989; 108(5):1625-36). There is increasing evidence that the other storage lipids, including glycosphingolipids (GSLs) might play a role in this disease, and particularly in the brain (J Biol Chem 2004; 279(25):26167-75; Curr Biol 2001; 11(16):1283-7). The primary biochemical problem in NPC disease is unknown. Most commonly this disease results from mutations in the NPC1 protein, a transmembrane protein of, late endosomes/lysosomes (LE/Lys) (Traffic 2000; 1(3):218-25). The disease can be induced in tissue culture cells by treating healthy cells with a secondary amphiphile, which either directly or indirectly inhibits the function of NPC1 (J Biol Chem 2004; 279(25):26167-75; J Biol Chem 2000; 275 (23):17468-75).

Figure 3:
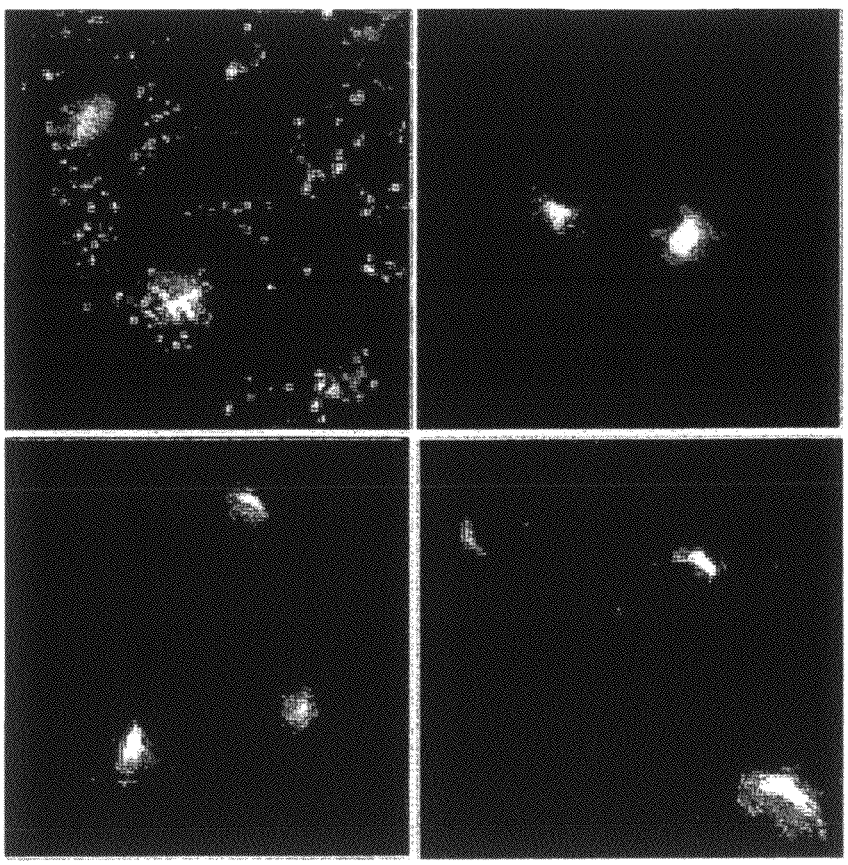
FIG. 3 shows that glycosphingolipid (GSL) storage and abnormal transport in Niemann-Pick C1 disease can be corrected by treatment with NB-DGJ.
Figure 3:
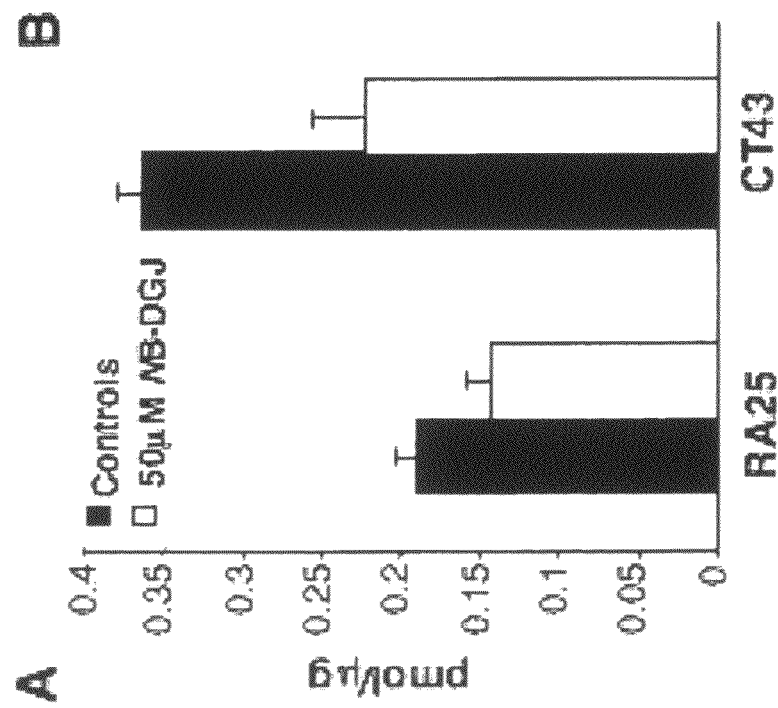

It has been shown that Niemann-Pick C1 cells (NPC1 null CHO cells) and normal cells treated with amphiphiles to induce an NPC1 phenotype, in addition to free cholesterol storage, have glycosphingolipid (GSL) storage (FIG. 3A) and abnormalities in endocytic transport (FIG. 3B) including defective early to late endosomal transport and late endosomal to Golgi transport (J Biol Chem 2004; 279(25):26167-75). NPC1 cells have a 2-fold increase in total GSLs (HPLC quantified) compared to controls (FIG. 3A). Treatment of NPC1 cells with NB-DNJ (miglustat; an approved drug for the treatment of type 1 Gaucher disease), an inhibitor of ceramide glucosyltransferase and therefore of sphingolipid biosynthesis (Philos Trans R Soc Lond B Biol Sci 2003; 358(1433):947-54), leads to a subsequent reduction in GSL storage in the endo/lysosomal system, which corrects abnormal endocytosis (FIG. 3B) (J Biol Chem 2004; 279(25): 26167-75). The reduction in endogenous GSL biosynthesis lowers GSL storage in NPC1 cells to control levels (FIG. 3A). This correction in GSL levels is associated with a correction in endocytic transport defects (J Biol Chem 2004; 279(25): 26167-75). Fluorescently labelled lactosylceramide (BODIPY-LacCer), a GSL normally transported through the endocytic system to the Golgi (FIG. 3Bi), is misdirected to the LE/Lys system in untreated NPC1 cells (FIG. 3Bii), indicative of GSL storage (J Biol Chem 2004; 279(25):26167-75; J Biol Chem 2003; 278(23):20961-70; Am J Hum Genet 2001; 68(6):1361-72). A correction in BODIPY-LacCer transport to the Golgi in NPC1 cells treated with NB-DGJ (FIG. 3B iv), suggests defective endocytic transport can be corrected if excessive GSL storage is reduced in NPC1 cells.

The findings from the NPC1 mouse study provided the impetus for the evaluation of miglustat in an NPC patient (R. H. Lachmann et al., 2004). Peripheral blood B cells were isolated from the patient at time intervals spanning 6 months. B cells were selected as they are a homogeneous resting cell population that are readily purified making comparisons over time on a single patient and between patients possible. In NPC disease several cell biological abnormalities are known. These include GSL accumulation (Vanier & Millat, 2003), altered GSL trafficking (Puri et al., 1999; te Vruchte et al., 2004), reduced endosomal uptake of fluid phase makers (Mayran, Parton, & Gruenberg, 2003) and expansion of the late endosomal/lysosomal compartment. In the NPC patient treated with miglustat pathological lipid storage was reduced, the total late endosomal/lysosomal compartment was almost normalised, improved endosomal uptake was observed and lipid trafficking in peripheral blood B lymphocytes was greatly improved (R. H. Lachmann et al., 2004). The demonstration that treatment with miglustat, which has no direct effect on cholesterol metabolism, corrected the abnormal lipid trafficking seen in B lymphocytes in NPC indicates that GSL accumulation is a significant pathogenic mechanism in NPC. Although this study does not reveal the status of storage and pathology in the brain it serves to illustrate those key disease parameters attributable to NPC disease can be improved in peripheral cells. Long-term follow-up and clinical and biochemical monitoring of this patient is ongoing (R. H. Lachmann et al., 2004).

A clinical trial in NPC patients in centres in the UK and USA has subsequently been performed to evaluate clinical efficacy. Interim data published after 12 months of a 2-year trial demonstrated benefit (stabilization or improvement in saccadic eye movement) (Patterson et al., 2006). These findings therefore hold promise for the use of miglustat in the clinical management of NPC patients in the future.

Diseases which have a Secondary Niemann-Pick Type C (NPC) Disease Like Cellular Phenotype The findings presented in the Examples below evidence that the accumulation in Smith-Lemli-Opitz Syndrome (SLOS) cells of the class II amphiphile 7-DHC causes abnormal sphingolipid storage and transport in the LE/Lys system, and that the treatment of such cells with an inhibitor of sphingolipid biosynthesis corrects these abnormalities.

These findings suggest that if a secondary biomolecule (a class 2 amphiphile, for instance) is generated as part of a pathogenic cascade of a disease, which biomolecule results in an NPC disease like cellular phenotype, Substrate Reduction Therapy (SRT), using an inhibitor of sphingolipid biosynthesis, will show benefit in treating that disease. In particular, the findings support that inhibitors of sphingolipid biosynthesis can ameliorate intracellular cholesterol transport defects associated with diseases which have a secondary Niemann-Pick type C disease like cellular phenotype, e.g. SLOS, irrespective of the mechanism that causes them.

Accordingly, diseases which have a secondary Niemann-Pick type C disease like cellular phenotype can be treated with an inhibitor of sphingolipid biosynthesis in accordance with the present invention.

Primary Niemann-Pick type C (NPC) disease is thought to involve a mutation in either the NPC1 or NPC2 gene. However, the term "a disease which has a secondary Niemann-Pick type C disease like cellular phenotype", as used herein, generally refers to any disease which does not involve a mutation in either the NPC1 gene or the NPC2 gene and which involves:

a mutation in a gene other than NPC1 or NPC2;
an alteration in the function of a protein other than NPC1 protein or NPC2 protein; or
a process that causes mislocalisation of NPC1 protein or NPC2 protein, wherein said mutation of the gene other than NPC1 or NPC2, said alteration in the function of the protein other than NPC1 protein or NPC2 protein, or said mislocalisation of NPC1 protein or NPC2 protein, results in a Niemann-Pick disease type C like cellular phenotype.

Typically, the disease which has a secondary Niemann-Pick type C (NPC) disease like cellular phenotype is a disease which does not involve a mutation in either the NPC1 gene or the NPC2 gene but which incurs the accumulation of a biomolecule, the accumulation of which in turn induces a Niemann-Pick type C disease like cellular phenotype. Usually, the biomolecule is a class II amphiphile. A class II amphiphile is a detergent-like molecule which is, typically, capable of altering the stability of the lysosome. Typically, the class II amphiphile is 7-DHC. Alternatively, the class II amphiphile may be U18666A, 7-ketocholesterol, progesterone or imipramine, all of which are steroids or steroid analogues known to induce free cholesterol storage and abnormal lipid endocytosis. More typically, the biomolecule is a class II amphiphile which is a precursor or analogue of cholesterol. Thus the biomolecule may, for instance, be 7-DHC.

Alternatively, the term "a disease which has a secondary Niemann-Pick type C disease like cellular phenotype", as used herein, generally refers to any disease which involves a mutation in a gene other than NPC1 or NPC2, or which involves an alteration in the function of a protein other than NPC1 protein or NPC2 protein, wherein that gene other than NPC1 or NPC2 or that protein other than NPC1 protein or NPC2 protein, or any metabolite thereof, results in a cellular NPC phenotype.

Alternatively or in addition, the term "disease which has a secondary Niemann-Pick type C disease like cellular phenotype", as used herein, may be defined to mean any disease which incurs the accumulation of a biomolecule, the accumulation of which in turn induces a Niemann-Pick type C disease like cellular phenotype. Usually, the biomolecule is a class II amphiphile. A class II amphiphile is a detergent-like molecule which is, typically, capable of altering the stability of the lysosome.

In one embodiment, therefore, the disease which has a secondary Niemann-Pick type C disease like cellular phenotype is a disease which incurs the accumulation of a class II amphiphile.

The invention therefore further provides the use of an inhibitor of sphingolipid biosynthesis in the manufacture of a medicament for the treatment of a disease which incurs the accumulation of a class II amphiphile.

Typically, the class II amphiphile is 7-DHC. Alternatively, the class II amphiphile may be U18666A, 7-ketocholesterol, progesterone or imipramine, all of which are steroids or steroid analogues known to induce free cholesterol storage and abnormal lipid endocytosis.

More typically, the biomolecule is a class II amphiphile which is a precursor or analogue of cholesterol. Thus the biomolecule may be, for instance, 7-DHC.

The term "Niemann-Pick type C disease like cellular phenotype", as used herein, means a cellular phenotype which includes: (a) abnormal cholesterol metabolism and trafficking; (b) abnormal sphingolipid storage and trafficking; and (c) defective endocytosis. Typically, the abnormal sphingolipid storage (b) involves the majority of sphingolipids in the cell being present at abnormally elevated levels. Typically, (c) comprises defective endocytosis of substantially all biomolecules in the endocytic pathway, including lipids and biomolecules other than lipids, for instance proteins.

Diseases which have a secondary Niemann-Pick type C disease like cellular phenotype which can be treated in accordance with the present invention include, but are not limited to, the following conditions:
  Smith-Lemli-Opitz Syndrome (SLOS);
  other inborn errors of cholesterol synthesis, CHILD syndrome (NSDHL, sterol isomerase), XLD chondrodysplasia punctata type 2 or Conradi-Hünnermann-Happle syndrome (sterol isomerase) and HEM dysplasia;
  Tangier disease—(Neufeld, E. B., et al., J. Biol. Chem., 2004, 279:15571-8);
  Huntington's disease—(Truchina, E., et al., Hum. Mol. Genet., 2006, 15:3578-91);
  Cystic Fibrosis—(Gentzsch, M., et al., J. Cell. Sci., 2007, 120:447-455);
  Pelizaeus-Merzbacher disease—(Simons, M., et al., J. Cell. Biol., 2002, 157:327-36);
  Mucolipidosis II (Icell)—(Inui, K., et al., Biochem. Int., 1989, 18:1129-35); and
  variant late infantile-Neuronal Ceroid Lipofuscinosis—(Teixeira, C. A., et al., Biochem. Biophys. Acta., 2006, 1762:637-46).

The disease which has a secondary Niemann-Pick type C disease like cellular phenotype may be a disorder which alters the activity of an enzyme involved in cholesterol synthesis. There is also an association between SLOS, altered cholesterol metabolism and autism.

Typically, therefore, the disease which has a secondary Niemann-Pick type C disease like cellular phenotype is selected from Smith-Lemli-Opitz Syndrome, an inborn error of cholesterol synthesis, CHILD syndrome, XLD chondrodysplasia punctata type 2, Conradi-Hünnermann-Happle syndrome, HEM dysplasia, Tangier disease, Huntington's disease, Cystic Fibrosis, Pelizaeus-Merzbacher disease, Mucolipidosis II (Icell), variant late infantile-Neuronal Ceroid Lipofuscinosis and a disorder which alters the activity of an enzyme involved in cholesterol synthesis or homeostasis, for instance autism.

More typically, the disease which has a secondary Niemann-Pick type C disease like cellular phenotype is Smith-Lemli-Opitz Syndrome (SLOS).

Typically, the disease which has a secondary Niemann-Pick type C disease like cellular phenotype is other than mucopolysaccharidosis. The term "mucopolysaccharidosis", as used herein includes all the mucopolysaccharidoses, including mucopolysaccharidosis types I, II, III, IV, V, VI and VII.

In one embodiment, the disease which has a secondary Niemann-Pick type C disease like cellular phenotype can be Mucolipidosis IV (Soyombo A A, et al. J. Biol. Chem., 2006, 281:7294-301). Thus, in one embodiment the disease which has a secondary Niemann-Pick type C disease like cellular phenotype is selected from Smith-Lemli-Opitz Syndrome, an inborn error of cholesterol synthesis, CHILD syndrome, XLD chondrodysplasia punctata type 2, Conradi-Hünnermann-Happle syndrome, HEM dysplasia, Tangier disease, Huntington's disease, Cystic Fibrosis, Pelizaeus-Merzbacher disease, Mucolipidosis II (Icell), Mucolipidosis IV, variant late infantile-Neuronal Ceroid Lipofuscinosis and a disorder which alters the activity of an enzyme involved in cholesterol synthesis or homeostasis, for instance autism.

More typically, however, the disease which has a secondary Niemann-Pick type C disease like cellular phenotype is other than mucopolysaccharidosis and other than mucolipidosis IV.

One potential therapy for SLOS patients is to increase dietary cholesterol to compensate for an endogenous block in cholesterol biosynthesis. Thus far, however, this therapy has produced only limited clinical benefit in SLOS patients because, owing to the endosomal accumulation and defective endocytic trafficking of free cholesterol, such patients have been unable to fully utilize dietary cholesterol supplementation.

It is a finding of the present invention, however, that inhibitors of sphingolipid biosynthesis can ameliorate intracellular cholesterol transport defects associated with SLOS; the use of an inhibitor of sphingolipid biosynthesis is therefore likely to increase the patients' utilisation of dietary cholesterol. SLOS can therefore be treated with an inhibitor of sphingolipid biosynthesis either alone or in combination with cholesterol.

Typically, the inhibitor of sphingolipid biosynthesis is NB-DNJ. Thus, SLOS may be treated using NB-DNJ alone or a combination of NB-DNJ and cholesterol.

Accordingly, in one embodiment, the invention provides a product which comprises (a) a compound which is an inhibitor of sphingolipid biosynthesis and (b) cholesterol, for simultaneous, separate or sequential use in the treatment of SLOS.

The invention also provides a compound which is an inhibitor of sphingolipid biosynthesis for use in the treatment of SLOS by coadministration with cholesterol.

The invention also provides cholesterol for use in the treatment of SLOS by coadministration with a compound which is an inhibitor of sphingolipid biosynthesis.

The invention also provides the use of (a) a compound which is an inhibitor of sphingolipid biosynthesis in the manufacture of a medicament for the treatment of SLOS by coadministration with (b) cholesterol.

The invention further provides the use of (b) cholesterol in the manufacture of a medicament for the treatment of SLOS by coadministration with (a) a compound which is an inhibitor of sphingolipid biosynthesis.

The invention further provides the use of (a) a compound which is an inhibitor of sphingolipid biosynthesis and (b) cholesterol in the manufacture of a medicament for the treatment of SLOS.

The invention also provides a method of treating SLOS which method comprises administering to a patient in need of such treatment an effective amount of a compound which is an inhibitor of sphingolipid biosynthesis and an effective amount of cholesterol.

The invention also provides a pharmaceutical composition for use in treating SLOS comprising a pharmaceutically acceptable carrier or diluent, cholesterol and a compound which is an inhibitor of sphingolipid biosynthesis.

SLOS may be treated using a combination of (a) an inhibitor of sphingolipid biosynthesis and (b) an inhibitor of de novo cholesterol biosynthesis. Typically, the inhibitor of de novo cholesterol biosynthesis is a statin, for instance simvastatin, pravastatin, lovastatin, fluvastatin, cerivastatin or atorvastatin. More typically, the inhibitor of de novo cholesterol biosynthesis is simvastatin. Simvastatin may be used to lower 7-DHC levels by inhibiting de novo sterol synthesis and/or upregulating DHCR7 expression (Wassif et al., Mol Genet Metab. 85: 96-107).

The inhibitor of de novo cholesterol biosynthesis, for instance a statin, must be administered at an appropriate dose because high doses of such inhibitors have been shown to be detrimental and statin therapy (0.5-1.0 mg/kg/d) is limited to SLOS patients with significant residual enzymatic function (mild to classical phenotypes) (Wassif et al. Mol Genet Metab. 85: 96-107; Stark et al Am J Med Genet 113:183-189). Typically, therefore, the dose of the inhibitor of de novo cholesterol biosynthesis is from 0.5 to 1.0 mg/kg/day.

Accordingly, in one embodiment, the invention provides a product which comprises (a) a compound which is an inhibitor of sphingolipid biosynthesis and (b) an inhibitor of de novo cholesterol biosynthesis, for simultaneous, separate or sequential use in the treatment of SLOS.

The invention also provides a compound which is an inhibitor of sphingolipid biosynthesis for use in the treatment of SLOS by coadministration with an inhibitor of de novo cholesterol biosynthesis.

The invention also provides an inhibitor of de novo cholesterol biosynthesis for use in the treatment of SLOS by coadministration with a compound which is an inhibitor of sphingolipid biosynthesis.

The invention also provides the use of (a) a compound which is an inhibitor of sphingolipid biosynthesis in the manufacture of a medicament for the treatment of SLOS by coadministration with (b) an inhibitor of de novo cholesterol biosynthesis.

The invention further provides the use of (b) an inhibitor of de novo cholesterol biosynthesis in the manufacture of a medicament for the treatment of SLOS by coadministration with (a) a compound which is an inhibitor of sphingolipid biosynthesis.

The invention further provides the use of (a) a compound which is an inhibitor of sphingolipid biosynthesis and (b) an inhibitor of de novo cholesterol biosynthesis in the manufacture of a medicament for the treatment of SLOS.

The invention also provides a method of treating SLOS, which method comprises administering to a patient in need of such treatment an effective amount of a compound which is an inhibitor of sphingolipid biosynthesis and an effective amount of an inhibitor of de novo cholesterol biosynthesis.

The invention also provides a pharmaceutical composition for use in treating SLOS comprising a pharmaceutically acceptable carrier or diluent, an inhibitor of de novo cholesterol biosynthesis and a compound which is an inhibitor of sphingolipid biosynthesis.

Typically, the inhibitor of sphingolipid biosynthesis is NB-DNJ.

SLOS may be treated using a combination of (a) an inhibitor of sphingolipid biosynthesis, (b) cholesterol and (c) an inhibitor of de novo cholesterol biosynthesis. Such a therapy combines increasing exogenously delivered cholesterol and increasing the patients' ability to utilize that cholesterol by administration of an inhibitor of sphingolipid biosynthesis, whilst lowering 7-DHC levels by inhibiting de novo cholesterol synthesis. Typically, the inhibitor of de novo cholesterol biosynthesis is a statin, for instance simvastatin, pravastatin, lovastatin, fluvastatin, cerivastatin or atorvastatin. More typically, the inhibitor of de novo cholesterol biosynthesis is simvastatin.

The inhibitor of de novo cholesterol biosynthesis, for instance a statin, must be administered at an appropriate dose because high doses of such inhibitors have been shown to be detrimental in some cases of SLOS (Stark et al Am J Med Genet 113:183-189; Hass (2007) J inherit Metab Dis 30:375-387). Typically, therefore, the dose of the inhibitor of de novo cholesterol biosynthesis is from 0.5 to 1.0 mg/kg/day.

Accordingly, in one embodiment, the invention provides a product which comprises (a) a compound which is an inhibitor of sphingolipid biosynthesis, (b) cholesterol and (c) an inhibitor of de novo cholesterol biosynthesis, for simultaneous, separate or sequential use in the treatment of SLOS.

The invention also provides a compound which is an inhibitor of sphingolipid biosynthesis for use in the treatment of SLOS by coadministration with an inhibitor of de novo cholesterol biosynthesis and cholesterol.

The invention also provides an inhibitor of de novo cholesterol biosynthesis for use in the treatment of SLOS by coadministration with cholesterol and a compound which is an inhibitor of sphingolipid biosynthesis.

The invention also provides cholesterol for use in the treatment of SLOS by coadministration with an inhibitor of de novo cholesterol biosynthesis and a compound which is an inhibitor of sphingolipid biosynthesis.

The invention also provides the use of (a) a compound which is an inhibitor of sphingolipid biosynthesis in the manufacture of a medicament for the treatment of SLOS by coadministration with (b) cholesterol and (c) an inhibitor of de novo cholesterol biosynthesis.

The invention further provides the use of (b) cholesterol in the manufacture of a medicament for the treatment of SLOS by coadministration with (a) a compound which is an inhibitor of sphingolipid biosynthesis and (c) an inhibitor of de novo cholesterol biosynthesis.

The invention further provides the use of (c) an inhibitor of de novo cholesterol biosynthesis in the manufacture of a medicament for the treatment SLOS by coadministration with (a) a compound which is an inhibitor of sphingolipid biosynthesis and (b) cholesterol.

The invention further provides the use of (a) a compound which is an inhibitor of sphingolipid biosynthesis, (b) cholesterol and (c) an inhibitor of de novo cholesterol biosynthesis in the manufacture of a medicament for the treatment of SLOS.

The invention also provides a method of treating SLOS, which method comprises administering to a patient in need of such treatment an effective amount of a compound which is an inhibitor of sphingolipid biosynthesis, an effective amount of cholesterol and an effective amount of an inhibitor of de novo cholesterol biosynthesis.

The invention also provides a pharmaceutical composition for use in treating SLOS, comprising a pharmaceutically acceptable carrier or diluent, cholesterol, an inhibitor of de novo cholesterol biosynthesis and a compound which is an inhibitor of sphingolipid biosynthesis.

Typically, the inhibitor of sphingolipid biosynthesis is NB-DNJ.

An compound which is an inhibitor of sphingolipid biosynthesis, for use in accordance with the present invention, can be administered in a variety of dosage forms, for example orally such as in the form of tablets, capsules, sugar- or film-coated tablets, liquid solutions or suspensions or parenterally, for example intramuscularly, intravenously or subcutaneously. The compound may therefore be given by injection or infusion.

The compound which is an inhibitor of sphingolipid biosynthesis may be presented for administration in a liposome. Thus, the compound may be encapsulated or entrapped in the liposome and then administered to the patient to be treated. Active ingredients encapsulated by liposomes may reduce toxicity, increase efficacy, or both. Notably, liposomes are thought to interact with cells by stable absorption, endocytosis, lipid transfer, and fusion (R. B. Egerdie et al., 1989, J. Urol. 142:390). Drug delivery via liposomes is a well-explored approach for the delivery of iminosugars. Costin G E, Trif M, Nichita N, Dwek R A, Petrescu S M *Biochem Biophys Res Commun.* 2002 May 10; 293(3):918-23 describes the use of liposomes composed of dioleoylphosphatidylethanolamine and cholesteryl hemisuccinate for the delivery of NB-DNJ. In that study, the use of liposomes reduced the required dose of NB-DNJ by a factor of 1000, indicating that liposomes are efficient carriers for iminosugar delivery in mammalian cells.

The dosage depends on a variety of factors including the age, weight and condition of the patient and the route of administration. Daily dosages can vary within wide limits and will be adjusted to the individual requirements in each particular case. Typically, however, the dosage adopted for each route of administration when a compound is administered alone to adult humans is 0.0001 to 50 mg/kg, most commonly in the range of 0.001 to 10 mg/kg, body weight, for instance 0.01 to 1 mg/kg. Such a dosage may be given, for example, from 1 to 5 times daily. For intravenous injection a suitable daily dose is from 0.0001 to 1 mg/kg body weight, preferably from 0.0001 to 0.1 mg/kg body weight. A daily dosage can be administered as a single dosage or according to a divided dose schedule.

Typically a dose to treat human patients may range from about 0.1 mg to about 1000 mg of a compound for use in accordance with the invention, more typically from about 10 mg to about 1000 mg of a compound for use in accordance with the invention. A typical dose may be about 100 mg to about 300 mg of the compound. A dose may be administered once a day (QID), twice per day (BID), or more frequently, depending on the pharmacokinetic and pharmacodynamic properties, including absorption, distribution, metabolism, and excretion of the particular compound. In addition, toxicity factors may influence the dosage and administration regimen. When administered orally, the pill, capsule, or tablet may be ingested daily or less frequently for a specified period of time. The regimen may be repeated for a number of cycles of therapy.

A compound is formulated for use as a pharmaceutical composition also comprising a pharmaceutically acceptable carrier or diluent. The compositions are typically prepared following conventional methods and are administered in a pharmaceutically suitable form. The compound may be administered in any conventional form, for instance as follows:

A) Orally, for example, as tablets, coated tablets, dragees, troches, lozenges, aqueous or oily suspensions, liquid solutions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of sweetening agents, flavouring agents, colouring agents and preserving agents in order to provide pharmaceutically elegant and palatable preparations.

Tablets contain the active ingredient in admixture with non-toxic pharmaceutically acceptable excipients which are suitable for the manufacture of tablets. These excipients may be for example, inert diluents, such as calcium carbonate, sodium carbonate, lactose, dextrose, saccharose, cellulose, corn starch, potato starch, calcium phosphate or sodium phosphate; granulating and disintegrating agents, for example, maize starch, alginic acid, alginates or sodium starch glycolate; binding agents, for example starch, gelatin or acacia; lubricating agents, for example silica, magnesium or calcium stearate, stearic acid or talc; effervescing mixtures; dyestuffs, sweeteners, wetting agents such as lecithin, polysorbates or lauryl sulphate. The tablets may be uncoated or they may be coated by known techniques to delay disintegration and adsorption in the gastrointestinal tract and thereby provide a sustained action over a longer period. For example, a time delay material such as glyceryl monostearate or glyceryl distearate may be employed. Such preparations may be manufactured in a known manner, for example by means of mixing, granulating, tableting, sugar coating or film coating processes.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is present as such, or mixed with water or an oil medium, for example, peanut oil, liquid paraffin, or olive oil.

Aqueous suspensions contain the active materials in admixture with excipients suitable for the manufacture of aqueous suspensions. Such excipients are suspending agents, for example, sodium carboxymethylcellulose, methylcellulose, hydroxypropylmethyl-cellulose, sodium alginate, polyvinylpyrrolidone gum tragacanth and gum acacia; dispersing or wetting agents may be naturally-occurring phosphatides, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitan monooleate, or condensation products of ethylene oxide with partial esters derived from fatty acids and hexitol anhydrides for example polyoxyethylene sorbitan monooleate.

The said aqueous suspensions may also contain one or more preservatives, for example, ethyl or n-propyl p-hydroxybenzoate, one or more colouring agents, such as sucrose or saccharin.

Oily suspension may be formulated by suspending the active ingredient in a vegetable oil, for example arachis oil, olive oil, sesame oil or coconut oil, or in a mineral oil such as liquid paraffin. The oily suspensions may contain a thickening agent, for example beeswax, hard paraffin or cetyl alcohol.

Sweetening agents, such as those set forth above, and flavouring agents may be added to provide a palatable oral preparation. These compositions may be preserved by this addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavouring and colouring agents, may also be present.

Pharmaceutical compositions for use in accordance with the invention may also be in the form of oil-in-water emulsions. The oily phase may be a vegetable oil, for example olive oil or arachis oils, or a mineral oil, for example liquid paraffin or mixtures of these. Suitable emulsifying agents may be naturally-occurring gums, for example gum acacia or gum tragacanth, naturally occurring phosphatides, for example soy bean lecithin, and esters or partial esters derived from fatty acids an hexitol anhydrides, for example sorbitan mono-oleate, and condensation products of the said partial esters with ethylene oxide, for example polyoxyethylene sorbitan monooleate. The emulsion may also contain sweetening and flavouring agents. Syrups and elixirs may be formulated with sweetening agents, for example glycerol, sorbitol or sucrose. In particular a syrup for diabetic patients can contain as carriers only products, for example sorbitol, which do not metabolise to glucose or which only metabolise a very small amount to glucose.

Such formulations may also contain a demulcent, a preservative and flavouring and coloring agents;

B) Parenterally, either subcutaneously, or intravenously, or intramuscularly, or intrasternally, or by infusion techniques, in the form of sterile injectable aqueous or oleaginous suspensions. This suspension may be formulated according to the known art using those suitable dispersing of wetting agents and suspending agents which have been mentioned above. The sterile injectable preparation may also be a sterile injectable solution or suspension in a non-toxic paternally-acceptable diluent or solvent, for example as a solution in 1,3-butane diol.

Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition fatty acids such as oleic acid find use in the preparation of injectables;

C) By inhalation, in the form of aerosols or solutions for nebulizers;

D) Rectally, in the form of suppositories prepared by mixing the drug with a suitable non-irritating excipient which is solid at ordinary temperature but liquid at the rectal temperature and will therefore melt in the rectum to release the drug. Such materials are cocoa butter and poly-ethylene glycols;

E) Topically, in the form of creams, ointments, jellies, collyriums, solutions or suspensions.

F) Vaginally, in the form of pessaries, tampons, creams, gels, pastes, foams or spray formulations containing in addition to the active ingredient such carriers as are known in the art to be appropriate.

The present invention is further illustrated in the Examples which follow:

EXAMPLES

Examples 1 to 4

SLOS has an NPC Phenotype

A pilot study was carried out on murine embryonic fibroblasts (MEFs), as follows:

Example 1

GSL Mistrafficking is Dependent on Cholesterol Reduction/7-DHC Elevation

Figure 4:
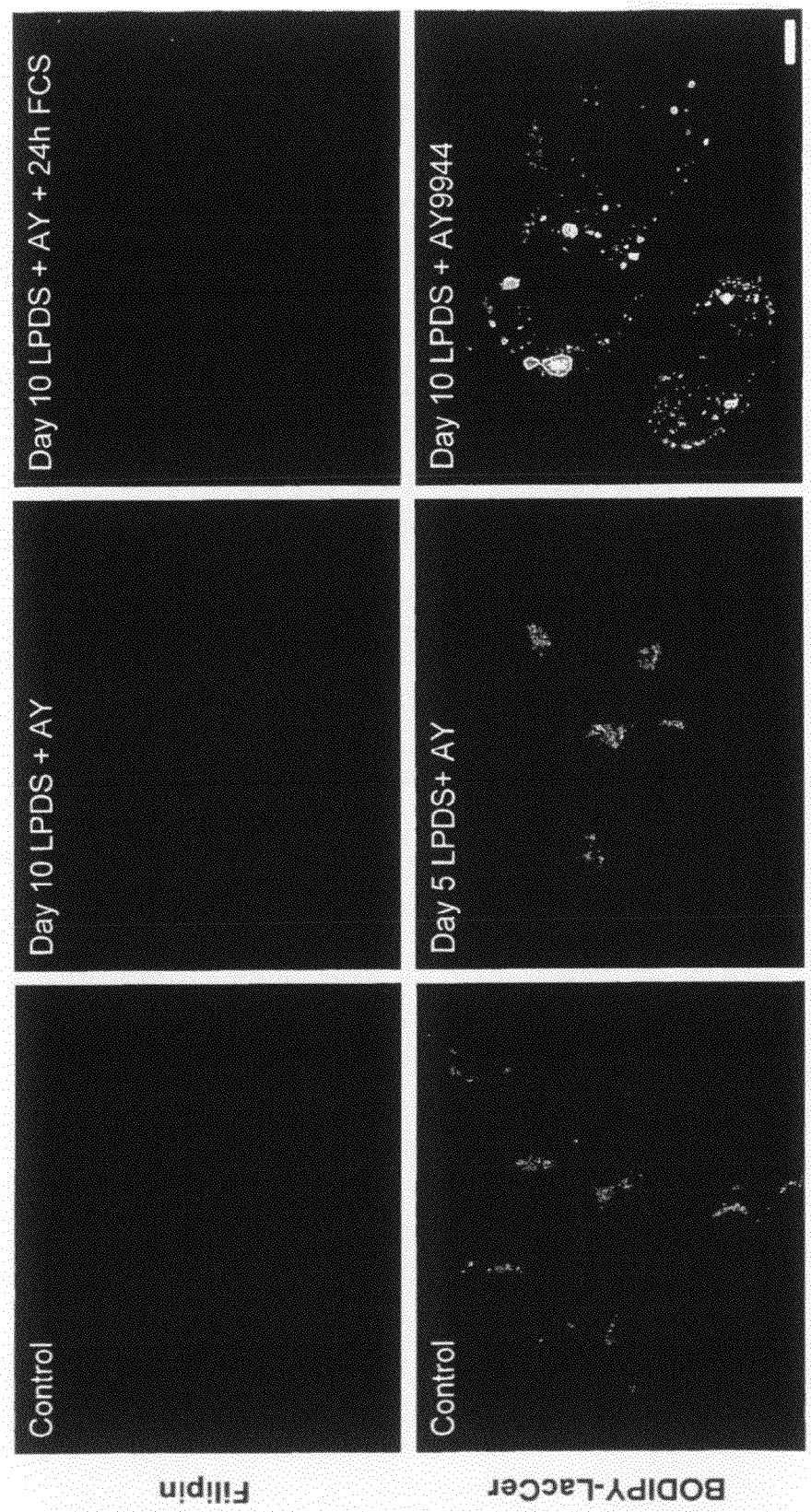
FIG. 4 consists of micrographs which together show the induction of an NPC phenotype in cholesterol null RAW cells.

Treatment of cells with AY9944 (a chemical inhibitor of 3β-hydroxysterol Δ7-reductase) leads to accumulation of 7-DHC (Teratology 1996; 54(3):115-25). RAW mouse macrophages grown in medium supplemented with LPDS for 5 days to elevate endogenous cholesterol biosynthesis were treated with 1 mM AY9944 in medium supplemented with lipoprotein deficient serum (LPDS) for a further 5 or 10 days to induce storage of 7-DHC. At 5 days post AY9944 treatment RAW cells showed a slight decrease in cholesterol levels (assessed by filipin, not shown), whereas, at 10 days post treatment, cholesterol levels were markedly reduced (FIG. 4, top panels). This correlated with abnormal transport of a fluorescent GSL analogue of lactosylceramide (LacCer)—BODIPY-LacCer. At 5 days post AY9944 treatment BODIPY-LacCer was transported to the Golgi following a 30 min pulse and 90 min chase (FIG. 4, lower panels). At 10 days post AY9944 BODIPY-LacCer was trapped in punctate LE/Lys indicative of GSL storage and a failure in lipid efflux out of the LE to the Golgi (FIG. 4). This was further highlighted by switching cells into medium containing 10% foetal calf serum (FCS) following 10 day treatment with AY9944, after which exogenously derived cholesterol became trapped in punctate LE (FIG. 4, top panels).

Thus, GSL mistrafficking appeared to be dependent on cholesterol reduction/7-DHC elevation.

FIG. 4 consists of micrographs which together show the induction of an NPC phenotype in cholesterol null RAW cells. All RAW cells were grown in medium supplemented with LPDS for 5 days (controls) to reduce exogenously derived cholesterol prior to addition of 1 μM AY9944 to inhibit endogenous cholesterol synthesis for a further 5 days or 10 days (as indicated). Alterations in sphingolipid trafficking were measured in live cells using BODIPY-LacCer (lower panels), cholesterol levels in fixed cells were measured with filipin (upper panels). Endocytic cholesterol storage in cholesterol depleted cells was induced by growth in medium supplemented with 10% FCS for a further 24 h. For each condition n=2, images are representative of at least 10 captured fields, scale bar=5 µm.

Example 2

GSLs are Stored in SLOS Cells Due to the Accumulation of 7-DHC

As SLOS fibroblasts grown in LPDS (to elevate 7-DHC; Mol Genet Metab 2002; 75(4):325-34) accumulate exogenous LDL-derived cholesterol in the LE/Lys system in a similar manner to NPC1 cells, it was assessed whether SLOS cells had altered GSL trafficking. Control, lathosterolosis ($Sc5d^{-/-}$), desmosterolosis ($DHCR24^{-/-}$), and SLOS ($DHCR7^{-/-}$) MEFs were grown in FCS or LPDS for 5 days prior to addition of BODIPY-LacCer to follow GSL transport. BODIPY-LacCer is correctly transported to the Golgi in all cells grown in FCS and LPDS, apart from the SLOS cells grown in LPDS where BODIPY-LacCer is incorrectly localized to punctate late endosomes and lysosomes (FIG. 5A). Normal transport of BODIPY-LacCer to the Golgi in MEF cells from the two other sterol biosynthetic pathway diseases, lathosterolosis (defective conversion of lathosterol to 7-DHC) (FIG. 5A), and desmosterolosis (desmosterol to cholesterol) (FIG. 5A) indicated that accumulation of 7-DHC alone caused abnormal endocytic transport of lipids. A possible reason for this is that 7-DHC belongs to a class of secondary amphiphiles, which include U18666A, 7-ketocholesterol, progesterone and imipramine, all of which are steroids or steroid analogues known to induce free cholesterol storage and abnormal lipid endocytosis in an identical manner to Niemann-Pick C1 cells (Brain Dev 1998; 20(1):50-2). It has also been shown that secondary amphiphiles induce GSL storage (J Biol Chem 2004; 279(25):26167-75).

This Example indicates that GSLs may be stored in SLOS cells due to the accumulation of 7-DHC.

Figure 5:
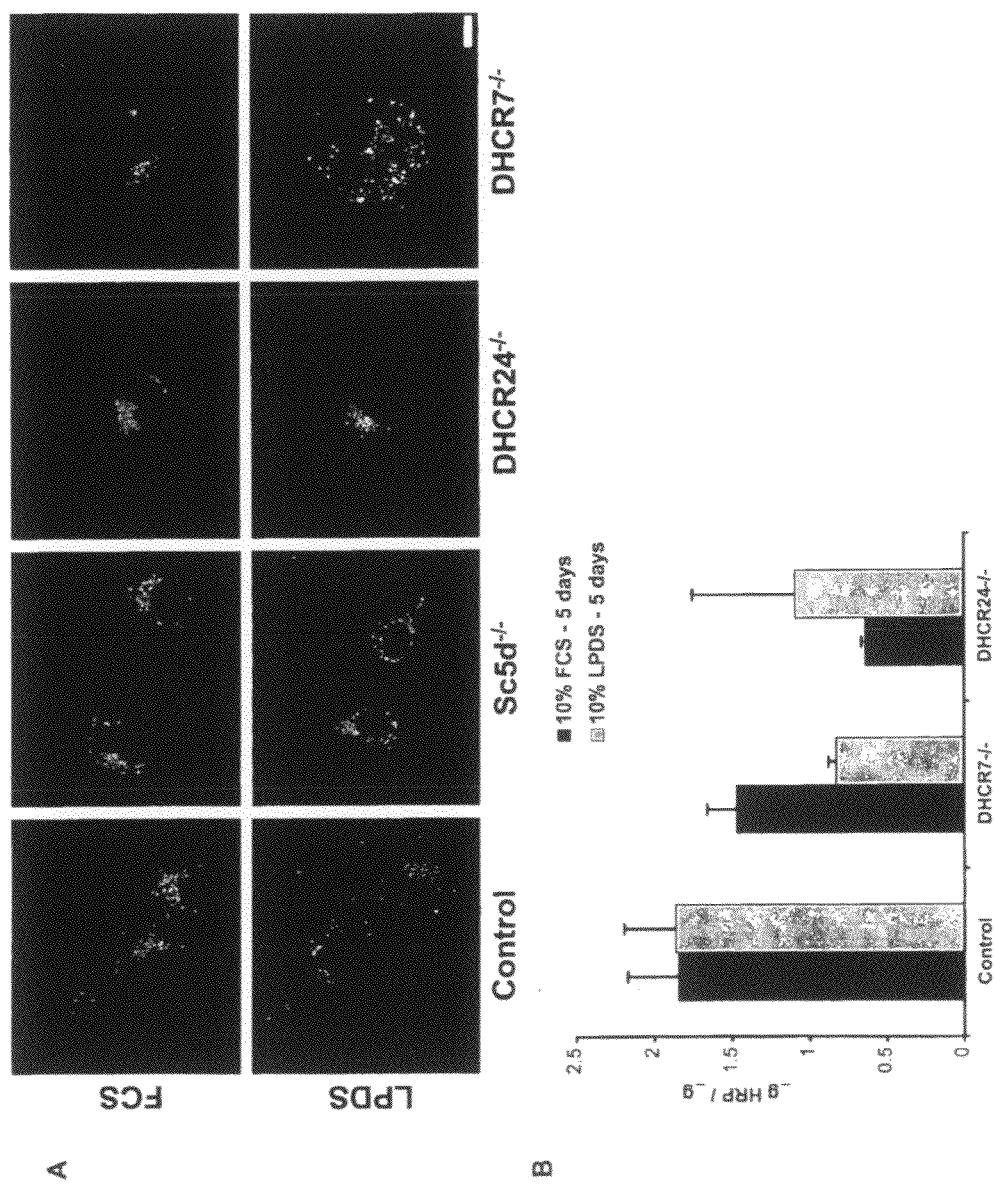
FIG. 5 shows the abnormal endocytic transport in SLOS MEFs.

FIG. 5 shows the abnormal endocytic transport in SLOS MEFs.

FIG. 5A consists of micrographs showing control, lathosterolosis ($Sc5d^{-/-}$), desmosterolosis ($DHCR24^{-/-}$), and SLOS ($DHCR7^{-/-}$) MEFs which were grown in medium with 10% FCS for 7 days (top panels) or 10% LPDS (to deplete extracellular derived cholesterol) for 7 days (lower panels). Sphingolipid transport was assessed by live pulse/chase transport (45 min pulse, 1 h chase, 37° C.) of 5 µM BODIPY-LacCer.

Example 3

Accumulation of 7-DHC in the SLOS MEFs Induces an Early to Late Endosome Transport Defect Further to the defective late endosome to Golgi transport of lipids observed in the SLOS cells, the total uptake of the fluid phase marker HRP into MEF cells grown in FCS or LPDS containing media was measured. Growth in LPDS for 5 days significantly reduced the amount of HRP uptake in the SLOS ($DHCR7^{-/-}$) MEFs (FIG. 5B). There was no effect of LPDS on the control MEFS (FIG. 5B) whereas the desmosterolosis ($DHCR24^{-/-}$) MEFs had low uptake in both FCS and LPDS (FIG. 5B). This indicated that the accumulation of 7-DHC in the SLOS MEFs induced an early to late endosome transport defect, resulting in limited uptake of HRP as has been described previously for NPC1 cells. This phenotype in NPC1 cells is also associated with GSL storage as depletion of stored GSLs via inhibition of biosynthesis with NB-DGJ leads to a correction in HRP uptake (J Biol Chem 2004; 279(25):26167-75).

FIG. 5B, is a graph of the total uptake of the fluid phase marker HRP (y-axis) for control, $DHCR7^{-/-}$ and $DHCR24^{-/-}$ MEFs (x axis), which were incubated with 3 mg/ml HRP for 2 h at 37° C. Fluid phase uptake of HRP was quantified using a commercial peroxidase kit. Bar=10 µm, n=3.

Example 4

SLOS MEFs Store GSLs Under Cholesterol-Deprived Conditions

Using a sensitive in-house HPLC assay, GSLs from cells and tissues can be quantified (Anal Biochem 2004; 331(2): 275-82). The GSL contents of MEF cells from control, SLOS ($DHCR7^{-/-}$) and desmosterolosis ($DHCR24^{-/-}$) mice grown either in FCS or LPDS containing media were quantified. After 5 days, cells were harvested and their GSLs extracted by a modified version of Fredman & Svennerholm (Anal Biochem 2004; 331(2):275-82). In the presence of FCS, SLOS MEFs had a slight increase in total GSLs, but this was not statistically significant compared to controls (FIG. 6B). Desmosterol is not a secondary amphiphile and as such is incapable of inducing an NPC1 phenotype which in turn accounts for the absence of phenotype. Decreased GSL content does not affect lipid transport as has been observed before following prolonged treatment with NB-DNJ (J Biol Chem 2004; 279(25):26167-75), hence the normal transport of GSLs to the Golgi in these cells described above (FIG. 5A). However, following 5 days growth in LPDS we see a large increase in all the GSL species in SLOS MEFs (FIG. 6A, 6B), in particular LacCer and gangliosides GM1 and GM2 (FIG. 6A). This is indicative of lysosomal storage and the profile of GSL storage is similar to that seen in NPC1 cells (J Biol Chem 2004; 279(25):26167-75). Thus SLOS MEFs do store GSLs under cholesterol-deprived conditions.

Figure 6:
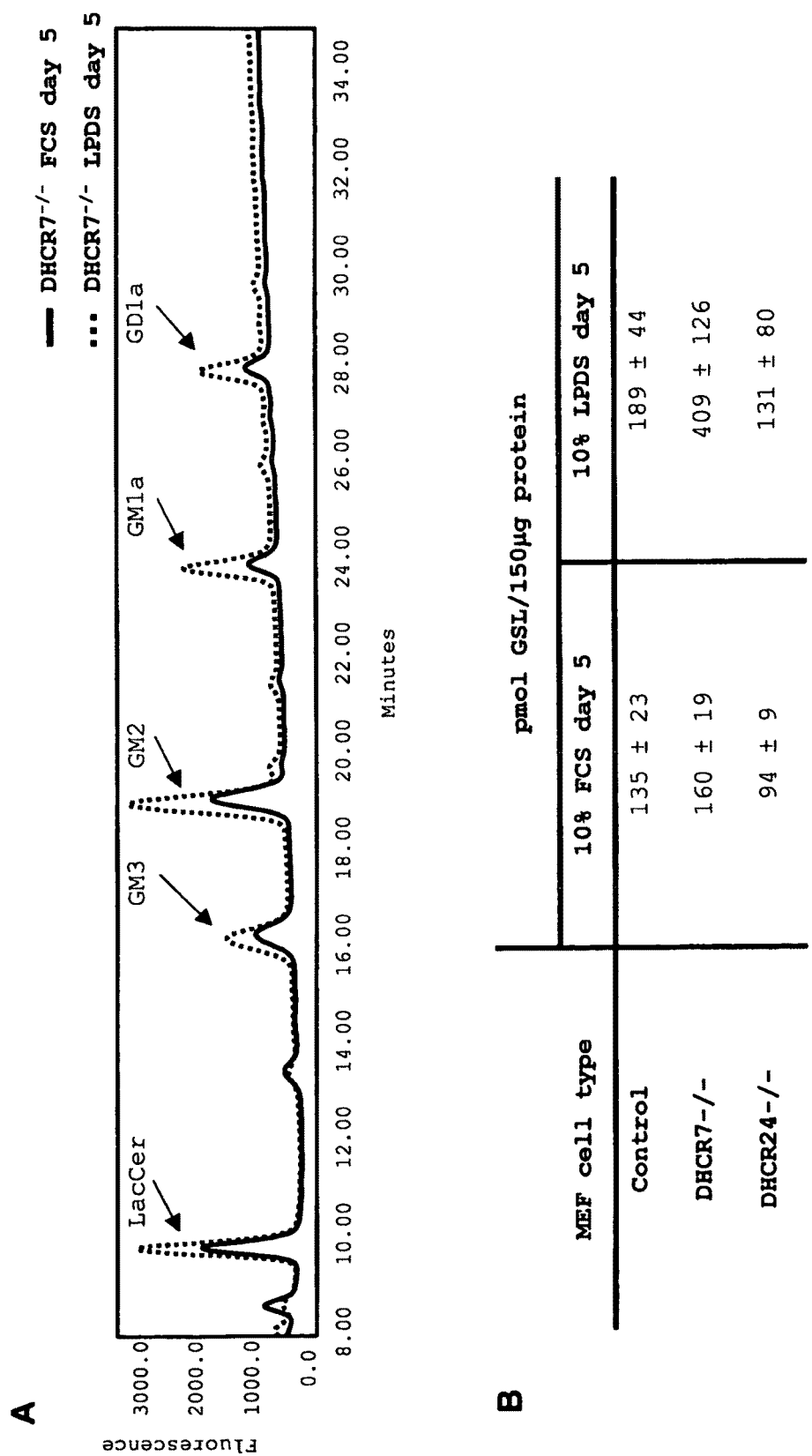
FIG. 6 evidences the glycosphingolipid (GSL) storage in Smith-Lemli-Opitz MEFs.

FIG. 6 shows glycosphingolipid storage in Smith-Lemli-Opitz MEFs. MEFs were harvested after 5 days growth in medium containing either 10% FCS or 10% LPDS. GSLs were extracted and purified according to a modified version of Fredman & Svennerholm. Samples were analysed by HPLC. FIG. 6A shows representative HPLC traces of GSLs from SLOS cells grown in FCS (red trace) or LPDS (green trace); equal amounts of both sample (according to protein content) were loaded. LacCer=lactosylceramide, GM3, GM2, GM1a and GD1a are all gangliosides. FIG. 6B gives the total GSL levels for control, SLOS ($DHCR7^{-/-}$) and desmosterolosis ($DHCR24^{-/-}$) cells grown in FCS or LPDS. For each experiment n=3.

Example 5

Figure 7:
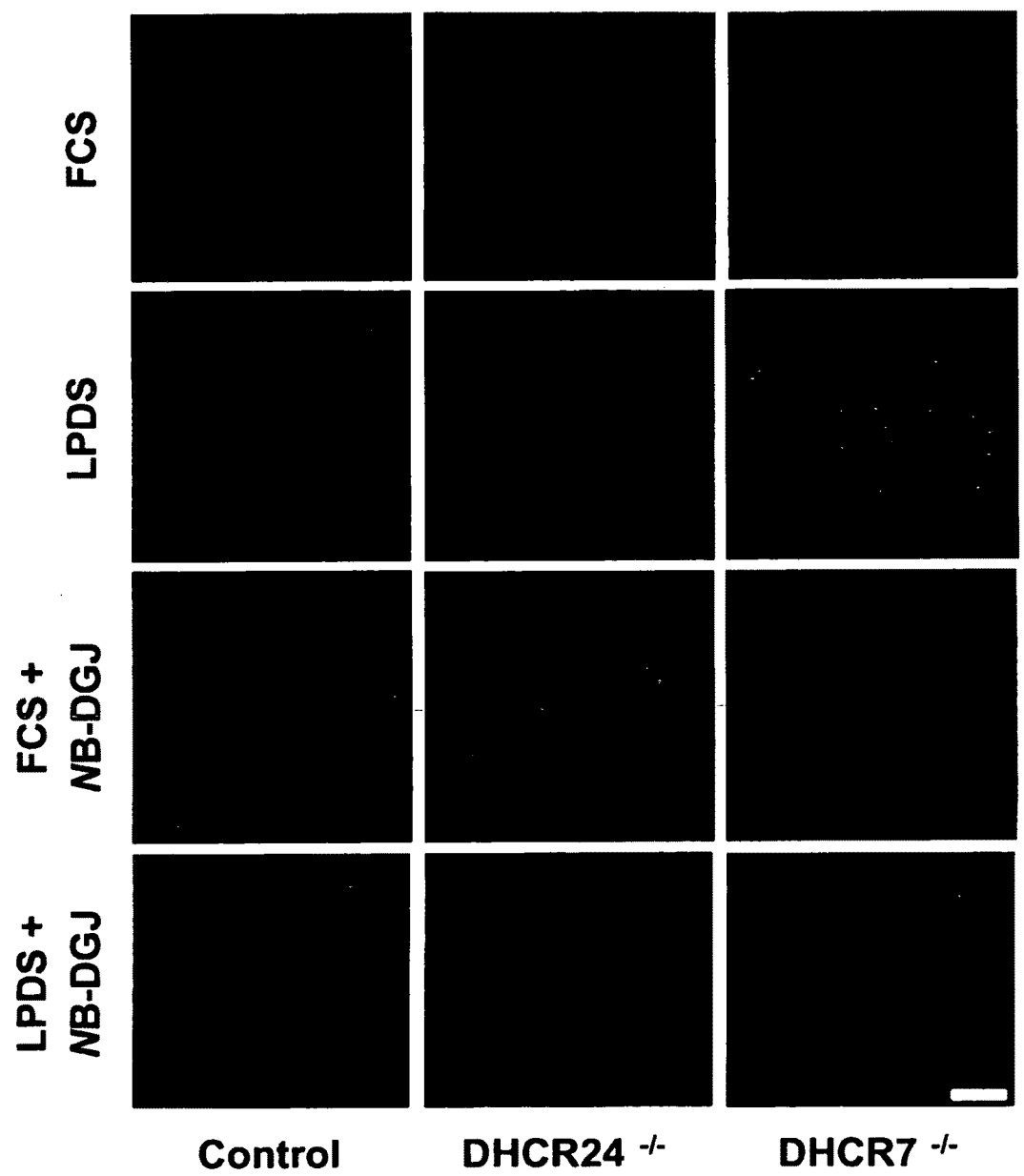
FIG. 7 consists of micrographs showing control, desmosterolosis (DHCR24$^{-/-}$) and SLOS (DHCR7$^{-/-}$) MEF cells, which were grown for 5 days in complete medium with either 10% FCS or 10% LPDS in the presence or absence of 50 μM NB-DGJ.
Figure 8:
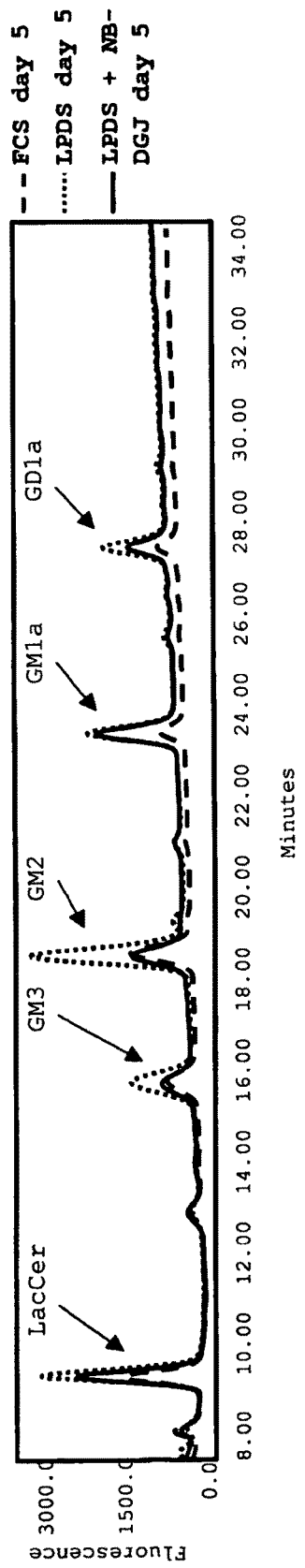
FIG. 8 shows HPLC traces of GSLs, which were extracted from harvested MEF cells grown for 5 days in FCS (orange trace), LPDS (red trace) or LPDS+NB-DGJ (blue trace).

Inhibition of GSL Biosynthesis Corrects Altered Endogenous Ganglioside GM1 Trafficking from the LE/Lys System A pilot study to investigate the effects of NB-DGJ treatment on altered GSL trafficking in SLOS cells grown in LPDS was conducted. Inhibition of GSL biosynthesis, via treatment of SLOS MEFs with NB-DGJ for 5 days in medium containing LPDS, corrected altered endogenous ganglioside GM1 trafficking (assessed by specific cholera toxin binding to ganglioside GM1 with subsequent internalization and transport) from the punctate LE/Lys system back to the Golgi (FIGS. 7 and 8). This would potentially allow LDL derived unesterified cholesterol to be correctly transported to the ER for utilization. The iminosugar (NB-DNJ/miglustat), which is already in use as a therapeutic agent for the human GSL storage disorder type 1 Gaucher disease (C. Neurobiol Dis 2004; 16(3):654-8), may therefore be of potential benefit to SLOS patients.

FIGS. 7 and 8 show that the altered GSL trafficking in SLOS MEFs is corrected following NB-DGJ treatment. FIG. 7 consists of micrographs showing control, desmosterolosis (DHCR24$^{-/-}$) and SLOS (DHCR7$^{-/-}$) MEF cells, which were grown for 5 days in complete medium with either 10% FCS or 10% LPDS in the presence or absence of 50 μM NB-DGJ. The effect of cholesterol depletion, GSL depletion, and both together on GSL trafficking was assessed using rhodamine conjugated cholera toxin B subunit. Cells were incubated with 2 μM cholera toxin for a 30 min pulse and 90 min chase in live cells at 37° C. followed by paraformaldehyde fixation. For each experiment n=3, scale bar=5 μm. FIG. 8 shows HPLC traces of GSLs, which were extracted, as for FIG. 6A, from harvested MEF cells grown for 5 days in FCS (orange trace), LPDS (red trace) or LPDS+NB-DGJ (blue trace).

In conclusion, it has now been shown that glycosphingolipids (GSLs) accumulate in MEF cells isolated from the SLOS mouse model and evidenced that the accumulation of GSLs contributes to defective intracellular endocytosis. In the context of SLOS, this defective endocytosis prevents correct delivery of exogenously derived cholesterol to the ER. In light of the endogenous cholesterol biosynthetic defect, any inhibition of exogenous cholesterol utilisation is deleterious. Inhibition of sphingolipid biosynthesis with, for instance NB-DNJ or NB-DGJ, leads to a correction in endocytosis, which would allow utilisation of the exogenously derived cholesterol.

In the brain of SLOS patients, exogenous cholesterol cannot cross the blood brain barrier, therefore the presence of GSLs alone may cause neurodegeneration, as is the case for Niemann-Pick C1. Reduction of GSLs may also (as well as improve endocytosis) lead to improved neuronal function and delay neuronal cell death. In essence SLOS is a disease where the accumulating substrate leads to the induction of another milder disease process (NPC1). SLOS patients may respond better than NPC1 patients to SRT owing to the milder phenotype.

Other precursors/analogues of cholesterol or other molecules generated in other disease states may induce NPC1 phenotypes. For example, there is a disease associated with almost every step of cholesterol biosynthesis post-squalene. In all of these diseases the precursor molecule accumulates. If like SLOS the precursor molecule is a class II amphiphile then it is especially likely that the sufferer will have a secondary NPC1 phenotype. It has previously been shown that the class II amphiphiles progesterone and U18666A can induce an NPC1 phenotype, and that treatment with an inhibitor of sphingolipid biosynthesis can reverse some of the cellular functions that become dysfunctional following class II amphiphile treatment. Thus, in the light of the finding that another naturally occurring class II amphiphile, 7-DHC, can also induce an NPC1 phenotype, any disorder incurring accumulation of a class II amphiphile may have a secondary NPC1 phenotype which can be treated with an inhibitor of sphingolipid biosynthesis (for instance NB-DNJ or NB-DGJ) leading to potential clinical benefit.

Example 6

Figure 9:
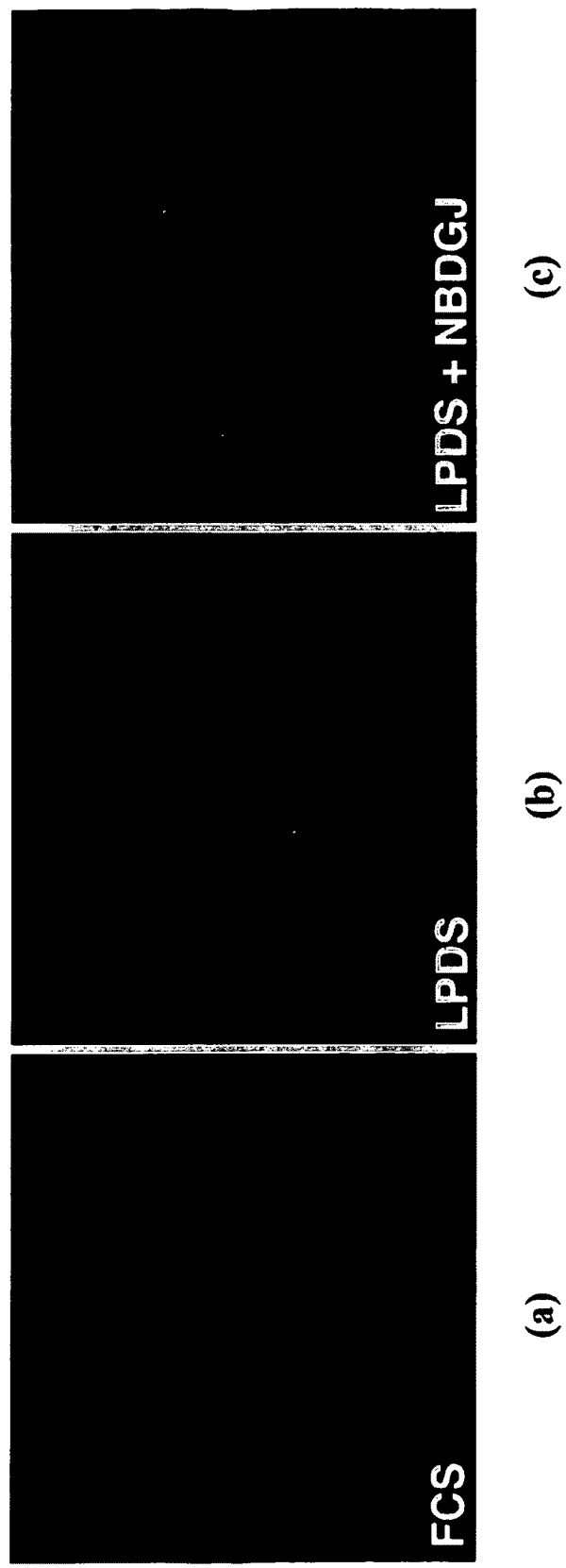
FIG. 9 consists of micrographs (a) (FCS=foetal calf serum), (b) (LPDS=lipoprotein deficient serum) and (c) (LPDS=lipoprotein deficient serum) showing the restoration of ER neutral lipid content in SLOS cells following treatment with NB-DGJ.

Restoration of ER Neutral Lipid Content in SLOS Cells Following Treatment with NB-DGJ DHCR7−/− mouse embryonic fibroblasts were grown under the conditions indicated in FIG. 9 (FCS=foetal calf serum, LPDS=lipoprotein deficient serum) for 5 days prior to staining of neutral lipids with Nile red. Under wild-type conditions (growth in FCS) Nile red stains the endoplasmic reticulum (ER) as expected. Inducing DHCR7−/− cells into a Smith-Lemli-Opitz phenotype by growth in LPDS leads to a depletion in ER neutral lipids and an elevation in punctate staining indicative of a block in transport to the ER. Combined growth in LPDS and NB-DGJ (50 mM) overcomes this transport defect leading to restoration of normal levels of neutral lipids at the ER, indicative of normal cholesterol esterification. N=2.

Example 7

Tablet Composition

Tablets, each weighing 0.15 g and containing 25 mg of an inhibitor of sphingolipid biosynthesis, for use in accordance with the invention, are manufactured as follows:

| Composition for 10,000 tablets | |
|---|---|
| Active compound | (250 g) |
| Lactose | (800 g) |
| Corn starch | (415 g) |
| Talc powder | (30 g) |
| Magnesium stearate | (5 g) |

The active compound, lactose and half of the corn starch are mixed. The mixture is then forced through a sieve 0.5 mm mesh size. Corn starch (10 g) is suspended in warm water (90 ml). The resulting paste is used to granulate the powder. The granulate is dried and broken up into small fragments on a sieve of 1.4 mm mesh size. The remaining quantity of starch, talc and magnesium is added, carefully mixed and processed into tablets.

Example 8

Injectable Formulation

| Formulation A | |
|---|---|
| Active compound | 200 mg |
| Hydrochloric Acid Solution 0.1M or Sodium Hydroxide Solution 0.1M q.s. to pH | 4.0 to 7.0 |
| Sterile water q.s. to | 10 ml |

The inhibitor of sphingolipid biosynthesis, for use in accordance with the invention, is dissolved in most of the water (35° 40° C.) and the pH adjusted to between 4.0 and 7.0 with the hydrochloric acid or the sodium hydroxide as appropriate. The batch is then made up to volume with water and filtered through a sterile micropore filter into a sterile 10 ml amber glass vial (type 1) and sealed with sterile closures and overseals.

| Formulation B | |
| --- | --- |
| Active Compound | 125 mg |
| Sterile, Pyrogen-free, pH 7 Phosphate Buffer, q.s. to | 25 ml |
| Active compound | 200 mg |
| Benzyl Alcohol | 0.10 g |
| Glycofurol 75 | 1.45 g |
| Water for injection q.s to | 3.00 ml |

The active compound is dissolved in the glycofurol. The benzyl alcohol is then added and dissolved, and water added to 3 ml. The mixture is then filtered through a sterile micropore filter and sealed in sterile 3 ml glass vials (type 1).

Example 9

Syrup Formulation

| Active compound | 250 mg |
| --- | --- |
| Sorbitol Solution | 1.50 g |
| Glycerol | 2.00 g |
| Sodium benzoate | 0.005 g |
| Flavour | 0.0125 ml |
| Purified Water q.s. to | 5.00 ml |

The inhibitor of sphingolipid biosynthesis, for use in accordance with the invention, is dissolved in a mixture of the glycerol and most of the purified water. An aqueous solution of the sodium benzoate is then added to the solution, followed by addition of the sorbitol solution and finally the flavour. The volume is made up with purified water and mixed well.

The invention claimed is:

1. A method of treating a subject having a disease which has a secondary Niemann-Pick type C disease like cellular phenotype, wherein the disease is Smith-Lemli-Opitz Syndrome (SLOS), CHILD syndrome, XLD chondrodysplasia punctata type 2, Conradi-Hünnermann-Happle syndrome, or HEM dysplasia, the method comprising selecting the subject having the disease, and administering to the subject an effective amount of an inhibitor of sphingolipid biosynthesis wherein the inhibitor of sphingolipid biosynthesis is N-butyldeoxynojirimycin; N-nonyldeoxynojirimycin; N-butyldeoxygalactonojirimycin; N-5-adamantane-1-yl-methoxypentyl-deoxynojirimycin; alpha-homogalactonojirimycin; nojirimycin; deoxynojirimycin; N7-oxadecyl-deoxynojirimycin; deoxygalactonojirimycin; N-butyl-deoxygalactonojirimycin; N-nonyl-deoxygalactonojirimycin; N-nonyl-6deoxygalactonojirimycin; N7-oxanonyl-6deoxy-DGJ; alpha-homoallonojirimycin; or beta-1-C-butyl-deoxygalactonojirimycin.

2. The method of claim 1 wherein the inhibitor is an inhibitor of a glycosyltransferase or a sulfotransferase.

3. The method of claim 2 wherein the glycosyltransferase is a glucosyltransferase, sialyltransferase, galactosyltransferase, ceramide galactosyltransferase, fucosyltransferase, or N-acetylhexosaminetransferase.

4. The method of claim 1 wherein the inhibitor is an inhibitor of glucosylceramide synthase.

5. The method of claim 1 wherein the inhibitor is an inhibitor of ceramide biosynthesis.

6. The method of claim 1 wherein the inhibitor is an inhibitor of serine palmitoyltransferase or an inhibitor of dihydroceramide synthase.

7. The method of claim 1 wherein the inhibitor of sphingolipid biosynthesis is an inhibitor of ceramide degradation.

8. The method of claim 1 wherein the inhibitor of sphingolipid biosynthesis is an inhibitor of acidceramidase.

9. The method of claim 1 wherein the disease which has a secondary Niemann-Pick type C disease like cellular phenotype is a disease which incurs the accumulation of a class II amphiphile.

10. The method of claim 9 wherein the class II amphiphile is a precursor or analogue of cholesterol.

11. The method of claim 1 further comprising coadministering the compound with cholesterol and/or an inhibitor of de novo cholesterol biosynthesis, wherein the disease is Smith-Lemli-Opitz Syndrome (SLOS).

12. The method of claim 1, wherein the inhibitor of sphingolipid biosynthesis is N-butyldeoxynojirimycin, and the disease is Smith-Lemli-Opitz Syndrome (SLOS).

13. The method of claim 1, wherein the disease is Smith-Lemli-Opitz Syndrome (SLOS).

* * * * *